United States Patent
Numata et al.

(10) Patent No.: US 11,174,572 B2
(45) Date of Patent: Nov. 16, 2021

(54) COMPOSITE MOLDING COMPOSITION INCLUDING FIBROIN-LIKE PROTEIN, AND METHOD FOR PRODUCING COMPOSITE MOLDING COMPOSITION

(71) Applicants: RIKEN, Wako (JP); SPIBER INC., Tsuruoka (JP)

(72) Inventors: Keiji Numata, Wako (JP); Kousuke Tsuchiya, Wako (JP); Junichi Sugahara, Tsuruoka (JP); Takaoki Ishii, Tsuruoka (JP); Hongfang Chi, Tsuruoka (JP)

(73) Assignees: RIKEN, Wako (JP); SPIBER INC., Tsuruoka (JP)

( * ) Notice: Subject to any disclaimer, the term of this patent is extended or adjusted under 35 U.S.C. 154(b) by 0 days.

(21) Appl. No.: 16/326,081

(22) PCT Filed: Jul. 24, 2017

(86) PCT No.: PCT/JP2017/026734
§ 371 (c)(1),
(2) Date: Feb. 15, 2019

(87) PCT Pub. No.: WO2018/034111
PCT Pub. Date: Feb. 22, 2018

(65) Prior Publication Data
US 2019/0186050 A1 Jun. 20, 2019

(30) Foreign Application Priority Data

Aug. 19, 2016 (WO) .................. PCT/JP2016/074289

(51) Int. Cl.
| | | |
|---|---|---|
| D01F 4/02 | (2006.01) | |
| D01F 4/00 | (2006.01) | |
| D01D 1/02 | (2006.01) | |
| A61L 27/22 | (2006.01) | |
| D01D 5/16 | (2006.01) | |
| D01F 1/10 | (2006.01) | |
| D01F 6/68 | (2006.01) | |

(52) U.S. Cl.
CPC ............... *D01F 4/02* (2013.01); *A61L 27/22* (2013.01); *D01D 1/02* (2013.01); *D01D 5/16* (2013.01); *D01F 1/10* (2013.01); *D01F 4/00* (2013.01); *D01F 6/68* (2013.01)

(58) Field of Classification Search
None
See application file for complete search history.

(56) References Cited

U.S. PATENT DOCUMENTS

| | | | |
|---|---|---|---|
| 8,278,416 | B1 | 10/2012 | Johansson et al. |
| 2012/0041177 | A1 | 2/2012 | Johansson et al. |
| 2012/0231499 | A1 | 9/2012 | Lee et al. |
| 2013/0065278 | A1 | 3/2013 | Johansson et al. |
| 2013/0172478 | A1 | 7/2013 | Bausch et al. |
| 2014/0058066 | A1 | 2/2014 | Sekiyama et al. |
| 2014/0245923 | A1 | 9/2014 | Sugahara et al. |
| 2015/0291673 | A1 | 10/2015 | Sekiyama et al. |
| 2015/0361144 | A1 | 12/2015 | Osawa et al. |
| 2015/0374833 | A1 | 12/2015 | Osawa et al. |
| 2015/0376247 | A1 | 12/2015 | Osawa et al. |
| 2017/0283474 | A1 | 10/2017 | Johansson et al. |

FOREIGN PATENT DOCUMENTS

| | | |
|---|---|---|
| CA | 3012817 A1 | 11/2017 |
| CA | 3012821 A1 | 11/2017 |
| EP | 3351584 A1 | 7/2018 |
| JP | 48-20613 A | 6/1973 |
| JP | 48-29557 A | 9/1973 |
| JP | 6-94518 B2 | 11/1994 |
| JP | 2010-95596 A | 4/2010 |
| JP | 2014-129639 A | 7/2014 |
| WO | WO 2007/078239 A2 | 7/2007 |
| WO | WO 2010/123450 A1 | 10/2010 |
| WO | WO 2011/112046 A2 | 9/2011 |
| WO | WO 2011/113592 A1 | 9/2011 |
| WO | WO 2012/165476 A1 | 12/2012 |
| WO | WO 2012/165477 A1 | 12/2012 |
| WO | WO 2013/065650 A1 | 5/2013 |
| WO | WO 2014/103799 A1 | 7/2014 |
| WO | WO 2014/175177 A1 | 10/2014 |
| WO | WO 2014/175178 A1 | 10/2014 |
| WO | WO 2014/175179 A1 | 10/2014 |

(Continued)

OTHER PUBLICATIONS

Gatesy et al., "Extreme Diversity, Conservation, and Convergence of Spider Silk Fibroin Sequences", Science, Mar. 2001, vol. 291, pp. 2603-2605.*
Baker et al., "Chemoenzymatic Synthesis of Poly(L-alanine) in Aqueous Environment", Biomacromolecules, vol. 13, Mar. 1, 2012, pp. 947-951.
Cohen et al., "Nonchromosomal Antibiotic Resistance in Bacteria: Genetic Transformation of *Escherichia coli* by R-Factor DNA", Proc. Nat. Acad. Sci., vol. 69, No. 8, Aug. 1972, pp. 2110-2114.
Hagn et al., "A Conserved Spider Silk Domain Acts as a Molecular Switch That Controls Fibre Assembly", Nature, vol. 465, May 13, 2010, pp. 239-242.
Ling et al., "Synchrotron FTIR Microspectroscopy of Single Natural Silk Fibers", Biomacromolecules, vol. 12, Jul. 26, 2011, pp. 3344-3349.

(Continued)

*Primary Examiner* — Suzanne M Noakes
(74) *Attorney, Agent, or Firm* — Birch, Stewart, Kolasch & Birch, LLP

(57) ABSTRACT

Provided are a composite molding composition such as a composite film and a composite fiber that have properties such as an improved tensile strength, strain and toughness as a result of blending a peptide or polyamino acid having a β-sheet structure with a natural or artificially modified fibroin-derived protein; a method for producing such composite molding composition; and a method for improving the physical properties of a composite molding composition containing a fibroin-derived protein.

25 Claims, 7 Drawing Sheets

Specification includes a Sequence Listing.

(56) References Cited

FOREIGN PATENT DOCUMENTS

| WO | WO 2017/030197 A1 | 2/2017 |
|---|---|---|
| WO | WO 2017/047504 A1 | 3/2017 |
| WO | WO 2017/188430 A1 | 11/2017 |
| WO | WO 2017/188434 A1 | 11/2017 |

OTHER PUBLICATIONS

Numata et al., "Use of Extension-Deformation-Based Crystallisation of Silk Fibres to Differentiate Their Functions in Nature", Soft Matter, Jun. 30, 2015, pp. 6335-6342.

Numata, "Poly(AminoAcid)s/Polypeptides as Potential Functional and Structural Materials", Polymer Journal, vol. 47, Published Online Jun. 3, 2015, pp. 537-545.

Rammensee et al., "Assembly Mechanism of Recombinant Spider Silk Proteins", PNAS, vol. 105, No. 18, May 6, 2008, pp. 6590-6595.

Teulé et al., "A Protocol for the Production of Recombinant Spider Silk-Like Proteins for Artificial Fiber Spinning", Nature Protocols, vol. 4, No. 3, 2009 (Published Online Feb. 19, 2009), pp. 341-355.

Tsuchiya et al., "Papain-Catalyzed Chemoenzymatic Synthesis of Telechelic Polypeptides Using Bis(Leucine Ethyl Ester) Initiator", Macromol. Biosci., vol. 16, 2016, pp. 1001-1008.

Tsuchiya et al., "Tensile Reinforcement of Silk Films by the Addition of Telechelic-Type Polyalanine", Biomacromolecules, vol. 18, Jan. 24, 2017, pp. 1002-1009.

Vollrath et al., "Silks as Ancient Models for Modem Polymers", Polymer, vol. 50, Available Online Oct. 7, 2009, pp. 5623-5632.

Zoller et al., "Oligonucleotide-directed Mutagenesis Using M13-derived Vectors: An Efficient and General Procedure for the Production of Point Mutations in Any Fragment of DNA", Nucleic Acids Research, vol. 10, No. 20, 1982, pp. 6487-6500.

Office Action dated Apr. 27, 2021, in Japanese Patent Application No. 2018-534312.

\* cited by examiner

COMPOSITE MOLDING COMPOSITION INCLUDING FIBROIN-LIKE PROTEIN, AND METHOD FOR PRODUCING COMPOSITE MOLDING COMPOSITION

TECHNICAL FIELD

The present invention relates to a composite molding composition including a fibroin-like protein and a method for producing the same.

ELECTRONIC SEQUENCE LISTING

The contents of the electronic sequence listing created on 15 Feb. 2019, named 2019-02-15_SequenceListing_5521-0201PUS1.txt and 121,414 bytes in size, is hereby incorporated by reference in its entirety.

BACKGROUND ART

Natural spider silk composed of fibroin is excellent in properties against physical changes, such as tensile strength, toughness and extensibility, and it is a polypeptide fiber having, for example, toughness about 5 times that of iron of the same weight. Moreover, it has excellent heat resistance, as well as high biocompatibility and biodegradability because it is formed from polypeptide. However, unlike silkworms whose natural silks are industrially utilized, spiders are difficult to rear in a massive manner. For this reason, attempts have been made to produce artificial synthetic fibers imitating spider silk and then apply them to materials such as yarns or sheets having the above-mentioned properties against physical changes, biocompatibility and biodegradability (Patent documents 1 to 5). For the above properties, however, production of artificial fibers comparable to natural spider silks has not been successful so far.

In the structure of natural spider silk, polyalanine forming a β-sheet structure and a polar region rich in glycine are repeated to form a core portion, at both sides of which are arranged an amino terminal domain and a carboxyl terminal domain that are non-repetitive and highly conserved, thereby providing a random coil structure, a β sheet structure and a helix structure, and it is considered that the excellent characteristics of natural spider silk is attributed to the mixture of these structures, and thus the structural characteristics thereof have been studied (Non-Patent Documents 1 to 3). Also, when spinning in spider's body, unlike ordinary proteins, spider protein shows high solubility when stored at high concentration, and yet, it changes into an extremely strong fiber as needed (Non-Patent Document 2). However, the structural characteristics and production mechanism of spider silk have not necessarily been clarified yet.

The inventors of the present invention have clarified the process of producing dragline silk in the dragline silk gland of *Nephila clavata*, thus making it clear that the formation of a granular structure by the β sheet structure of a spider silk fibroin protein is important for allowing the spider silk to exhibit its physical properties (Patent Document 6).

PRIOR ART DOCUMENTS

Patent Documents

Patent Document 1: International Publication WO2007/078239
Patent Document 2: International Publication WO2010/123450
Patent Document 3: International Publication WO2011/112046
Patent Document 4: International Publication WO2012/165476
Patent Document 5: International Publication WO2013/065650
Patent Document 6: International Publication WO2017/030197

Non-Patent Documents

Non-Patent Document 1: by Numata K et al., Soft Matter Jun. 30, 2015, 11, 6335-6342
Non-Patent Document 2: by Hagn F et al., Nature. 2010; 465 (7295): 239-242
Non-patent document 3: by Teule F et al., Nature Protocols 2009; 4: 341-355

SUMMARY OF THE INVENTION

Problems to be Solved by the Invention

Based on the production mechanism of the dragline silk of natural spider in the spider body as well as the factors that bring out the excellent properties, such mechanism is applied to the production of artificial fibers, thereby providing a composite molding composition containing a fibroin-like protein having properties such as high strength and toughness; a method for producing the composition; and a composite molding composition such as composite fiber, composite film and composite resin produced by the production method; and a method for improving the physical properties of the composite molding composition.

Means for Solving the Problems

The inventors of the present invention have found out that a composite molding composition produced by mixing a natural fibroin protein or an artificially produced fibroin-like protein with a polypeptide or polyamino acid having a β-sheet structure, and then molding the mixture, exhibits physical properties such as excellent tensile strength, strain and toughness as compared with a molded composition not including such polypeptide or polyamino acid having a β-sheet structure, and thus achieved the present invention.

Specifically, the present invention provides a composition including a fibroin-derived protein and a polypeptide and/or polyamino acid having a β-sheet structure.

Further, the composition may be a composite molding composition which is obtained by molding the fibroin-derived protein blended with the polypeptide and/or polyamino acid having the β-sheet structure.

The composite molding composition may be the one retaining the β-sheet structure derived from the polypeptide and/or polyamino acid.

The composite molding composition may be the one selected from a composite fiber, a composite film, a composite gel or a composite molded body.

Also, the present invention provides a composite molding composition formed of a fibroin-derived protein blended with a polypeptide and/or polyamino acid having a β-sheet structure,
wherein the composite molding composition is selected from a composite fiber, a composite film and a composite gel, and is produced by a method including:

(i) preparing a dope solution in which the fibroin-derived protein and the polypeptide and/or polyamino acid having the β-sheet structure are dissolved; and (ii) molding the composite molding composition from the dope solution.

Moreover, the present invention provides a pre-drawn composite molding composition being selected from a composite fiber or a composite film, and produced by a method including the above-mentioned processes (i) and (ii) and (iii) drawing the composite molding composition obtained in the process (ii) in a solvent and then drying the composite molding composition.

Furthermore, the present invention provides a composite molding composition being a composite molded body and produced by a method including:

(i) preparing a mixture by mixing a fibroin-derived protein and a polypeptide and/or polyamino acid having a β-sheet structure; and (ii) heating the mixture while applying a pressure thereto.

In the composite molding composition according to the present invention, the fibroin-derived protein may be selected from:

(i) a natural fibroin-derived protein; and/or
(ii) a modified fibroin-derived protein.

In the composite molding composition according to the present invention, the natural fibroin-derived protein may be at least one selected from the group consisting of a silk fibroin-derived silk protein (silk fibroin protein), a spider thread fibroin-derived spider thread protein (spider thread fibroin protein) and a hornet silk fibroin-derived hornet silk protein.

In the composite molding composition according to present invention, the modified fibroin-derived protein may be a modified fibroin-derived protein having a domain sequence represented by the following formula (I):

$$[(A)_n \text{ motif-REP}]_m \qquad (I),$$

wherein as compared to a naturally derived fibroin, at least one or a plurality of the glycine residues in REP are substituted with a different amino acid residue(s), and the domain sequence has an amino acid sequence with a reduced content of glycine residues,

[In the formula (I), $(A)_n$ motif represents an amino acid sequence consisting of 2 to 20 amino acid residues; and the number of alanine residues relative to a total number of the amino acid residues in the $(A)_n$ motif is 40% or more;

REP represents an amino acid sequence consisting of 2 to 200 amino acid residues;

m represents an integer of 2 to 300;

the plurality of $(A)_n$ motifs may be the same amino acid sequences or different amino acid sequences; and the plurality of REPs may be the same amino acid sequences or different amino acid sequences.].

In the modified fibroin-derived protein of the composite molding composition according to the present invention, the domain sequence, as compared to a naturally derived fibroin, may have an amino acid sequence equivalent to an amino acid sequence in which in at least one motif sequence selected from GGX and GPGXX (where X represents an amino acid residue other than glycine) in REP, one glycine residue in said at least one motif sequence or a plurality of the motif sequences is substituted with a different amino acid residue(s); and a ratio of the motif sequences in which the glycine residue is substituted with a different amino acid residue(s) is 10% or more with respect to all the motif sequences.

In the modified fibroin-derived protein, a maximum value of x/y (%) is 20% or more in which x represents a sum total of the numbers of amino acid residues in two adjacent [$(A)_n$ motif-REP] units, provided that, the number of amino acid residues in REPs of two adjacent [$(A)_n$ motif-REP] units is sequentially compared from the N-terminal side to the C-terminal side, and that when the number of amino acid residues in an REP having a smaller number of amino acid residues is defined as 1, a ratio of the number of amino acid residues in the other REP thereto becomes 2 to 3.5; and y represents a total number of amino acid residues in the domain sequence.

In the composite molding composition, the modified fibroin-derived protein represented by the formula (I) may be a modified fibroin-derived protein having an amino acid sequence represented by SEQ ID NO: 1 to 19.

In the composite molding composition according the present invention, the fibroin-derived protein may be a fibroin-derived protein having a homology of 80% or more, preferably 85% or more, more preferably 90% or more, even more preferably 95% or more, with respect to the amino acid sequence of the fibroin-derived protein.

In the composite molding composition according to the present invention, the polyamino acid having the β-sheet structure may be a polyalanine.

In the composite molding composition according to the present invention, the polyalanine may be selected from a linear polyalanine (L-polyAla) or a telechelic polyalanine (T-polyAla).

Also, the present invention provides a method for producing a composite molding composition that is formed of a fibroin-derived protein blended with a polypeptide and/or polyamino acid having a β-sheet structure, and is selected from a composite fiber, a composite film and a composite gel, including:

(i) preparing a dope solution in which the fibroin-derived protein and the polypeptide and/or polyamino acid having the β-sheet structure are dissolved; and (ii) producing the composite molding composition by performing spinning from the dope solution or further performing drawing.

Further, the present invention provides a method for producing a composite molded body formed of a fibroin-derived protein blended with a polypeptide and/or polyamino acid having a β-sheet structure, including:

(i) preparing a mixture by mixing a powder fibroin-derived protein with a powder polypeptide and/or powder polyamino acid having the β-sheet structure; and (ii) heating the mixture while applying a pressure thereto.

Moreover, the present invention provides a method for producing a pre-drawn-composite molding composition, including:

(i) drawing, in a solvent, the composite molding composition produced by the above-mentioned method; and (ii) drying the composite molding composition thus drawn.

In the method according to the present invention, the fibroin-derived protein may be selected from:

(i) a natural fibroin-derived protein; and/or
(ii) a modified fibroin-derived protein.

In the method according to the present invention, the natural fibroin-derived protein may be at least one selected from the group consisting of a silk fibroin-derived silk protein (silk fibroin protein), a spider thread fibroin-derived spider thread protein (spider thread fibroin protein) and a hornet silk fibroin-derived hornet silk protein.

In the production method according to the present invention, the modified fibroin-derived protein may be a modified fibroin-derived protein having a domain sequence represented by the following formula (I):

[Chemical formula 2]

$$[(A)_n \text{ motif-REP}]_m \quad (I),$$

wherein as compared to a naturally derived fibroin, at least one or a plurality of the glycine residues in REP are substituted with a different amino acid residue(s), and the domain sequence has an amino acid sequence with a reduced content of glycine residues,

[In the formula (I), $(A)_n$ motif represents an amino acid sequence consisting of 2 to 20 amino acid residues; and the number of alanine residues relative to a total number of the amino acid residues in the $(A)_n$ motif is 40% or more;

REP represents an amino acid sequence consisting of 2 to 200 amino acid residues;

m represents an integer of 2 to 300;

the plurality of $(A)_n$ motifs may be the same amino acid sequences or different amino acid sequences; and the plurality of REPs may be the same amino acid sequences or different amino acid sequences.].

In the modified fibroin-derived protein of the production method according to the present invention, the domain sequence, as compared to a naturally derived fibroin, may have an amino acid sequence equivalent to an amino acid sequence in which in at least one motif sequence selected from GGX and GPGXX (where X represents an amino acid residue other than glycine) in REP, one glycine residue in at least one or a plurality of the motif sequences is substituted with a different amino acid residue(s); and a ratio of the motif sequences with the glycine residue substituted with a different amino acid residue(s) is 10% or more, 20% or more, more preferably 30% or more, most preferably 40% or more with respect to all the motif sequences.

In the modified fibroin-derived protein of the production method according to the present invention, a maximum value of x/y (%) may be 20% or more in which x represents a sum total of the numbers of amino acid residues in two adjacent $[(A)_n$ motif-REP] units, provided that, the number of amino acid residues in REPs of two adjacent $[(A)_n$ motif-REP] units is sequentially compared from the N-terminal side to the C-terminal side, and that when the number of amino acid residues in an REP having a smaller number of amino acid residues is defined as 1, a ratio of the number of amino acid residues in the other REP thereto becomes 2 to 3.5; and y represents a total number of amino acid residues in the domain sequence.

In the production method according to the present invention, the modified fibroin-derived protein represented by the formula (I) may be a modified fibroin-derived protein having an amino acid sequence represented by SEQ ID NO: 1 to 19.

The fibroin-derived protein may be a fibroin-derived protein having a homology of 80% or more, preferably 85% or more, more preferably 90% or more, even more preferably 95% or more, with respect to the amino acid sequence of the fibroin-derived protein.

In the production method according to the present invention, the polyamino acid having the β-sheet structure may be a polyalanine.

In the production method according to the present invention, the polyalanine may be selected from a linear polyalanine or a telechelic polyalanine.

Further, the present invention provides a method for improving physical properties of a composite molding composition by blending a fibroin-derived protein with a polypeptide and/or polyamino acid having a β-sheet structure.

Still further, the present invention provides a method for improving physical properties of the composite molding composition, the method further including: drawing the composite molding composition in a solvent and then drying the composite molding composition.

In the method for improving physical properties of the composite molding composition, the improvements in physical properties are an increase in tensile strength, an increase in strain and/or an increase in toughness.

Effects of the Invention

It is possible to provide a composite molding composition such as a composite fiber, a composite film, and a composite gel including a fibroin-like polypeptide fiber having physical properties such as high toughness, strain (fracture elongation) and tensile strength (stress), and a method for producing the same.

DESCRIPTION OF EMBODIMENTS

Figure 1:
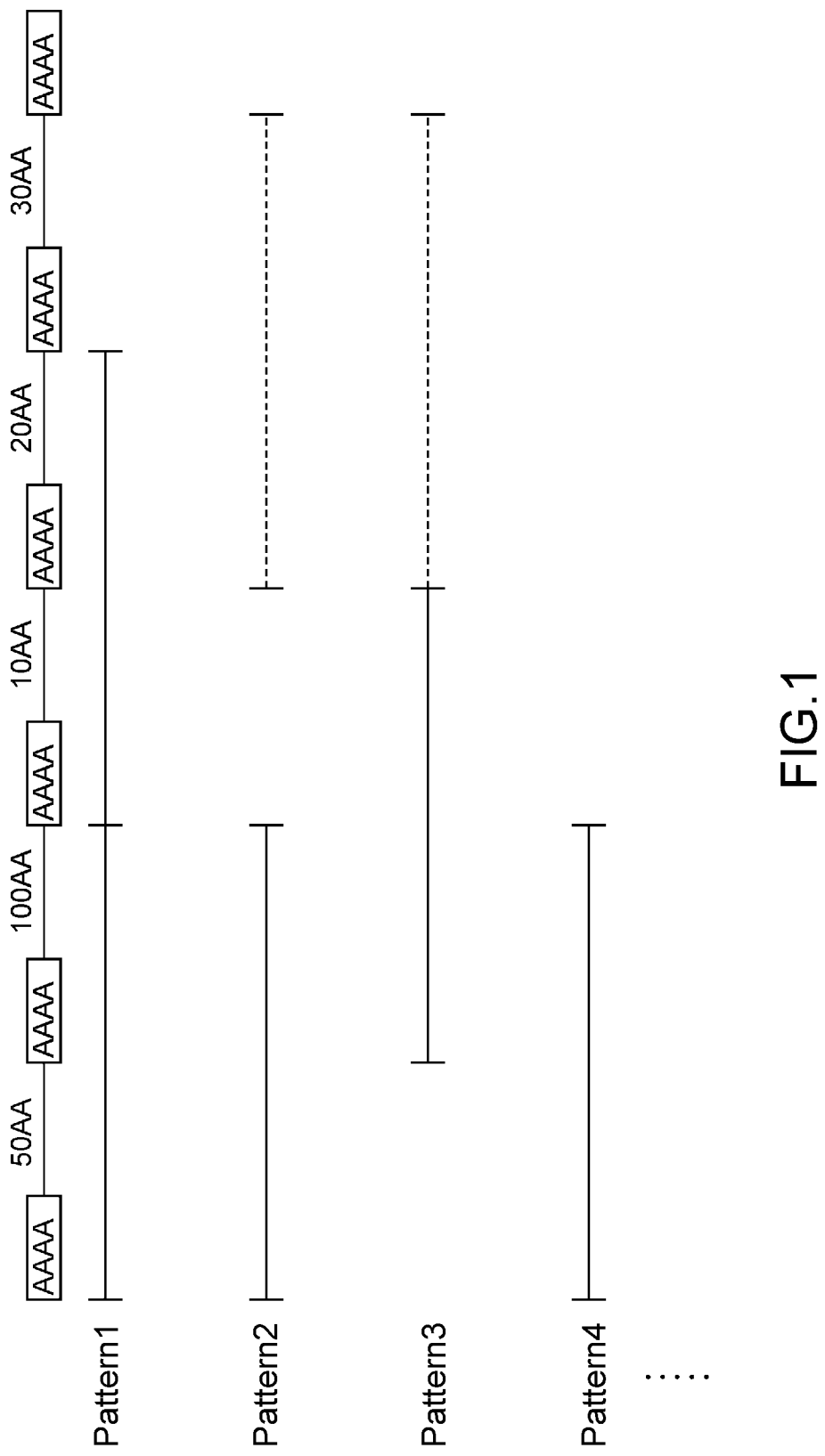
FIG. 1 is a schematic diagram showing a domain sequence of a modified fibroin.

1. Composite molding composition
1-1. Non-drawing composite molding composition

One embodiment of the present invention is a composition containing: a fibroin-derived protein; and a polypeptide and/or a polyamino acid each having a β-sheet structure. Particularly, the composition is a composite molding composition which is a non-drawing composite molding composition as a composition molded by blending the polypeptide and/or the polyamino acid each having the β-sheet structure with a fibroin-derived protein.

A later-described pre-drawn composite molding composition can be produced using this non-drawing composite molding composition.

As an example of the above composite molding composition, the composition may be that maintaining the β-sheet structure derived from the above polypeptide and/or polyamino acid, and selected from a composite fiber, a composite film, a composite gel or a composite molded body.

(1) Fibroin-Derived Protein

Fibroin constitutes silk produced by, for example, insects and spiders, and is known as a collective term of a fibrous protein occupying 70% of such silk. In this specification, "fibroin" includes natural silks produced by insects and spiders; and artificial silks artificially produced by mimicking or targeting the compositions and properties of these natural silks. In this specification, "fibroin" includes spidroin proteins such as the following spidroin I and II; as well as, for example, fibroins derived from silk threads produced by silkworms, other than these fibroins that are derived from spider threads. In addition to natural fibroins, fibroin may also be obtained by a genetic recombination method where, for example, a nucleic acid sequence coding for a desired amino acid sequence is produced, and then incorporated into an expression vector to produce a recombination expression vector by a known method, followed by introducing it into an appropriate host(s) such as bacteria, yeasts, mammal cells, plants and insect cells to produce a transfectant(s), and then performing isolated purification on them before use (e.g. international publication WO 2012/165476). Further, since some of the fibroins are commercially available, they may be acquired and subjected to use.

There are no particular restrictions on the fibroin-derived protein of the present invention. It may be a natural fibroin; or a so-called natural fibroin-derived protein that is produced using a microorganism or the like, or produced by synthesis, with the aid of a genetic recombination technology.

Further, such fibroin-derived protein may be at least one selected from the group consisting of a silk fibroin-derived silk protein (silk fibroin protein), a spider thread fibroin-derived spider thread protein (spider thread fibroin protein) and a hornet silk fibroin-derived hornet silk protein. Among these proteins, a spider thread fibroin-derived spider thread protein is preferably used.

In this specification, "fibroin-derived protein" includes proteins constituting naturally derived fibroins such as those produced by insects and spiders that are described above; and other than these natural proteins, for example, proteins whose structures and properties are analogous to those of proteins that are artificially produced by a genetic recombination method.

Proteins with structures analogous to those of fibroins include a protein(s) whose amino acid sequence resembles that of a natural fibroin by not less than 80%, preferably not less than 85%, more preferably not less than 90% and most preferably not less than 95%; protein segments having partial sequences of these proteins; or fusion proteins of these proteins or protein segments and other proteins or peptides. Further, in this specification, "fibroin-derived protein" may be referred to as "fibroin-derived polypeptide" based on its structural property.

Further, a protein having properties analogous to those of a fibroin is a one such that at least one of the protein's tensile strength, toughness and stretchability as the properties of a natural fibroin is at least not less than 80%, preferably not less than 85%, more preferably not less than 95%, most preferably not less than 100% as excellent as that of a natural fibroin. Further, in this specification, when, for example, describing such structural and physical properties of a fibroin, there may be used terms such as "fibroin-like polypeptide" or "fibroin-like protein."

The following modified fibroin may be used as a fibroin. The modified fibroin is a protein containing a domain sequence represented by a formula (I): $[(A)_n\text{ motif-REP}]_m$. As for the modified fibroin, amino acid sequences (N-terminal sequence and C-terminal sequence) may be further added to any one or both of the N-terminal side and the C-terminal side of the domain sequence. The N-terminal sequence and C-terminal sequence are typically, though not limited to, regions having no repetition of amino acid motifs unique to fibroin, and consisting of about 100 residues of amino acids. The protein containing the domain sequence represented by the formula (I): $[(A)_n\text{ motif-REP}]_m$ is described in detail in PCT/JP2017/016917 and PCT/JP2017/016925, and is incorporated into this specification by citation.

In this specification, "modified fibroin" refers to an artificially produced fibroin (artificial fibroin). A modified fibroin may be a fibroin whose domain sequence differs from the amino acid sequence of a naturally derived fibroin, or a fibroin whose domain sequence is identical to the amino acid sequence of a naturally derived fibroin. The "naturally derived fibroin" in this specification is also a protein containing the domain sequence represented by $[(A)_n\text{ motif-REP}]_m$.

As long as the particular amino acid sequence identified in the present invention is contained, the "modified fibroin" may be that directly employing the amino acid sequence of a naturally derived fibroin; that with its amino acid sequence being modified based on the amino acid sequence of a naturally derived fibroin (e.g. that with its amino acid sequence being modified by modifying the gene sequence of a naturally derived fibroin cloned); or that artificially designed and synthesized without employing a naturally derived fibroin (e.g. that having a desired amino acid sequence as a result of chemically synthesizing a nucleic acid coding for a designed amino acid sequence).

In this specification, "domain sequence" refers to an amino acid sequence generating a crystalline region unique to fibroin (typically, a region corresponding to the $(A)_n$ motif of the amino acid sequence) and a non-crystalline region (typically, a region corresponding to REP of the amino acid sequence), and being represented by the formula (I): $[(A)_n\text{ motif-REP}]_m$. Here, the $(A)_n$ motif represents an amino acid sequence mainly composed of alanine residues, in which n may be an integer of 2 to 20, preferably 4 to 20, more preferably 8 to 20, even more preferably 10 to 20, still even more preferably 4 to 16, further preferably 8 to 16, and especially preferably 10 to 16. Further, a ratio of the number of the alanine residues to the number of all the amino acid residues in the $(A)_n$ motif is not lower than 40%, preferably not lower than 60%, more preferably not lower than 70%, even more preferably not lower than 80%, still even more preferably not lower than 90%, or even 100% (i.e. when only composed of alanine residues). REP represents an amino acid sequence composed of 2 to 200 amino acid residues. m represents an integer of 2 to 300. The multiple $(A)_n$ motifs may be identical amino acid sequences or different amino acid sequences. The multiple REPs may be identical amino acid sequences or different amino acid sequences. Specific examples of a protein derived from a spigot guiding thread include proteins containing, for example, amino acid sequences set forth in SEQ ID NO: 1 to 3 as partial sequences of natural sequences; and amino acid sequences set forth in SEQ ID NO: 4 to 19 as modified natural sequences.

An amino acid sequence (Met-PRT313) set forth in SEQ ID NO: 6 is a sequence prepared by modifying the amino acid residues in the amino acid sequence of *Nephila Clavipes* (GenBank Accession No: P46804. 1, GI: 1174415) as a naturally derived fibroin in a way such that, for example, the number of the successive alanine residues in the [(A)$_n$ motif] region where alanine residues exist in as successive manner is reduced to 5 by deletion. An amino acid sequence (PRT313) set forth in SEQ ID NO: 12 is an amino acid sequence with an amino acid sequence (tag sequence and hinge sequence) set forth in SEQ ID NO: 21 being added to the N-terminal of the amino acid sequence (Met-PRT313) set forth in SEQ ID NO: 6.

An amino acid sequence (Met-PRT399) set forth in SEQ ID NO: 7 is an amino acid sequence prepared by deleting (A)$_n$ motif ((A)$_5$) from the amino acid sequence set forth in SEQ ID NO: 6 in a way such that (A)$_n$ motif ((A)$_5$) is deleted every other two of them from the N-terminal side toward the C-terminal side, and then by inserting one [(A)$_n$ motif-REP] into a region immediately before the C-terminal sequence. An amino acid sequence (PRT399) set forth in SEQ ID NO: 13 is an amino acid sequence with the amino acid sequence (tag sequence and hinge sequence) set forth in SEQ ID NO: 21 being added to the N-terminal of such amino acid sequence set forth in SEQ ID NO: 7.

An amino acid sequence (Met-PRT380) set forth in SEQ ID NO: 8 is an amino acid sequence prepared by substituting all the GGX in the REP of the amino acid sequence set forth in SEQ ID NO: 6 with GQX. An amino acid sequence (PRT380) set forth in SEQ ID NO: 14 is an amino acid sequence with the amino acid sequence (tag sequence and hinge sequence) set forth in SEQ ID NO: 21 being added to the N-terminal of such amino acid sequence set forth in SEQ ID NO: 8.

An amino acid sequence (Met-PRT410) set forth in SEQ ID NO: 9 is an amino acid sequence prepared by substituting all the GGX in the REP of the amino acid sequence set forth in SEQ ID NO: 7 with GQX. An amino acid sequence (PRT410) set forth in SEQ ID NO: 15 is an amino acid sequence with the amino acid sequence (tag sequence and hinge sequence) set forth in SEQ ID NO: 21 being added to the N-terminal of such amino acid sequence set forth in SEQ ID NO: 9.

An amino acid sequence (Met-PRT468) set forth in SEQ ID NO: 10 is an amino acid sequence prepared by inserting two A residues into a poly-A region of the amino acid sequence set forth in SEQ ID NO: 6, deleting two repeating sequences on the C-terminal side, and substituting Q with S or P at 13 locations, in a way such that the sequence will substantially have the same molecular weight as the amino acid sequence set forth in SEQ ID NO: 9. An amino acid sequence (PRT468) set forth in SEQ ID NO: 16 is an amino acid sequence with the amino acid sequence (tag sequence and hinge sequence) set forth in SEQ ID NO: 21 being added to the N-terminal of such amino acid sequence set forth in SEQ ID NO: 10.

An amino acid sequence (Met-PRT799) set forth in SEQ ID NO: 11 is an amino acid sequence prepared by adding the amino acid sequence (tag sequence and hinge sequence) set forth in SEQ ID NO: 21 to several amino acid residues on the C-terminal side of a sequence established by repeating 4 times a region of 20 domain sequences in the amino acid sequence set forth in SEQ ID NO: 9. An amino acid sequence (PRT799) set forth in SEQ ID NO: 17 is an amino acid sequence prepared by adding the amino acid sequence (tag sequence and hinge sequence) set forth in SEQ ID NO: 21 to the N-terminal of the amino acid sequence set forth in SEQ ID NO: 11.

The aforementioned amino acid sequences are summarized as follows.

SEQ ID NO: 1 Amino acid sequence of *Araneus diadematus*
SEQ ID NO: 2 Amino acid sequence of *Araneus diadematus*
SEQ ID NO: 3 Amino acid sequence of *Araneus diadematus*
SEQ ID NO: 4 Amino acid sequence of recombinant spider silk protein ADF3KaiLargeNRSH1
SEQ ID NO: 5 Sequence prepared by deleting a His-tag amino acid sequence from the sequence set forth in SEQ ID NO: 4
SEQ ID NO: 6 Met-PRT313: Amino acid sequence of Met-CRY1_L_A5
SEQ ID NO: 7 Met-PRT399: Amino acid sequence of Met-CRY1_L_A5_giza
SEQ ID NO: 8 Met-PRT380: Amino acid sequence of Met-CRY1_L_A5_QQQ
SEQ ID NO: 9 Met-PRT410: Amino acid sequence of Met-CRY1_L_A5_giza_QQQ
SEQ ID NO: 10 Met-PRT468: Amino acid sequence of Met-CRY1_L_A7_giza_QQQ
SEQ ID NO: 11 Met-PRT799: Amino acid sequence of Met-CRY1_200_A5_giza_QQQ_WHis6
SEQ ID NO: 12 Amino acid sequence of PRT313
SEQ ID NO: 13 Amino acid sequence of PRT399
SEQ ID NO: 14 Amino acid sequence of PRT380
SEQ ID NO: 15 Amino acid sequence of PRT410
SEQ ID NO: 16 Amino acid sequence of PRT468
SEQ ID NO: 17 Amino acid sequence of PRT799
SEQ ID NO: 18 Amino acid sequence of ADF3Kai_noNR
SEQ ID NO: 19 Amino acid sequence prepared by deleting His tag from the amino acid sequence set forth in SEQ ID NO: 18
SEQ ID NO: 20 His-tag and start codon amino acid sequence
SEQ ID NO: 21 His-tag amino acid sequence The modified fibroin may, for example, be obtained by modifying an amino acid sequence equivalent to an amino acid sequence prepared by, for example, substituting, deleting, inserting and/or adding one or more amino acid residues with regard to a gene sequence of a cloned naturally derived fibroin. Amino acid residue substitutions, deletions, insertions and/or additions may be carried out by methods well known to those skilled in the art, such as site-directed mutagenesis. Specifically, it may be carried out according to the methods described in the literatures such as Nucleic Acid Res. 10, 6487 (1982), Methods in Enzymology, 100, 448 (1983).

The naturally derived fibroin is a protein having a domain sequence represented by Formula (I): [(A)$_n$ motif-REP]$_m$, specifically, for example, a fibroin produced by insects or spiders.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta*, and *Antheraea assama*; and Hornet silk proteins discharged by larvae of *Vespa simillima xanthoptera*.

A more specific example of the fibroin produced by insects include a silkworm fibroin L chain (GenBank Accession No. M76430 (nucleotide sequence), AAA27840.1 (amino acid sequence)).

Examples of the fibroin produced by spiders include spider silk proteins (spider thread protein) produced by spiders belonging to the genus *Araneus* such as *Araneus ventricosus*, *Araneus diadematus*, *Araneus pinguis*, *Araneus pentagrammicus* and *Araneus nojima*, spiders belonging to the genus *Neoscona* such as *Neoscona scylla*, *Neoscona nautica*, *Neoscona adianta* and *Neoscona scylloides*, spiders belonging to the genus *Pronus* such as *Pronous minutes*, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena*, *Argiope minuta* and *Argiope bruennich*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis*, *Cyrtophora exanthematica* and *Cyrtophora unicolor*, spiders belonging to the genus *Poltys* such as *Poltys illepidus*, spiders belonging to the genus *Cyclosa* such as *Cyclosa octotuberculata*, *Cyclosa sedeculata*, *Cyclosa vallata* and *Cyclosa atrata*, and spiders belonging to the genus *Chorizopes* such as *Chorizopes nipponicus*; and spider silk proteins produced by spiders belonging to the genus *Tetragnatha* such as *Tetragnatha praedonia*, *Tetragnatha maxillosa*, *Tetragnatha extensa* and *Tetragnatha squamata*, spiders belonging to the genus *Leucauge* such as *Leucauge magnifica*, *Leucauge blanda* and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans*, *Latrodectus hasseltii*, *Latrodectus geometricus* and *Latrodectus tredecimguttatus*, and spiders belonging to the family Tetragnathidae such as spiders belonging to the genus *Euprosthenops*. Examples of spider silk proteins include dragline proteins such as MaSp (MaSp1 and MaSp2) and ADF (ADF3 and ADF4), and MiSp (MiSp1 and MiSp2).

More specific examples of the fibroin produced by spiders include fibroin-3 (adf-3) [derived from *Araneus diadematus*] (GenBank Accession Number AAC47010 (amino acid sequence), U47855 (nucleotide sequence)), fibroin-4 (adf-4) [derived from *Araneus diadematus*] (GenBank Accession Number AAC47011 (amino acid sequence), U47856 (nucleotide sequence)), dragline silk protein spidroin 1 [derived from *Nephila clavipes*] (GenBank Accession Number AAC04504 (amino acid sequence), U37520 (nucleotide sequence)), major angullate spidroin 1 [derived from *Latrodectus hesperus*] (GenBank Accession Number ABR68856 (amino acid sequence)), EF595246 (nucleotide sequence)), dragline silk protein spidroin 2 [derived from *Nephila clavata*] (GenBank Accession Number AAL32472 (amino acid sequence), AF441245 (nucleotide sequence)), major anpullate spidroin 1 [derived from *Euprosthenops australis*] (GenBank Accession Number CAJ00428 (amino acid sequence), AJ973155 (nucleotide sequence)) and major ampullate spidroin 2 [*Euprosthenops australis*] (GenBank Accession Number CAM32249.1 (amino acid sequence), AM490169 (nucleotide sequence)), minor ampullate silk protein 1 [*Nephila clavipes*] (GenBank Accession Number AAC14589.1 (amino acid sequence)), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence).

Fibroins in which sequence information is registered in NCBI GenBank may be further listed as a more specific example of the naturally derived fibroin. For example, these can be identified by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin may be a modified silk fibroin (obtained by altering the amino acid sequence of the silk protein produced by silkworm), and a modified spider thread fibroin (obtained by altering the amino acid sequence of the spider silk protein produced by spiders). Among these fibroins, the modified spider thread fibroin is preferably used.

Specific examples of the modified fibroin include: a modified fibroin derived from the spigot guiding thread protein produced by the major ampullate of a spider [modified fibroin according to the first embodiment]; a modified fibroin with a reduced content of glycine residues [modified fibroin according to the second embodiment]; a modified fibroin with a reduced content of $(A)_n$ motifs [modified fibroin according to the third embodiment]; and a modified fibroin with a reduced content of glycine residues and with a reduced content of $(A)_n$ motifs [modified fibroin according to the fourth embodiment].

The modified fibroin according to the first embodiment may be a protein containing a domain sequence represented by a formula (I): $[(A)_n \text{ motif-REP}]_m$. As for the modified fibroin according to the first embodiment, in the formula (I), n is preferably an integer of 3 to 20, more preferably an integer of 4 to 20, more preferably an integer of 8 to 20, more preferably an integer of 10 to 20, even more preferably an integer of 4 to 16, particularly preferably an integer of 8 to 16, and most preferably an integer of 10 to 16. As for the modified fibroin according to the first embodiment, in the formula (I), the number of amino acid residues constituting the REP is preferably 10 to 200, more preferably 10 to 150, more preferably 20 to 100, and even more preferably 20 to 75 residues. As for the modified fibroin according to the first embodiment, a ratio of the total number of the glycine residues, serine residues and alanine residues contained in the amino acid sequence set forth in the formula (I): $[(A)_n \text{ motif-REP}]_m$ to the total number of amino acid residues is preferably 40% or more, more preferably 60% or more, and even more preferably 70% or more.

The modified fibroin according to the first embodiment may be a polypeptide containing the unit of the amino acid sequence set forth in the formula (I): $[(A)_n \text{ motif-REP}]_m$, where the C-terminal sequence is an amino acid sequence set forth in any one of the SEQ ID NO: 1 to 3, or an amino acid sequence having a homology of 80% or more, preferably 85% or more, more preferably 90% or more, and most preferably 95% or more, with respect to the amino acid sequence set forth in any one of the SEQ ID NO: 1 to 3.

The amino acid sequence set forth in SEQ ID NO: 1 is identical to an amino acid sequence consisting of the 50 amino acid residues at the C-terminal of the amino acid sequence of ADF 3 (GI: 1263287, NCBI); the amino acid sequence set forth in SEQ ID NO: 2 is identical to an amino acid sequence prepared by removing 20 residues from the C-terminal of the amino acid sequence set forth in SEQ ID NO: 1; the amino acid sequence set forth in SEQ ID NO: 3 is identical to an amino acid sequence prepared by removing 29 residues from the C-terminal of the amino acid sequence set forth in SEQ ID NO: 1.

A more specific example of the modified fibroin according to the first embodiment may be a modified fibroin containing (1-i) the amino acid sequence set forth in SEQ ID NO: 4 or SEQ ID NO: 5 (amino acid sequence prepared by removing His-tag from the amino acid sequence of SEQ ID NO: 4); or (1-ii) an amino acid sequence having sequence identity of 80% or more, preferably 85% or more, more preferably 90% or more, and most preferably 95% or more, with respect to the amino acid sequence set forth in SEQ ID NO: 4. Such sequence identity may be 100%.

The amino acid sequence set forth in SEQ ID NO: 4 is prepared as follows. That is, an amino acid sequence of ADF3 prepared by adding to the N-terminal an amino acid sequence (SEQ ID NO: 20) consisting of a start codon, a His10-tag and a HRV3C protease (Human rhinovirus 3C protease) recognition site is mutated in a way such that the 1st to the 13th repeat regions are approximately doubled, and that translation is made to end at the 1154th amino acid residue. The amino acid sequence of the C-terminal of the amino acid sequence set forth in SEQ ID NO: 4 is identical to the amino acid sequence set forth in SEQ ID NO: 8.

The modified fibroin of (1-i) may be that consisting of the amino acid sequence set forth in SEQ ID NO: 4.

As for the modified fibroin according to the second embodiment, the ratio of the motif sequences with the glycine residues being substituted by another amino acid residue(s) to all the motif sequences may be 10% or more.

The modified fibroin according to the second embodiment may be that containing the domain sequence represented by the formula (I): $[(A)_n$ motif-REP$]_m$, and having an amino acid sequence with a ratio of z/w (%) being not lower than 30% or not lower than 50.9%, where z represents a total number of amino acid residues of an amino acid sequence consisting of XGX (provided that X represents an amino acid residue other than glycine) contained in all the REPs in a sequence prepared by removing from the domain sequence a sequence starting from the $(A)_n$ motif closest to the C-terminal side to the C-terminal of the domain sequence; and w represents a total number of amino acid residues in the sequence prepared by removing from the domain sequence the sequence starting from the $(A)_n$ motif closest to the C-terminal side to the C-terminal of the domain sequence. A ratio of the number of the alanine residues to the total number of the amino acid residues in the $(A)_n$ motif may be 83% or more, preferably 86% or more, more preferably 90% or more, more preferably 95% or more, and even more preferably 100% (i.e. consisting only of alanine residues).

In the modified fibroin according to the second embodiment, it is preferable to increase the content ratio of the amino acid sequence consisting of XGX by substituting one glycine residue of the GGX motif with another amino acid residue. In the modified fibroin according to the second embodiment, the content ratio of the amino acid sequence consisting of GGX in the domain sequence is preferably 30% or less, more preferably 20% or less, still more preferably 10% or less, even still more preferably 6% or less, more particularly preferably 4% or less, and most preferably 2% or less. The content ratio of the amino acid sequence consisting of GGX in the domain sequence can be calculated by the same method as the calculation method of the content ratio (z/w) of the amino acid sequence consisting of XGX described below.

The calculation method of z/w will be described in more detail. First, an amino acid sequence consisting of XGX is extracted from all the REPs in the sequence excluding, from the domain sequence, a sequence ranging from the $(A)_n$ motif located at the most C-terminal side to the C-terminal of the domain sequence. The total number of amino acid residues constituting XGX is z. For example, in the case where 50 amino acid sequences consisting of XGX are extracted (there is no overlap), z is 50×3=150. Also, for example, in the case where a common X is contained in two XGXs (central X) such as an amino acid sequence consisting of XGXGX, it is calculated by subtracting the overlapping portion (in the case of XGXGX, it is 5 amino acid residues). w is the total number of amino acid residues contained in the sequence excluding, from the domain sequence, a sequence ranging from the $(A)_n$ motif located at the most C-terminal side to the C-terminal of the domain sequence. For example, in the case of the domain sequence shown in FIG. 1, w is 4+50+4+100+4+10+4+20+4+30=230 (excluding the $(A)_n$ motif located at the most C-terminal side). Next, z/w (%) can be calculated by dividing z by w.

Figure 3:
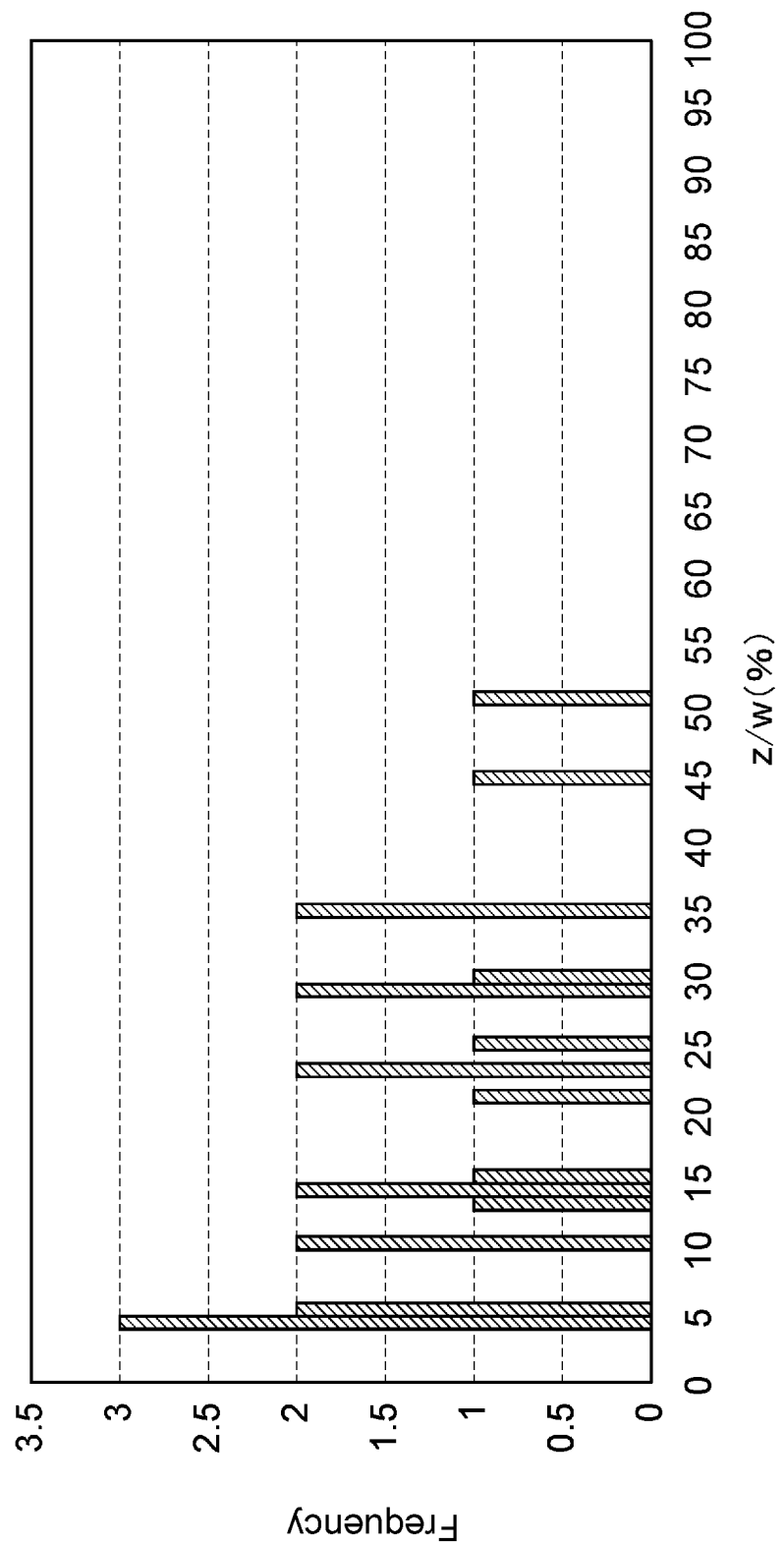
FIG. 3 is a diagram showing a distribution of values of z/w (%) of naturally derived fibroin.

Here, z/w in naturally derived fibroin will be described. First, as described above, 663 types of fibroins (415 types of fibroins derived from spiders among them) were extracted by identifying fibroins with amino acid sequence information registered in NCBI GenBank by a method exemplified. z/w (%) was calculated by the above-mentioned calculation method from the amino acid sequences of naturally derived fibroins consisting of a domain sequence represented by Formula I: $[(A)_n$ motif-REP$]_m$, among all the extracted fibroins where the content ratio of the amino acid sequence consisting of GGX in the fibroin is 6% or less. FIG. 3 shows the results. In FIG. 3, the horizontal axis represents z/w (%) and the vertical axis represents frequency. As is clear from FIG. 3, z/w in naturally derived fibroin is less than 50.9% (highest, 50.86%).

In the modified fibroin according to the second embodiment, z/w is preferably 50.9% or more, more preferably 56.1% or more, still more preferably 58.7% or more, even still more preferably 70% or more, and still further preferably 80% or more. The upper limit of z/w is not particularly limited, but it may be 95% or less, for example.

The modified fibroin according to the second embodiment can be obtained, for example, by substituting and modifying at least a part of a nucleotide sequence encoding a glycine residue from the gene sequence of cloned naturally derived fibroin so as to encode another amino acid residue. At this time, one glycine residue in the GGX motif and GPGXX motif may be selected as the glycine residue to be modified, and substitution may be carried out such that z/w is equal to or more than 50.9%. Alternatively, the modified fibroin can also be obtained, for example, by designing an amino acid sequence satisfying each of the above embodiments from the amino acid sequence of naturally derived fibroin and chemically synthesizing a nucleic acid encoding the designed amino acid sequence. In any case, in addition to the modification, corresponding to the substitution of one glycine residue in the REP with another amino acid residues, to the amino acid sequence of naturally derived fibroin, further modification of the amino acid sequence corresponding to substitution, deletion, insertion and/or addition of one or a plurality of amino acid residues may be carried out.

The above-described alternative amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, among which more preferred are a valine (V) residue, a leucine (L) residue, an isoleucine (I) residue or a glutamine (Q) residue, and still more preferred is a glutamine (Q) residue.

A more specific example of the modified fibroin according to the second embodiment may be a modified fibroin including (2-i) an amino acid sequence set forth in SEQ ID NO: 8, SEQ ID NO: 9, SEQ ID NO: 10 or SEQ ID NO: 11, or (2-ii) an amino acid sequence having 80% or more, preferably 85% or more, more preferably 90% or more, even more preferably 95% or more sequence identity with the amino acid sequence set forth in SEQ ID NO: 8, SEQ ID NO: 9, SEQ ID NO: 10 or SEQ ID NO: 11.

The modified fibroin of (2-i) will be described. The amino acid sequence set forth in SEQ ID NO: 8 is the amino acid sequence in which all GGX in REP of the amino acid sequence set forth in SEQ ID NO: 6, corresponding to naturally derived fibroin, is substituted with GQX. The amino acid sequence set forth in SEQ ID NO: 9 is the amino acid sequence in which $(A)_n$ motif is deleted every other two of them from the amino acid sequence set forth in SEQ ID NO: 8 from the N-terminal side toward the C-terminal side, and further one $[(A)_n$ motif-REP] is inserted before the C-terminal sequence. The amino acid sequence set forth in SEQ ID NO: 10 is the amino acid sequence in which two alanine residues are inserted at the C-terminal side of each $(A)_n$ motif of the amino acid sequence set forth in SEQ ID NO: 9, and a part of glutamine (Q) residues is further substituted with a serine (S) residue, and then a part of amino acids on the N-terminal side is deleted so as to have almost the same molecular weight as the molecular weight of SEQ ID NO: 9. The amino acid sequence represented by SEQ ID NO.11 is an amino acid sequence prepared by adding His tag to the C-terminal of a sequence established by repeating 4 times a region of 20 domain sequences in the amino acid sequence set forth in SEQ ID NO.10 (Note that several amino acid residues at the C-terminal side of the region are substituted).

The value of z/w (%) of the amino acid sequence set forth in SEQ ID NO: 6 (corresponding to naturally derived fibroin) is 46.8%. The values of z/w in the amino acid sequences set forth in SEQ ID NO: 8, 9, 10 and 11 are 58.7%, 70.1%, 66.1% and 70.0%, respectively. The value of x/y at Giza ratio 1:1.8 to 1:11.3 of the amino acid sequence set forth in SEQ ID NO 6, 8, 9, 10 and 11 are 15.0%, 15.0%, 93.4%, 92.7% and 89.3%, respectively.

The modified fibroin of (2-i) may consist of the amino acid sequence set forth in SEQ ID NO: 8, SEQ ID NO: 9, SEQ ID NO: 10, or SEQ ID NO: 11.

The modified fibroin of (2-ii) includes an amino acid sequence having a sequence identity of 80% or more, preferably 85% or more, more preferably 90% or more, and still more preferably 95% or more, with respect to the amino acid sequence set forth in SEQ ID NO: 8, SEQ ID NO: 9, SEQ ID NO: 10 or SEQ ID NO: 11. The modified fibroin of (2-ii) is also a protein having a domain sequence represented by Formula I: $[(A)_n$ motif-REP$]_m$. The sequence identity is 80% or more, preferably 85% or more, more preferably 90% or more and still more preferably 95% or more.

It is preferred that the modified fibroin of (2-ii) has a sequence identity of 80% or more, preferably 85% or more, more preferably 90% or more, and still more preferably 95% or more, with respect to the amino acid sequence set forth in SEQ ID NO:8, SEQ ID NO: 9, SEQ ID NO: 10 or SEQ ID NO: 11, and z/w is preferably 50.9% or more where the total number of amino acid residues in the amino acid sequence consisting of XGX (where X represents an amino acid residue other than glycine) contained in the REP is defined as z, and the total number of amino acid residues in the REP in the domain sequence is w.

The above-mentioned modified fibroin may include a tag sequence at either or both of the N-terminal and C-terminal. This makes it possible to isolate, immobilize, detect and visualize the modified fibroin.

The tag sequence may be, for example, an affinity tag utilizing a specific affinity (binding property, affinity) with another molecule. The specific example of the affinity tag includes a histidine tag (His tag). His tag is a short peptide in which about 4 to 10 histidine residues are arranged. His tag has a property of specifically binding to a metal ion such as nickel, so it can be used for isolation of a modified fibroin by chelating metal chromatography. A specific example of the tag sequence includes, for example, an amino acid sequence set forth in SEQ ID NO: 21 (amino acid sequence including His tag).

In addition, a tag sequence such as glutathione-S-transferase (GST) that specifically binds to glutathione or maltose binding protein (MBP) that specifically binds to maltose can also be used.

Further, an "epitope tag" utilizing the antigen-antibody reaction can also be used. A peptide (epitope), exhibiting antigenicity as a tag sequence, may be added to bind an antibody against the epitope. Examples of the epitope tag include an HA (peptide sequence of hemagglutinin of influenza virus) tag, a myc tag, and a FLAG tag. The modified fibroin can easily be purified with high specificity by utilizing the epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including a tag sequence may be a modified fibroin including (2-iii) an amino acid sequence set forth in SEQ ID NO: 14, SEQ ID NO: 15, SEQ ID NO: 16 or SEQ ID NO: 17, or (2-iv) an amino acid sequence having a sequence identity of 80% or more, preferably 85% or more, more preferably 90% or more, and still more preferably 95% or more, with respect to the amino acid sequence set forth in SEQ ID NO: 14, SEQ ID NO: 15, SEQ ID NO: 16 or SEQ ID NO: 17.

The amino acid sequences set forth in SEQ ID NOs: 12, 13, 14, 15, 16 and 17 are amino acid sequences in which an amino acid sequence set forth in SEQ ID NO: 21 (including a His tag) is added to at the N-terminals of the amino acid sequences set forth in SEQ ID NOs: 6, 7, 8, 9, 10 and 11, respectively.

The modified fibroin of (2-iii) may consist of an amino acid sequence set forth in SEQ ID NO: 14, SEQ ID NO: 15, SEQ ID NO: 16 or SEQ ID NO: 17.

The modified fibroin of (2-iv) includes an amino acid sequence having a sequence identity of 80% or more, preferably 85% or more, more preferably 90% or more and, most more preferably 95% or more, with respect to the amino acid sequence set forth in SEQ ID NO: 14, SEQ ID NO: 15, SEQ ID NO: 16 or SEQ ID NO: 17. The modified fibroin of (2-iv) is also a protein having a domain sequence represented by Formula (I): $[(A)_n\ motif\text{-}REP]_m$. The sequence identity is 80% or more, preferably 85% or more, more preferably 90% or more and still more preferably 95% or more.

It is preferred that the modified fibroin of (2-iv) has a sequence identity of 80% or more, preferably 85% or more, more preferably 90% or more, and still more preferably 95% or more, with respect to the amino acid sequence set forth in SEQ ID NO: 14, SEQ ID NO: 15, SEQ ID NO: 16 or SEQ ID NO: 17, and z/w (%) is preferably 50.9% or more where the total number of amino acid residues in the amino acid sequence consisting of XGX (where X represents an amino acid residue other than glycine) contained in the REPs is defined as z, and the total number of amino acid residues in the REPs in the domain sequence is w.

The above-mentioned modified fibroin may include a secretory signal for releasing the protein produced in the recombinant protein production system to the outside of the host. The sequence of the secretory signal can be appropriately set depending on the type of the host.

The modified fibroin according to the third embodiment has an amino acid sequence whose domain sequence has a content in which the $(A)_n$ motif is reduced as compared to naturally derived fibroins. The domain sequence of the modified fibroin can have an amino acid sequence equivalent to an amino acid sequence in which, at least, one or a plurality of the $(A)_n$ motifs is deleted, as compared to the naturally derived fibroin.

The modified fibroin according to the third embodiment may be, for example, a modified fibroin having an amino acid sequence equivalent to an amino acid sequence in which 10 to 40% of the $(A)_n$ motif is deleted from the naturally derived fibroin.

In the modified fibroin according to the third embodiment, the domain sequence preferably may have an amino acid sequence equivalent to an amino acid sequence in which, at least, one $(A)_n$ motif per one to three $(A)_n$ motifs is deleted from the N-terminal side to the C-terminal side, as compared to the naturally derived fibroin.

In the modified fibroin according to the third embodiment, the domain sequence preferably may have an amino acid sequence equivalent to an amino acid sequence in which at least two consecutive $(A)_n$ motif deletions and one $(A)_n$ motif deletion are repeated in this order from the N-terminal side to the C-terminal side, as compared to the naturally derived fibroin.

In the modified fibroin according to the third embodiment, the domain sequence preferably may have an amino acid sequence equivalent to an amino acid sequence in which at least $(A)_n$ motif is deleted every other two of them from the N-terminal side to the C-terminal side.

The modified fibroin according to the third embodiment may include a domain sequence represented by Formula I: $[(A)_n\ motif\text{-}REP]_m$, and have an amino acid sequence in which x/y is 20% or more or have an amino acid sequence in which x/y is 50% or more, in which x represents a value obtained by sequentially comparing the number of amino acid residues in REPs of two adjacent $[(A)_n\ motif\text{-}REP]$ units from the N-terminal side to the C-terminal side, and then adding together the numbers of amino acid residues in all pairs of adjacent $[(A)_n\ motif\text{-}REP]$ units which are identified as those where when the number of amino acid residues in an REP having a smaller number of amino acid residues is defined as 1, a ratio of the number of amino acid residues in the other REP thereto is 2 to 3.5; and y represents a total number of amino acid residues in the domain sequence. The $(A)_n$ motif may be such that the number of alanine residues, relative to the total number of amino acid residues in the $(A)_n$ motif, is 83% or more, preferably 86% or more, more preferably 90% or more, still more preferably 95% or more, and even still more preferably 100% (which means that the $(A)_n$ motif consists only of alanine residues).

A method of calculating x/y will be described in more detail with reference to FIG. 1. FIG. 1 shows a domain sequence excluding N-terminal sequence and C-terminal sequence from the modified fibroin. This domain sequence has, from the N-terminal side (left side), a sequence of: $(A)_n$ motif-first REP (50 amino acid residues)—$(A)_n$ motif—second REP (100 amino acid residues)—$(A)_n$ motif—third REP (10 amino acid residues)—$(A)_n$ motif-fourth REP (20 amino acid residues)—$(A)_n$ motif—fifth REP (30 amino acid residues)—$(A)_n$ motif.

The two adjacent $[(A)_n\ motif\text{-}REP]$ units are sequentially selected from the N-terminal side to the C-terminal side so as not to overlap. At this time, there may exist an unselected $[(A)_n\ motif\text{-}REP]$. FIG. 1 shows pattern 1 (a comparison between first REP and second REP, and a comparison between third REP and fourth REP), pattern 2 (a comparison between the first REP and the second REP, and a comparison between the fourth REP and the fifth REP), pattern 3 (a comparison between the second REP and the third REP, and a comparison between the fourth REP and the fifth REP), and pattern 4 (a comparison between the first REP and the second REP). Alternative selection methods other than this method may be taken.

Next, for each of the patterns, the number of amino acid residues of each REP in the selected pair of adjacent $[(A)_n\ motif\text{-}REP]$ units is compared. The comparison is carried out by obtaining a ratio of the number of amino acid residues of one REP to the other REP having a smaller number of amino acid residues where the number of amino acid residues in the other REP of smaller number is scaled to 1. For example, in the case of comparing the first REP (50 amino acid residues) and the second REP (100 amino acid residues), the ratio of the number of amino acid residues of the second REP to the first REP having a smaller number of amino acid residues is 100/50=2 where the number of amino acid residues in the first REP, having a smaller number of amino acid residues, is scaled to 1. Similarly, in the case of comparing the fourth REP (20 amino acid residues) and the fifth REP (30 amino acid residues), the ratio of the number of amino acid residues of the fifth REP to the fourth REP having a smaller number of amino acid residues is 30/20=1.5 where the number of amino acid residues in the fourth REP having a smaller number of amino acid residues is scaled to 1.

In FIG. 1, all pairs of $[(A)_n\ motif\text{-}REP]$ units in which the ratio of the number of amino acid residues of one REP to that of the other REP is 1.8 to 11.3 where the other REP having smaller number of amino acid residues is scaled to 1 are indicated by solid lines. Such a ratio is referred to herein as a Giza ratio. All pairs of $[(A)_n\ motif\text{-}REP]$ units in which the ratio of the number of amino acid residues of one REP to that of the other REP is less than 1.8 or more than 11.3 where the other REP having smaller number of amino acid residues is scaled to 1 is indicated by a broken line.

In each pattern, the number of all amino acid residues of the pair of adjacent $[(A)_n\ motif\text{-}REP]$ units indicated by solid lines (including not only the number of amino acid residues of REP but also the number of amino acid residues of $(A)_n$ motif) is all summed up. Then, the total summation values for the patterns are compared to each other, and the total summation value of the pattern taking the maximum (the maximum value of the total value) is defined as x. In the example shown in FIG. 1, the total value of the pattern 1 takes the maximum.

x/y (%) can then be calculated by dividing x by the total amino acid residue number y in the domain sequence.

In the modified fibroin according to the third embodiment, x/y is preferably 50% or more, more preferably 60% or more, still more preferably 65% or more, even still more preferably 70% or more, even further preferably 75% or more, and particularly preferably 80% or more. The upper limit of x/y is not particularly limited, and may be, for example, 100% or less. In the case where the Giza ratio is 1:1.9 to 11.3, x/y is preferably 89.6% or more; in the case where the Giza ratio is 1:1.8 to 3.4, x/y is preferably 77.1% or more; in the case where the Giza ratio is 1:1.9 to 8.4, x/y is preferably 75.9% or more; and in the case where the Giza ratio is 1:1.9 to 4.1, x/y is preferably 64.2% or more.

In the case where the modified fibroin according to the third embodiment is a modified fibroin in which at least seven of the plurality of the $(A)_n$ motifs in the domain sequence consist only of alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited, and it may be 100% or less.

Figure 2:
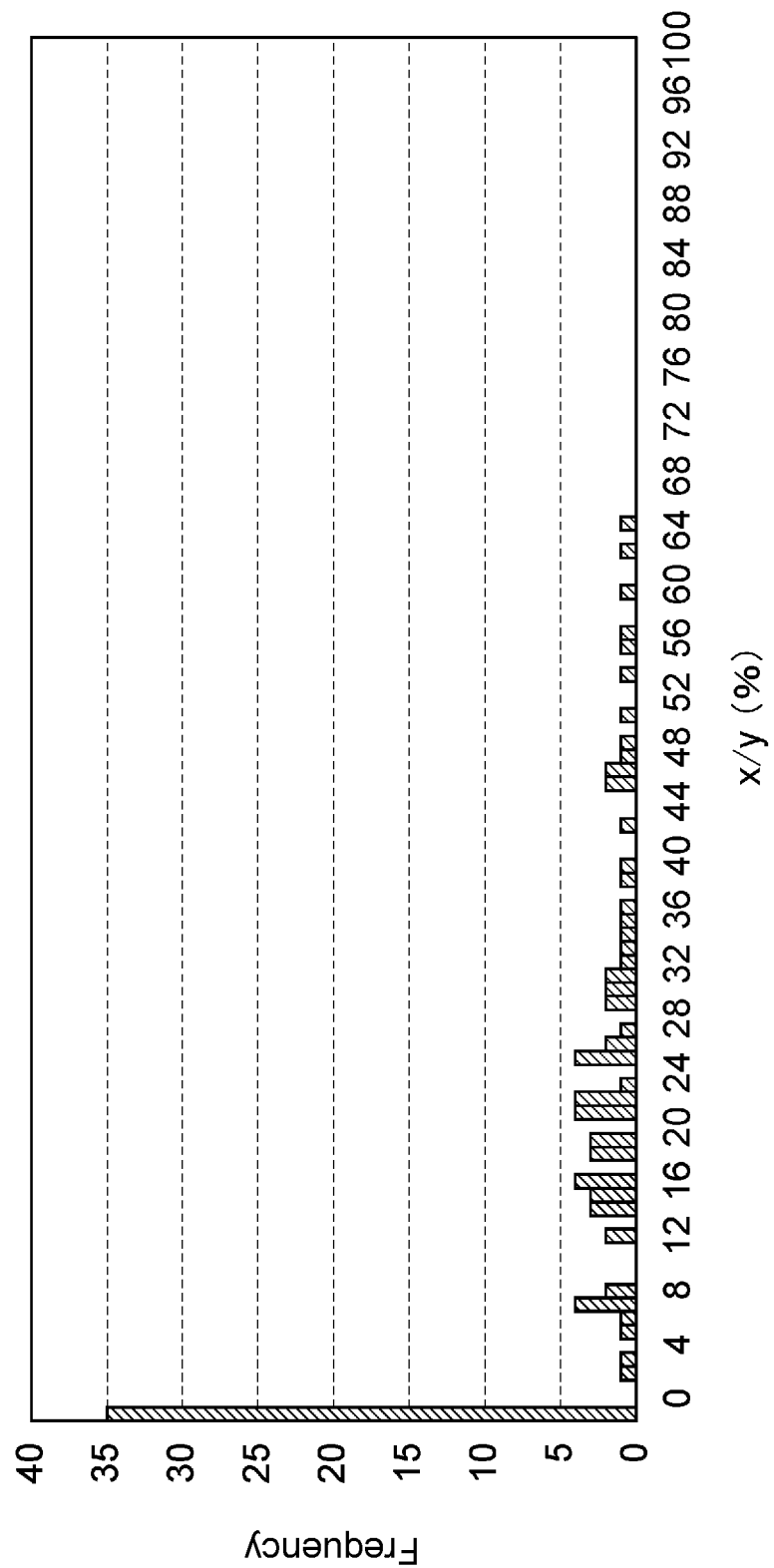
FIG. 2 is a diagram showing a distribution of values of x/y (%) of naturally derived fibroin.

Here, x/y in the naturally derived fibroin will be described. First, as described above, 663 types of fibroins (415 types of fibroins derived from spiders among them) were extracted by identifying fibroins with amino acid sequence information registered in NCBI GenBank by the method exemplified. x/y was calculated by the above-mentioned calculation method from the amino acid sequences of the naturally derived fibroins consisting of a domain sequence represented by Formula I: $[(A)_n$ motif-REP$]_m$, among all the extracted fibroins. FIG. 2 shows the results in the case where the Giza ratio is 1:1.9 to 1:4.1.

In FIG. 2, the horizontal axis represents x/y (%) and the vertical axis represents frequency. As is clear from FIG. 2, x/y in the naturally derived fibroin is less than 64.2% (highest, 64.14%).

The modified fibroin according to the third embodiment may be obtained, for example, from a gene sequence of a cloned naturally derived fibroin, by deleting one or a plurality of the sequences encoding the $(A)_n$ motif such that the percentage of x/y is 64.2% or more. Further, the modified fibroin according to the present embodiment may also be obtained, for example, by designing an amino acid sequence corresponding to the deletion of one or a plurality of $(A)_n$ motifs from the amino acid sequence of the naturally derived fibroin such that x/y is 64.2% or more, and chemically synthesizing a nucleic acid encoding the designed amino acid sequence. In any case, in addition to the modification corresponding to the deletion of the $(A)_n$ motif from the amino acid sequence of the naturally derived fibroin, further modification of the amino acid sequence corresponding to the substitution, deletion, insertion and/or addition of one or a plurality of amino acid residues may be carried out.

A more specific example of the modified fibroin according to the third embodiment may be a modified fibroin including (3-i) an amino acid sequence set forth in SEQ ID NO: 7, SEQ ID NO: 9, SEQ ID NO: 10 or SEQ ID NO: 11, or (3-ii) an amino acid sequence having a sequence identity of 80% or more, preferably 85% or more, more preferably 90% or more, most preferably 95% or more, with respect to the amino acid sequence set forth in SEQ ID NO:7, SEQ ID NO: 9, SEQ ID NO: 10 or SEQ ID NO: 11.

The modified fibroin of (3-i) will be described. The amino acid sequence set forth in SEQ ID NO: 7 is the amino acid sequence in which $(A)_n$ motif is deleted every other two of them from the amino acid sequence set forth in SEQ ID NO: 6, corresponding to the naturally derived fibroin, from the N-terminal side to the C-terminal side, and further one [(A)$_n$ motif-REP] is inserted before the C-terminal sequence. The amino acid sequence set forth in SEQ ID NO: 9 is the amino acid sequence in which all GGX in REP of the amino acid sequence set forth in SEQ ID NO: 7 is substituted with GQX. The amino acid sequence set forth in SEQ ID NO: 10 is the amino acid sequence in which two alanine residues are inserted at the C-terminal side of each $(A)_n$ motif of the amino acid sequence set forth in SEQ ID NO: 9, and further a part of glutamine (Q) residues is substituted with a serine (S) residue, and a part of amino acids on the N-terminal side is deleted so as to be almost the same molecular weight as that of SEQ ID NO: 9. The amino acid sequence represented by SEQ ID NO: 11 is an amino acid sequence prepared by adding His tag to the C-terminal of a sequence established by repeating 4 times a region of 20 domain sequences in the amino acid sequence set forth in SEQ ID NO: 10 (note that several amino acid residues at the C-terminal side of the region are substituted).

The value of x/y % at Giza ratio 1:1.8 to 11.3 of the amino acid sequence set forth in SEQ ID NO: 6 (corresponding to the naturally derived fibroin) is 15.0%. The values of x/y % in the amino acid sequence set forth in SEQ ID NO: 7 and the amino acid sequence set forth in SEQ ID NO: 9 are all 93.4%. The value of x/y in the amino acid sequence set forth in SEQ ID NO: 10 is 92.7%. The value of x/y in the amino acid sequence set forth in SEQ ID NO: 11 is 89.3%. The values of x/y in the amino acid sequences set forth in SEQ ID NOs: 6, 7, 9, 10 and 11 to 12 are 46.8%, 56.2%, 70.1%, 66.1% and 70.0%, respectively.

The modified fibroin of (3-i) may consist of the amino acid sequence set forth in SEQ ID NO: 7, SEQ ID NO: 9, SEQ ID NO: 10 or SEQ ID NO: 11.

The modified fibroin of (3-ii) includes an amino acid sequence having a sequence of identity of 80% or more, preferably 85% or more, more preferably 90% or more, and still more preferably 95% or more, with respect to the amino acid sequence set forth in SEQ ID NO:7, SEQ ID NO:9, SEQ ID NO: 10 or SEQ ID NO: 11. The modified fibroin of (3-ii) is also a protein having a domain sequence represented by Formula I: $[(A)_n$ motif-REP$]_m$. The sequence identity is 80% or more, preferably 85% or more, more preferably 90% or more and most preferably 95% or more.

It is preferred that the modified fibroin of (3-ii) has a sequence identity of 80% or more, preferably 85% or more, more preferably 90% or more, and most preferably 95% or more, with respect to the amino acid sequence set forth in SEQ ID NO: 7, SEQ ID NO: 9, SEQ ID NO: 10 or SEQ ID NO: 11, and that the percentage of x/y is 64.2% or more in which x represents a value obtained by sequentially comparing the number of amino acid residues in REPs of two adjacent [(A)$_n$ motif-REP] units from the N-terminal side to the C-terminal side, and then adding together the numbers of amino acid residues in all pairs of adjacent [(A)$_n$ motif-REP] units which are identified as those where when the number of amino acid residues in an REP having a smaller number of amino acid residues is defined as 1, a ratio of the number of amino acid residues in the other REP thereto is 1.8 to 11.3 (Giza ratio is 1:1.8 to 1:11.3); and y represents a total number of amino acid residues in the domain sequence.

The above-mentioned modified fibroin may include the tag sequence as described at either or both of the N-terminal and C-terminal.

A more specific example of the modified fibroin including a tag sequence may be a modified fibroin including (3-iii) an amino acid sequence set forth in SEQ ID NO: 13, SEQ ID NO: 15, SEQ ID NO: 16 or SEQ ID NO: 17, or (3-iv) an amino acid sequence having a sequence identity of 80% or more, preferably 85% or more, more preferably 90% or more, and most preferably 95% or more, with respect to the amino acid sequence set forth in SEQ ID NO: 13, SEQ ID NO: 15, SEQ ID NO: 16 or SEQ ID NO: 17.

The amino acid sequences set forth in SEQ ID NOs: 12, 13, 14, 15, 16 and 17 are amino acid sequences in which an amino acid sequence set forth in SEQ ID NO: 21 (including His tag) is added at the N-terminals of the amino acid sequences set forth in SEQ ID NOs: 6, 7, 8, 9, 10 and 11, respectively.

The modified fibroin of (3-iii) may consist of the amino acid sequence set forth in SEQ ID NO: 13, SEQ ID NO: 15, SEQ ID NO: 16 or SEQ ID NO: 17.

The modified fibroin of (3-iv) includes an amino acid sequence having a sequence of identity of 80% or more, preferably 85% or more, more preferably 90% or more, and most preferably 95% or more, with respect to the amino acid sequence set forth in SEQ ID NO: 13, SEQ ID NO: 15, SEQ ID NO: 16 or SEQ ID NO: 17. The modified fibroin of (3-iv) is also a protein having a domain sequence represented by Formula I: $[(A)_n$ motif-REP$]_m$. The sequence identity is preferably 95% or more.

It is preferred that the modified fibroin of (3-iv) has a sequence identity of 80% or more, preferably 85% or more, more preferably 90% or more, and most preferably 95% or more, with respect to the amino acid sequence set forth in SEQ ID NO: 13, SEQ ID NO: 15, SEQ ID NO: 16 or SEQ ID NO: 17, and that x/y is 64.2% or more in which x represents the maximum value obtained by sequentially comparing the number of amino acid residues in REPs of two adjacent $[(A)_n$ motif-REP] units from the N-terminal side to the C-terminal side, and then adding together the numbers of amino acid residues in all pairs of adjacent $[(A)_n$ motif-REP] units which are identified as those where when the number of amino acid residues in an REP having a smaller number of amino acid residues is defined as 1, a ratio of the number of amino acid residues in the other REP thereto is 1.8 to 11.3 (Giza ratio is 1:1.8 to 1:11.3), and the total number of amino acid residues of the domain sequence is defined as y.

The above-mentioned modified fibroin may include a secretory signal for releasing the protein produced in the recombinant protein production system to the outside of a host. The sequence of the secretory signal can be appropriately set depending on the type of the host.

In the modified fibroin of the fourth embodiment, the domain sequence has an amino acid sequence in which the content of glycine residues is reduced in addition to having a reduced content of the $(A)_n$ motif as compared to the naturally derived fibroin. The domain sequence of the modified fibroin can have an amino acid sequence equivalent to an amino acid sequence in which one or a plurality of glycine residues in REP is substituted with another amino acid residue, as well as at least one or a plurality of $(A)_n$ motifs is deleted, as compared to the naturally derived fibroin. That is, the modified fibroin has features of the modified fibroin according to both the second and third embodiments. The specific embodiments thereof are as described in the second and third embodiments.

A more specific example of the modified fibroin according to the fourth embodiment may be a modified fibroin including (4-i) an amino acid sequence set forth in SEQ ID NO: 9, SEQ ID NO: 10 or SEQ ID NO: 11, or (4-ii) an amino acid sequence having a sequence identity of 80% or more, preferably 85% or more, more preferably 90% or more, and most preferably 95% or more, with respect to the amino acid sequence set forth in SEQ ID NO: 9, SEQ ID NO: 10 or SEQ ID NO: 11. The specific embodiments of the modified fibroin including the amino acid sequence set forth in SEQ ID NO: 9, SEQ ID NO: 10 or SEQ ID NO: 11 are as described above.

<Method for Producing Protein>

The protein according to the present embodiment can, for example, be produced by employing a host transformed with an expression vector having a nucleic acid sequence encoding the protein and one or more regulatory sequences operably linked to such nucleic acid sequence, and then expressing the nucleic acid.

A method for producing the nucleic acid encoding the protein is not particularly limited. For example, the nucleic acid can be produced by a method of employing a gene encoding a natural fibroin to perform amplification and cloning via a polymerase chain reaction (PCR), and then carry out modification via genetic engineering techniques; or a method of chemically synthesizing the same. The chemical synthesis method of the nucleic acid is also not particularly limited. For example, based on the amino acid sequence information of a protein obtained from a web database etc. such as NCBI, a gene can be chemically synthesized by a method of linking, via PCR or the like, an oligonucleotide automatically synthesized with, for example, AKTA oligopilot plus 10/100 (GE Healthcare Japan Co., Ltd.). At that time, in order to facilitate the purification and/or confirmation of the protein, there may also be synthesized a nucleic acid encoding a protein consisting of an amino acid sequence prepared by adding to the N-terminal of the above amino acid sequence an amino acid sequence consisting of a start codon and a His10-tag.

The regulatory sequence is a sequence (for example, a promoter, an enhancer, a ribosome binding sequence, or a transcription termination sequence) that controls the expression of a modified fibroin in a host, and can be appropriately selected depending on the type of the host. As a promoter, there may be used an inducible promoter functioning in a host cell, and capable of expressing and inducing a modified fibroin. The inducible promoter is a promoter capable of controlling transcription due to the presence of an inducer (expression inducing agent), the non-presence of a repressor molecule, or physical factors such as an increase or decrease in temperature, osmotic pressure or pH value.

The type of the expression vector such as a plasmid vector, a viral vector, a cosmid vector, a fosmid vector, or an artificial chromosome vector may be appropriately selected depending on the type of the host. As such expression vector, an expression vector which can autonomously replicate in a host cell or can be incorporated into a chromosome of a host and which contains a promoter at a position capable of transcribing the nucleic acid encoding the protein is suitably used.

Both the prokaryotes and the eukaryotes such as yeast, filamentous fungi, insect cells, animal cells, and plant cells may be suitably used as hosts.

Preferred examples of the prokaryote include microorganisms belonging to the genus *Escherichia, Brevibacillus, Serratia, Bacillus, Microbacterium, Brevibacterium, Corynebacterium* and *Pseudomonas*. Examples of the microorganisms belonging to the genus *Escherichia* include *Escherichia coli*. Examples of the microorganisms belonging to the genus *Brevibacillus* include *Brevibacillus agri*. Examples of the microorganisms belonging to the genus *Serratia* include *Serratia liquefaciens*. Examples of the microorganisms belonging to the genus *Bacillus* include *Bacillus subtilis*. Examples of the microorganisms belonging to the genus *Microbacterium* include *Microbacterium ammoniaphilum*. Examples of the microorganisms belonging to the genus *Brevibacterium* include *Brevibacterium divaricatum*. Examples of the microorganisms belonging to the genus *Corynebacterium* include *Corynebacterium ammoniagenes*. Examples of the microorganisms belonging to the genus *Pseudomonas* include *Pseudomonas putida*.

If the host is a prokaryote, the vector for introducing a nucleic acid encoding the protein may include, for example, pBTrp2(Boehringer Ingelheim GmbH), pGEX(Pharmacia), pUC18, pBluescriptll, pSupex, pET22b, pCold, pUB110, pNCO2 (Japasese Unexamined Patent Application Publication NO. 2002-238569)

Examples of the eukaryotic hosts include yeast, filamentous fungi (mold and the like), and insect cells. Examples of the yeast include yeasts belonging to the genus *Saccharomyces, Pichia, Schizosaccharomyces*, and the like. Examples of the filamentous fungi include fungi belonging to the genus *Aspergillus, Trichoderma* and *Penicillium*.

If the host is a eucaryote, the vector for introducing a nucleic acid encoding the modified protein may include, for example, YEP13 (ATCC37115) and YEp24 (ATCC37051). As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], electroporation technique, spheroplast technique, protoplast, a technique using lithium acetate, and competent method or the like.

As for the expression method of the nucleic acid by means of the host transformed with the expression vector, secretory production, fusion protein expression, or the like, in addition to the direct expression, can be carried out according to the method described in Molecular Cloning, 2nd edition.

The protein can be produced, for example, by culturing a host transformed with the expression vector in a culture medium, producing and accumulating the protein in the culture medium, and then collecting the protein from the culture medium. The method for culturing the host in the culture medium can be carried out according to the method commonly used for culturing a host.

In the case where the host is a prokaryote such as *Escherichia coli* or a eukaryote such as yeast, any of a natural medium and a synthetic medium may be used as a culture medium of the host as long as it contains a carbon source, a nitrogen source, inorganic salts and the like which can be assimilated by the host and it is capable of efficiently culturing the host.

As the carbon source, any carbon source that can be assimilated by the transformed microorganism may be used. Examples of the carbon source that can be used include carbohydrates such as glucose, fructose, sucrose, and molasses containing them, carbohydrates such as starch and starch hydrolyzates, organic acids such as acetic acid and propionic acid, and alcohols such as ethanol and propanol. Examples of the nitrogen source that can be used include ammonium salts of inorganic or organic acids such as ammonia, ammonium chloride, ammonium sulfate, ammonium acetate and ammonium phosphate, other nitrogen-containing compounds, as well as peptone, meat extract, yeast extract, corn steep liquor, casein hydrolyzate, soybean cake and soybean cake hydrolyzate, various fermented microbial cells and digested products thereof. Examples of the inorganic salt that can be used include potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium at 3.0 to 9.0 during the culture. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-p-D-thiogalactopyranoside or the like is used, and in the case of culturing a microorganism transformed with an expression vector using a trp promoter, indole acrylic acid or the like may be added to the medium.

The modified protein can be isolated and purified by a method commonly used. For example, in the case where the protein is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), an cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In the case where the protein is expressed by the formation of an insoluble matter in the cell, similarly, the host cells are recovered, disrupted and centrifuged to recover the insoluble matter of the protein as a precipitated fraction. The recovered insoluble matter of the protein can be solubilized with a protein denaturing agent. After this operation, a purified preparation of protein can be obtained by the same isolation and purification method a s described above. In the case where a protein is secreted extracellularly, the protein can be recovered from the culture supernatant. That is, a culture supernatant is obtained by treating the culture by a technique such as centrifugation, and a purified preparation can be obtained from the culture supernatant by using the same isolation and purification method as described above.

(2) Polypeptide and Polyamino Acid Having β-Sheet Structure

In the composite molding composition of the present invention, the above embodiment is to add a polypeptide or a polyamino acid each having a β-sheet structure. In this case, polyalanine may be listed as an example of the polyamino acid.

The polyalanine can be selected from a linear polyalanine (L-polyAla) or a telechelic polyalanine (T-polyAla). The linear polyalanine can be produced by an enzyme chemical polymerization method, and produced and used based on a known literature (Baker P J et al., Biomacromolecules 2012, 13, 947-951). Moreover, as described in the following working examples, the telechelic polyalanine can be produced by an enzyme chemical polymerization method, which is also described in Tsuchiya K et al, Macromol. Biosci. 2016, 1001-1008, and is incorporated into this specification as a citation.

(3) Production of Composite Molding Composition Containing Fibroin; and Polypeptide and/or Polyamino Acid Having β-Sheet Structure In this specification, "polypeptide having a β-sheet structure" herein refers to any polypeptide having a β-sheet structure in its two-dimensional structure. Such polypeptide may include both natural and artificially produced polypeptide, where an artificially produced polypeptide is preferred, and a polypeptide having the following sequence of polyamino acid is more preferred.

In this specification, a "polyamino acid" herein refers to an amino acid polymer of a high molecular weight that is obtained via one step of a polymerization reaction while using an amino acid or a derivative thereof as a monomer.

Further, a polyamino acid having a β-sheet structure herein refers to any polyamino acid that is artificially produced and is a polymer of L- or D-amino acid having a β-sheet structure in its two-dimensional structure. Preferable examples of such polyamino acid include homopolyamino acids and derivatives thereof that are selected from polyalanine, polyphenylalanine, polycysteine, polyvaline, polyleucine, polyisoleucine, polytyrosine, polytryptophan, polyglutamine, polymethionine and their derivatives. Other than these homopolyamino acids and their derivatives, there may also be employed polyamino acids consisting of copolymers of multiple kinds, preferably 2 to 5 kinds, more preferably 2 to 4 kinds, and even more preferably 2 or 3 kinds of amino acids that are selected from amino acids such as alanine, phenylalanine, cysteine, valine, leucine, isoleucine, tyrosine, tryptophan, glutamine, methionine and their derivatives. These polyamino acids can, for example, be produced by a known method such as chemical enzymatic polymerization (Numata K. et al., Polymer Journal, 2015; 47: 537-545 and Baker J. P. et al., Biomacromolecules 2012, 13, 947-951 etc.). The polymerization degree of the polyamino acid is in a range of 2 to 100, preferably in a range of 5 to 50, more preferably from 10 to 30, and most preferably in a range of 10 to 20.

In this specification, the structures of polyamino acids, polypeptides and proteins are represented by the three-letter or one-letter notation for amino acids that is conventionally known to those skilled in the art. In this specification, amino acids are in the L-form unless otherwise indicated.

The nano-granular structure—one of the structures composing a spider thread-derived silk, especially a small granular structure composing nano fibrils—refers herein to a structure having a granular form of a high aspect ratio, containing a large amount of glycine and alanine unique to silk, and being mainly composed of a peptide or polypeptide having a β-sheet structure. In the case of the spider silk thread of Nephila edulis, it has been reported that this thread has 17%±4% of the β-sheet structure (Ling S et al, Biomacromolecules, 2011, 12, 3344-3349). In addition, the strongest spider dragline fiber has been reported to have 45 to 65% of a β sheet domain (Vollrath F, et al., Polymer, 2009, 50, 5623-5632).

There, the composite molding composition of the invention can be produced by preparing a dope solution obtained by mixing and dissolving a polypeptide or polyamino acid containing a large amount of β-sheet structure into a fibroin-like protein as a raw material, and then forming, for example, a composite fiber, a composite film, a composite gel, a composite porous body, a composite particle(s) and a composite molded body.

When producing a composite film, a method for producing a film by using a fibroin-derived protein as a raw material is described in International Publication WO2014/103799, and the composite film can basically be produced by this method. When producing a composite fiber, a method for spinning fibers from a fibroin-derived protein is described in International Publication WO2012/165476, and the composite fiber can basically be produced according to this method. When producing a composite gel, a method for producing a gel from a fibroin-derived protein is described in International Publication WO2014/175177, and the composite gel can basically be produced according to this method. Further, when producing a composite porous body, a method for producing a porous body from a fibroin-derived protein is described in International Publication WO2014/175178, the composite porous body can basically be produced according to this method. Furthermore, when producing a composite particle(s), a method for producing a particle(s) from a fibroin-derived protein is described in International Publication WO2014/175179, the composite particle(s) can basically be produced according to this method. Furthermore, when producing a composite molded body, a method for producing a molded body from a fibroin-derived protein is described in the specification of Japanese Patent Application No. 2015-185777, and the composite molded body can basically be produced according to this method.

When the composite molding composition is a composite film produced using the above dope solution, a coating method may be that generally known in this field, such as a casting method, spin-coating method, a dipping method, a spray coating method, an electric field polymerization method, an evaporation method, a vapor-deposition polymerization method, a brush coating method, a blade coating method, a roller coating method, a gravure coating method and a roll-to-roll method.

Further, in the case of performing spinning using the dope solution obtained by adding to the fibroin-derived protein the polypeptide and/or polyamino acid having the β-sheet structure, a fibroin-derived composite fiber can be produced by changing environment-related elements of a fibroin-derived polypeptide fiber such as spider thread, while applying a shearing stress in the spinning process, such environment-related elements being, for example, pH of the dope solution, the type and concentration of a salt, and humidity or water concentration. By varying one or more of these elements, or by blending and changing a plurality of elements, there can be produced a fibroin-derived composite fiber. As a method for producing the fibroin-derived composite fiber of the present invention, there can be specifically listed known spinning methods such as a wet spinning method, a dry spinning method, a wet-dry spinning method and a melt spinning method.

In the embodiment of the present invention, when using a wet spinning method or a dry-wet spinning method, a fibroin-derived peptide fiber can be produced by adding a coagulant to the dope solution while applying a shear stress in a fiber axial direction; or by injecting, pushing out or immersing the dope solution into a solvent containing a coagulant.

A coagulant used in a wet spinning method and a dry-wet spinning method is not particularly limited, as long as it is capable of removing from the dope solution a solvent with which a fibroin-derived protein or the like has been dissolved (also referred to as desolventizing). For example, the coagulant may be a lower alcohol having 1 to 5 carbon atoms, such as methanol, ethanol and 2-propanol; or acetone and the like. Further, there may also be used an aqueous solution containing an inorganic salt. This inorganic salt aqueous solution is preferably a weakly acidic to acidic solvent.

For example, when producing a composite molded body, a protein-containing composition (containing only protein or other ingredients as well) is introduced into a mold of a press molding machine, followed by heating the mold and pressurizing the composition. Heating and pressurizing is then continued under a given pressure until the protein powder has reached a given temperature, thereby obtaining a heated and pressurized composition. Next, a cooler (e.g. spot cooler) is used to lower the temperature of the mold, and the content is then taken out to obtain a molded body when the composition has reached a given temperature. Heating is carried out preferably at 80 to 300° C., more preferably 100 to 180° C., and even more preferably 100 to 130° C. Pressurization is preferably carried out at least 5 kN, more preferably at least 10 kN, and even more preferably at least 20 kN. Further, after the given heating and pressurization condition has been met, a time period for continuing the treatment under such condition (heat-retaining condition) is preferably 0 to 100 minutes, more preferably 1 to 50 minutes, and even more preferably 5 to 30 minutes.

For example, when producing a resin, the resin of the present invention can be produced by preparing a dope solution obtained by dissolving or suspending the above composition of the invention in a solvent, and then insolubilizing the protein in such dope solution with a conventional method publically known to those skilled in the art. As the solvent, there can be used, for example, water or a polar organic solvent; or a mixed solvent thereof. As a method for insolubilizing the protein of the present invention, there may be employed, for example, methods of distilling way the solvent in the dope solution, changing the kind and/or concentration of the salt in the solvent, changing ionic strength or salt concentration and/or changing pH.

In the present specification, the "dope solution" refers to a solution prepared by mixing and dissolving a fibroin-derived protein and a polypeptide and/or polyamino acid having a β-sheet structure serving as raw materials for producing a composite molding composition such as a composite fiber and a composite film.

The polar organic solvent used in the dope solution may be selected from, but is not limited to dimethyl sulfoxide, N,N-dimethylformamide, N,N-dimethylacetamide or 1,1,1,3,3,3-hexafluoro-2-propanol (HFIP), formic acid, or even a mixed solution thereof.

Further, the dope solution may further contain an inorganic salt. An inorganic salt may function as a dissolution promoter for protein. Examples of an inorganic salt include alkali metal halides, alkaline-earth metal halides, alkaline-earth metal nitrates and thiocyanates. Specific examples of such inorganic salt include aluminum phosphate, lithium carbonate, aluminum carbonate, aluminum sulfate, aluminum fluoride, ferric acetate, aluminum acetate, zinc hydroxide, magnesium hydroxide, ferrous hydroxide, manganese hydroxide, chromium hydroxide, ferric hydroxide, aluminum hydroxide, nickel chloride, cobalt chloride, zinc chloride, ferrous chloride, manganese chloride, chromium chloride, ferric chloride, aluminum chloride, lithium nitrate, strontium nitrate, nickel nitrate, calcium nitrate, cobalt nitrate, zinc nitrate, magnesium nitrate, ferrous nitrate, manganese nitrate, chromium nitrate, ferric nitrate, aluminum nitrate, lithium bromide, barium bromide, strontium bromide, nickel bromide, calcium bromide, cobalt bromide, zinc bromide, magnesium bromide, ferrous bromide, manganese bromide, chromium bromide, ferric bromide, aluminum bromide, barium chlorate, strontium chlorate, nickel chlorate, calcium chlorate, cobalt chlorate, zinc chlorate, magnesium chlorate, ferrous chlorate, manganese chlorate, chromium chlorate, ferric chlorate, aluminum chlorate, rubidium iodide, sodium iodide, copper iodide, lithium iodide, barium iodide, strontium iodide, nickel iodide, calcium iodide, cobalt iodide, zinc iodide, magnesium iodide, ferrous iodide, manganese iodide, chromium iodide, ferric iodide, aluminum iodide, sodium perchlorate, lead perchlorate, copper perchlorate, lithium perchlorate, barium perchlorate, strontium perchlorate, nickel perchlorate, calcium perchlorate, cobalt perchlorate, zinc perchlorate, magnesium perchlorate, ferrous perchlorate, manganese perchlorate, chromium perchlorate, ferric perchlorate, aluminum perchlorate, potassium thiocyanate, sodium thiocyanate, lead thiocyanate, copper thiocyanate, lithium thiocyanate, barium thiocyanate, strontium thiocyanate, nickel thiocyanate, calcium thiocyanate, cobalt thiocyanate, zinc thiocyanate, magnesium thiocyanate, ferrous thiocyanate, manganese thiocyanate, chromium thiocyanate, ferric thiocyanate, aluminum thiocyanate, ammonium cyanate, cesium cyanate, rubidium cyanate, potassium cyanate, sodium cyanate, lead cyanate, copper cyanate, lithium cyanate, barium cyanate, strontium cyanate, nickel cyanate, calcium cyanate, cobalt cyanate, zinc cyanate, magnesium cyanate, ferrous cyanate, manganese cyanate, chromium cyanate, ferric cyanate and aluminum cyanate. At least one kind of these inorganic salts may be added to the solvent.

The amount of the inorganic salt contained in the dope solution is not particularly limited, but is appropriately determined based on, for example, the kind of the inorganic salt and the amount of the fibroin-derived protein. The amount of the inorganic salt is, for example, 1.0 part by mass or more, 5.0 parts by mass or more, 9.0 parts by mass or more, 15 parts by mass or more or 20 parts by mass or more, per 100 parts by mass of the total amount of protein. Further, the amount of the inorganic salt may, for example, also be 40 parts by mass or less, 35 parts by mass or less, or 30 parts by mass or less, per 100 parts by mass of the total amount of protein.

In this specification, the amount of the polypeptide and/or polyamino acid added to the fibroin-derived protein is expressed as a ratio of the weight of the polypeptide and/or polyamino acid to the total amount of the fibroin-derived protein and the polypeptide and/or polyamino acid added. For example, when the notation is "composite molding composition of polyAla 5 wt %," it indicates that the composition is a composite molding composition prepared by blending the fibroin-derived protein with the polypeptide and/or polyamino acid at a weight ratio (fibroin-derived protein):(polypeptide and/or polyamino acid) of 95:5. Further, in some cases, it is expressed as a ratio by mass.

The composition of the present invention that contains the fibroin and the polypeptide and/or polyamino acid having the β-sheet structure can, for example, be produced by adding an aqueous solution or aqueous suspension of the polypeptide and/or polyamino acid having the β-sheet structure to the dope solution with the fibroin dissolved therein, mixing them, and then carrying out molding and drying. The compounding ratio of the polypeptide and/or polyamino acid having the β-sheet structure is in a range of 0.1 to 50.0%, preferably in a range of 0.5 to 30.0%, more preferably in a range of 1 to 10.0%, and most preferably in a range of 1 to 5%.

When using polyalanine as the polyamino acid having the β-sheet structure, the polymerization degree of the polyalanine is in a range of 2 to 100, preferably in a range of 3 to 50, more preferably in a range of 10 to 30, and most preferably in a range of 10 to 20. Further, the ratio of the polyalanine added is in a range of 0.1 to 30.0%, preferably in a range of 0.5 to 20.0%, more preferably in a range of 1.0 to 10.0%, and most preferably in a range of 3.0 to 5.0%.

1-2. Pre-Drawn Composite Molding Composition

Another embodiment of the present invention is a pre-drawn composite molding composition. The pre-drawn composite molding composition is produced by allowing the production process of the composite molding composition to further include a process of performing pre-drawing. As compared to a non-drawing composite molding composition, the pre-drawn composite molding composition is capable of bringing about more excellent physical properties.

Specifically, the pre-drawn composite molding composition of this embodiment is a pre-drawn composite molding composition produced by adding the polypeptide and/or polyamino acid having the β-sheet structure to the fibroin-derived protein. This composite molding composition is selected from a fiber or a film, and the pre-drawn composite molding composition is produced by a production method including:

(i) preparing a dope solution in which the fibroin-derived protein and the polypeptide and/or polyamino acid having the β-sheet structure are dissolved;

(ii) molding the composite molding composition from the dope solution; and (iii) drawing the composite molding composition obtained in the process (ii) in a solvent and then drying the composite molding composition.

By adding the pre-drawing process, physical properties such as tensile strength, strain and/or toughness can be further improved. As an example of such pre-drawing process, there may be employed, for example, wet heat drawing and dry heat drawing.

Wet heat drawing may be carried out in warm water, in a solution prepared by adding an organic solvent or the like into warm water or in an organic solvent, or while performing steam heating. The temperature may, for example, be 50 to 90° C., preferably 75 to 85° C. In wet heat drawing, a non-drawing fiber or film (or a pre-drawing fiber or film) may, for example, be drawn to 1 to 10 times, preferably 1 to 4 times.

Dry heat drawing can be carried out using, for example, an electric tubular furnace and a dry hot plate. The temperature may, for example, be 140 to 270° C., preferably 160 to 230° C. In dry heat drawing, a non-drawing fiber or film (or a pre-drawing fiber or film) may, for example, be drawn to 0.5 to 8 times, preferably 1 to 4 times.

Wet heat drawing and dry heat drawing may be carried out individually or in multiple stages, or even in a combined manner. That is, wet heat drawing and dry heat drawing may be appropriately carried out in a combined manner such that, for example, wet heat drawing is performed as a first stage drawing and dry heat drawing is then performed as a second stage drawing; or wet heat drawing is performed as a first stage drawing and the as a second stage drawing, and dry heat drawing is further performed as a third stage drawing.

From the composite molding composition of the present invention, there can be produced, for example, yarns, sheets, unwoven cloths, meshes and nets employing such composition. By utilizing the excellent properties of these composite molding compositions, such as heat resistance, a high tensile strength, toughness and/or stretchability (degree of elongation), the composition(s) can be utilized in the production of materials requiring high impact resistance, such as bulletproof jackets, parachutes and vehicle bodies of automobiles. Further, the composition(s) may be used as a medical material such as a wound closing material with a high strength, a high stretchability and a high toughness, and utilizing biodegradability as well as biocompatibility; a suture thread; an adhesive plaster; and a scaffold material or the like for use in regenerative medicine.

2. Method for Producing the Composite Molding Composition of the Present Invention 2-1. Method for Producing Non-Drawing Composite Molding Composition Another embodiment of the present invention is a method for producing the abovementioned composite molding composition. More specifically, the present invention is a method for producing a composite molding composition that is selected from a fiber, a film and a gel, and is molded by blending a fibroin-derived protein with a polypeptide and/or polyamino acid having a β-sheet structure. This method includes:

(i) preparing a dope solution in which the fibroin-derived protein and the polypeptide and/or polyamino acid having the β-sheet structure are dissolved; and (ii) producing the composite molding composition by performing spinning from the dope solution or further performing drawing.

As described above, for example, as for the fibroin-derived protein, natural fibroin proteins are commercially available, and can be acquired for use in the present invention. Further, there may be employed a modified fibroin-derived protein produced by using a microorganism into which a DNA artificially prepared by a genetic recombination method has been introduced, and then performing isolated purification. The composition of the present invention can be produced by obtaining the fibroin by these methods, and then separately producing the polypeptide and/or polyamino acid having the β-sheet structure by, for example, a known method such as a chemical enzymatic polymerization method (e.g. Numata K. et al., Polymer Journal, 2015; 47: 537-545 and, Baker J. P. et al., Biomacromolecules 2012, 13, in 947-951 etc.), mixing an aqueous suspension of the polypeptide and/or polyamino acid into a dope solution containing the fibroin-derived protein, and then performing insolubilization via drying or the like.

As a method for such insolubilization, other than a method of performing drying, there may be used a method similar to that described in the method for producing the above composite fiber, specifically, methods of, for example, changing the kind and/or concentration of the salt in the solvent, changing ionic strength or salt concentration and/or changing pH.

Furthermore, even with regard to a material(s) other than the fibroin-derived protein, the production method of the present invention can be carried out by using the various kinds of materials described in detail in the above composite molding composition, and by utilizing them in the manners described in detail above.

2-2. Method for Producing Pre-Drawn Composite Molding Composition

Another embodiment of the present invention is a method for producing the pre-drawn composite molding composition. This method includes:
(i) drawing, in a solvent, the composite molding composition produced by the aforementioned production method; and
(ii) drying the composite molding composition drawn.

By adding the pre-drawing process, physical properties such as tensile strength, strain and/or toughness can be further improved. As an example of such pre-drawing process, there may be employed, for example, wet heat drawing and dry heat drawing.

Wet heat drawing may be carried out in warm water, in a solution prepared by adding an organic solvent or the like into warm water or in an organic solvent, or while performing steam heating. The temperature may, for example, be 50 to 90° C., preferably 75 to 85° C. In wet heat drawing, a non-drawing fiber or film (or a pre-drawing fiber or film) may, for example, be drawn to 1 to 10 times, preferably 1 to 4 times.

Dry heat drawing can be carried out using, for example, an electric tubular furnace and a dry hot plate. The temperature may, for example, be 140 to 270° C., preferably 160 to 230° C. In dry heat drawing, a non-drawing fiber or film (or a pre-drawing fiber or film) may, for example, be drawn to 0.5 to 8 times, preferably 1 to 4 times.

Wet heat drawing and dry heat drawing may be carried out individually or in multiple stages, or even in a combined manner. That is, wet heat drawing and dry heat drawing may be appropriately carried out in a combined manner such that, for example, wet heat drawing is performed as a first stage drawing and dry heat drawing is then performed as a second stage drawing; or wet heat drawing is performed as a first stage drawing and the as a second stage drawing, and dry heat drawing is further performed as a third stage drawing.

From the composite molding composition produced by the production method of the present invention, there can be further produced, for example, yarns, sheets, unwoven cloths, meshes and nets employing such composition. By utilizing the excellent properties of these composite molding compositions, such as heat resistance, a high tensile strength, toughness and/or stretchability, the composition(s) can be utilized in the production of materials requiring high impact resistance, such as bulletproof jackets, parachutes and vehicle bodies of automobiles. Further, the composition (s) may be used as a medical material such as a wound closing material with a high strength, a high stretchability and a high toughness, and utilizing biodegradability as well as biocompatibility; a suture thread; an adhesive plaster; and a scaffold material or the like for use in regenerative medicine.

3. Method for Improving Physical Properties of the Composite Molding Composition of the Present Invention Another preferred embodiment of the present invention is a method for improving at least one physical property of the composite molding composition produced from a polypeptide such as a fibroin, such physical property being selected from, for example, tensile strength, toughness and stretchability. Examples of the composite molding composition include a composite film, a composite fiber, a composite gel, a composite porous body, a composite particle(s) and a composite molded body that are produced from a polypeptide.

The method for improving the physical properties of the composite molding composition is to, for example, produce a composite molding composition by adding to a molding composition raw material such as a resin, film and fiber a polyamino acid having the β-sheet structure, such as polyalanine. More specifically, for example, in order to produce a composite molding composition such as a composite film, a composite fiber, a composite gel and a composite resin, the polypeptide and/or polyamino acid having the β-sheet structure is added to and mixed with the dope solution with a raw material such as a fibroin dissolved therein, followed by, for example, distilling away the solvent and insolubilizing the polypeptide, thereby obtaining a composite molding composition with improved physical properties, as compared to a molding composition to which the polypeptide and/or polyamino acid having the β-sheet structure is not added.

In this specification, an improvement in a physical property of the composite molding composition is, for example, such that a commercially available tensile tester is obtained, a tensile strength test is then performed to obtain a critical stress observed when a test sample breaks, and the tensile strength is then deemed to have improved if the value of such critical stress is higher than that of a comparative sample. Further, an improvement in toughness is such that the test sample is likewise subjected to measurement using the tensile tester, and the toughness is then deemed to have improved when the value of an area defined by the curve in a stress-strain curve diagram is higher than an area value observed with the comparative sample. Furthermore, an improvement in stretchability is such that the test sample is likewise subjected to tensile testing using the tensile tester, a strain (rate of elongation) of the test sample as it breaks is then obtained, and the stretchability is then deemed to have improved when the value of the rate of elongation of the test sample as it breaks is higher than the strain of the comparative sample as it breaks, such strain of the comparative sample being obtained by carrying out the measurement under similar conditions.

In the method of the present invention, the polyamino acid used may be a polyamino acid capable of easily forming the β-sheet structure; more specifically, it may, for example, be polyalanine and polycysteine. These polyamino acids may be produced by a known method such as chemical enzymatic synthesis (e.g. Numata K. et al., Polymer Journal, 2015; 47: 537-545, and, Baker J. P. et al., Biomacromolecules 2012, 13, 947-951).

For example, the invention is implemented by adding polyalanine to the molding composition raw material composed of the fibroin-derived polypeptide. If improving the physical properties of the composite molding composition, a polyalanine is to be added to the dope solution in a way such that the polymerization degree of the polyalanine is in a range of 2 to 100, preferably in a range of 3 to 50, more preferably in a range of 10 to 30, and most preferably in a range of 10 to 20, and that the ratio of the polyalanine added is in a range of 0.1 to 30.0%, preferably in a range of 0.5 to 20.0%, more preferably in a range of 1.0 to 10.0%, and most preferably in a range of 3.0 to 5.0%.

By using the method of the present invention, there can be produced, for example, yarns, sheets, unwoven cloths, meshes and nets with further improved physical properties. By utilizing the excellent properties of these composite molding compositions, such as heat resistance, a high tensile strength, toughness and/or stretchability, the composition(s) may be utilized in the production of materials requiring high impact resistance, such as bulletproof jackets, parachutes and vehicle bodies of automobiles. Further, the composition(s) may be used in the production of a medical material such as a wound closing material with a high strength, a high stretchability and a high toughness, and utilizing biodegradability as well as biocompatibility; a suture thread; an adhesive plaster; and a scaffold material or the like for use in regenerative medicine.

Here, all the documents mentioned in this specification are incorporated herein by reference in their entirety.

EXAMPLES

The embodiments of the present invention described below are for illustrative purposes only and shall not limit the technical scope of the present invention. The technical scope of the present invention is limited only by the recitation of the claims. Modifications of the present invention, for example, addition, deletion, and replacement of the constituent features of the present invention may be made provided that the gist of the present invention is not deviated.

Example 1

Production of composite molding films containing polyalanine (L-polyAla or T-polyAla) in naturally derived silkworm fibroin protein or modified spider thread fibroin protein, and evaluation of physical properties thereof.
1. Production of Composite Molding Films Containing Polyalanine in Naturally Derived Silkworm Fibroin Protein PolyAla (L-polyAla or T-polyAla) was synthesized using a method described below, and then the polyalanine (containing 5 or 10 wt % of L-polyAla, or 1 or 2.5 wt % of T-polyAla), produced by the method as described below, and a naturally derived silkworm fibroin protein (Bombix mori) was dissolved therein to prepare a dope solution from which a composite molding film was produced by the casting method. The composite molding film was subject to tensile deformation test to evaluate the changes in physical properties.

The tensile deformation test was conducted using a compact table-top tester (EZ-LX, Shimadzu Corp., Kyoto). Original length of the material was 15.0 mm, which was drawn at a constant rate of 0.5 mm/min. The results were recorded and analyzed by TRAPEZIUM (ver. 1.3.0, Shimadzu Corp., Kyoto). The measurements were carried out at 58% humidity at room temperature.
2. Production of polyAla (L-polyAla or T-polyAla)
(1) Synthesis of Telechelic-Type Polyalanine (T-polyAla)
(i) Synthesis Using Leucine Initiator (Leu-Initiator)
(a) Synthesis of Leucine Initiator (Leu-Initiator)

The synthesis of the telechelic-type polyalanine using leucine initiator mas made by chemoenzymatic polymerization using papain. Specifically, L-leucine ethyl ester hydrochloride (6.07 g), triethylamine (9.2 mL), and diethyl ether (100 mL) were added to a flask at 0° C. under nitrogen. To this solution was added a solution of succinyl chloride (1.7 mL) in diethyl ether (50 mL) dropwise over 30 min, and the resulting mixture was stirred at 0° C. for 2 h. After the mixture was allowed to warm to room temperature, water was added, and the aqueous layer was extracted with diethyl ether. The organic layer was dried with sodium sulfate and concentrated. The crude product was dried in vacuo, and recrystallized with hexane/ethyl acetate (5/1 in volume) to afford 3.57 g of yellow needle-like crystals (60% yield).
(b) Synthesis of Telechelic-Type Polyalanine by Chemoenzymatic Polymerization To a glass tube, alanine ethyl ester hydrochloride (0.645 g), the leucine initiator (0.080 g), phosphate buffer (2 mL, 1 M, pH=8.0), and ethanol (1 mL) were added, and the mixture was stirred at 40° C. until all the substrates were completely dissolved. To this solution was added a solution of papain (0.300 g) in phosphate buffer (2.2 mL) in one portion. The final concentrations of alanine and papain were 0.7 M and 50 mg/mL, respectively. The mixture was stirred at 40° C. for 6 h. After cooling to room temperature, the precipitate was collected by centrifuging at 7000 rpm for 10 min at 4° C. The crude precipitate was washed twice with deionized water and lyophilized to provide 0.071 g of the oligopeptide as a white solid.
(ii) Synthesis of Telechelic-Type Polyalanine Using Bis(alanine ethyl ester) Initiator
(a) Synthesis of Bis(alanine ethyl ester) Initiator To a 200 mL flask, alanine ethyl ester hydrochloride (4.76 g), triethylamine (9.2 mL), and chloroform (100 mL) were added. To this mixture, a solution of succinyl chloride (1.7 mL) in chloroform (50 mL) was added dropwise at 0° C. under nitrogen atmosphere. The resulting solution was stirred at 0° C. for 2 h, and the reaction was quenched by the addition of water. The mixture was washed with water, sodium bicarbonate aq. (1 M), and brine. The organic layer was dried with sodium sulfate and concentrated. The crude product was recrystallized using hexane/ethyl acetate to afford 3.58 g of white needle-shaped crystal (76% yield). The results of the infrared absorption spectrum and NMR spectrum measurement, as well as those of combustion element analysis, are provided as follows: Infrared (IR) (neat): ν=3301, 2991, 1729, 1639, 1545, 1356, 1238, 1204, 1168, 1020 cm$^{-1}$. $^1$H NMR (500 MHz, CDCl$_3$, 25° C., ppm): δ 6.66 (s, 2H), 4.53 (m, 2H) 4.20 (q, J=7.1 Hz, 4H), 2.57 (m, 4H), 1.40 (d, J=7.1 Hz, 6H), 1.28 (t, J=7.1 Hz, 6H). $^{13}$C NMR (125 MHz, CDCl$_3$, 25° C.): δ 173.16, 171.73, 61.37, 48.18, 31.55, 17.97, 14.04. Anal. Calcd for C$_{14}$H$_{24}$N$_2$O$_6$: C, 53.15; H, 7.65; N, 8.86. Found: C, 53.08; H, 7.61; N, 8.85.
(b) Synthesis of T-polyA by Chemoenzymatic Polymerization To a 10 mL glass tube, alanine ethyl ester hydrochloride (0.922 g), the Bis(alanine ethyl ester) initiator (0.190 g), phosphate buffer (2.0 mL, 1 M, pH 8.0), and tetrahydrofuran (1.0 mL) were added, and the mixture was stirred at 40° C. until all substrates were completely dissolved. Then, a solution of papain (0.300 g) in phosphate buffer (2.0 mL) was added in one portion. The final concentrations of alanine ethyl ester and papain were 1 M and 50 mg/mL, respectively. The mixture was stirred at 40° C. for 6 h. After cooling to the room temperature, the precipitate was collected by centrifugation at 7000 rpm and 4° C. for 10 min. The crude product was washed twice with deionized water and methanol and lyophilized to afford a 0.221 g of white powder (61%).
(2) Production of Linear Polyalanine Linear polyalanine (L-polyA) was also synthesized using a procedure similar to that of Telechelic-Type Polyalanine (T-polyAla) except for the condition of no Bis(alanine ethyl ester) Initiator.

(3) Measurements on Average Polymerization Degree and Average Molecular Weight of Polyalanine Average molecular weights of the resultant L-polyAla and T-polyAla were measured using NMR (Varian NMR System 500, Varian Medical Systems, Palo Alto, Calif., the United States of America) and then calculated. The L-polyAla had the average degree of polymerization of 5.8 and the average molecular weight of 531 while the T-polyAla had the average degree of polymerization of 5.9, and the average molecular weight of 593.

Examples of synthesis for such telechelic-type polyalanine (T-polyAla) are described in detail in e.g., Tsuchiya (Tsuchiya K. et. al, Macromol. Biosci. 2016, 16, 1001-1008), and the entire disclosure of which is hereby incorporated by reference.

3. Production of Modified Spider Thread Fibroin Protein and Composite Films Doped with polyAla As a modified spider thread fibroin protein, a recombinant spider silk protein (ADF3KaiLargeNRSH1 of SEQ ID NO 4 and ADF3Kai_noNR of SEQ ID NO.18) was produced by a disclosed method (JP2014-129639) to be used in the production of the composite molding film.

The modified spider thread fibroin protein was used to produce a composite film of the modified spider thread fibroin protein by the casting method similar to the method for producing the composite film of the naturally derived silkworm fibroin protein.

4. Tensile Deformation Test of the Composite Film

Tensile deformation test was conducted for the above composite films by a method similar to the method for producing the composite films of the naturally derived fibroin protein.

5. Production of Pre-Drawn Composite Films and Tensile Deformation Test Thereof

A composite film of the above-described silk (the naturally derived fibroin protein or the modified fibroin protein) doped with polyAla (L-polyAla or T-polyAla) was used to conduct a tensile deformation test for the pre-drawn composite films produced by pre-drawing the films by using the method described below.

Three types of silk films of pure silk, T-polyAla-doped silk, and L-polyAla-doped silk were cut into small pieces (3 mm×15 mm), which were then immersed in methanol for 5 min and slowly pre-drawn using a uniaxial film stretcher (IMC-1A11, Imoto Machinery Co., Ltd., Tokyo) to a length of 1.25-fold, 1.5-fold, 1.75-fold, or 2-fold (drawing ratios were 25, 50, 75, or 100%, respectively). The pre-drawn films were fixed on a glass Petri dish using double-sided tape and dried in a desiccator at room temperature under vacuum for 3 h. Each pre-drawn film underwent mechanical measurements on the tensile properties using a tensile tester (compact desktop tester, EZ Test series, EZ-LX HS of Shimadzu Corporation, Kyoto, Japan) at a drawing rate of 0.5 mm/min at 25° C. at 55 to 60% relative humidity to calculate the maximum tensile strength, strain (elongation at break) and toughness from the obtained stress-strain curves. Five replicates underwent measurement for each measurement to determine the averaged values and standard deviations.

6. Wide Angle X-ray Diffraction (WAXD) Measurements

The Wide Angle X-ray Diffraction (WAXD) for the silk-only films and polyAla containing film, with the pre-drawing ratio of 100%, were performed using the BL45XU beamline (SPring-8, Harima)

Figure 5:
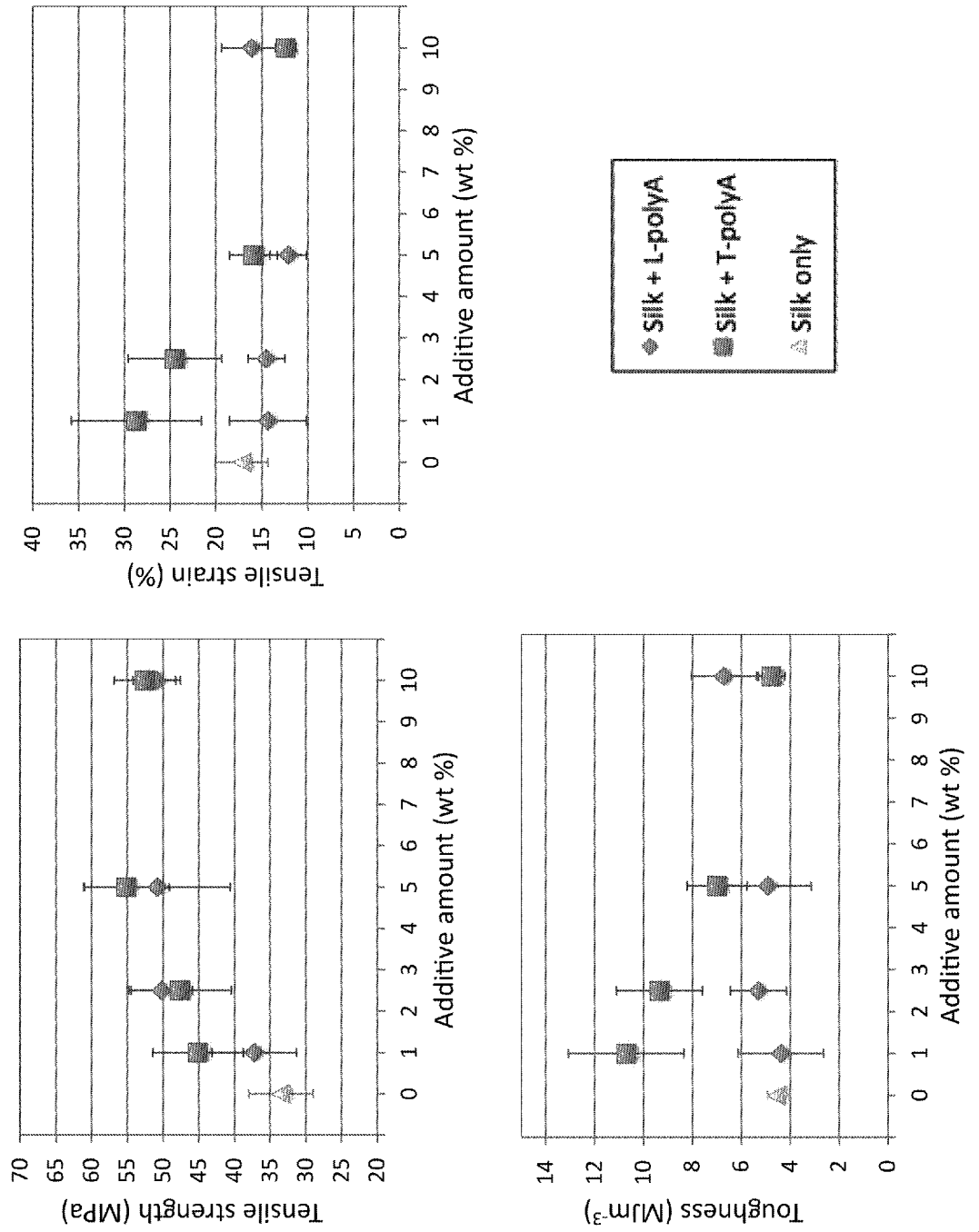
FIG. 5 represents graphs showing the results of measurement of changes of tensile strength, tensile strain, and toughness of a pre-drawn composite film produced by preliminarily stretching or drawing a composite film at a 100% drawing ratio, the composite film being prepared by blending natural silk fibroin protein with L-polyAla or T-polyAla at varying ratios.

7. Results (1) Results on Tensile Deformation Tests for the Composite Film of the Naturally Derived Silkworm Fibroin Protein Tables 1 and 2 and FIG. 5 show the results thereof on the physical properties of the film produced by doping the naturally derived silkworm fibroin protein with 5 or 10 wt % of linear polyalanine (L-polyAla) or 1 or 2.5 wt % of telechelic-type polyalanine (T-polyAla) when the films are not drawn.

The naturally derived silkworm fibroin protein doped with 5 wt % of linear polyalanine (L-polyAla) showed improvements in tensile stress, strain, and toughness.

TABLE 1

Physical properties of the film produced by doping the silkworm fibroin protein (*Bombyx mori*) with 5 or 10 wt % of linear polyalanine (L-polyAla) when the films are not stretched

| Sample | A: Control group(undoped) | B: L-polyA 5% | C: L-polyA 10% |
|---|---|---|---|
| Tensile strength [MPa] | 65.6 ± 4.5 | 71.7 ± 7.8 | 78.7 ± 4.2 |
| Strain[%] | 102.5 ± 17.6 | 113.9 ± 37.5 | 80.8 ± 31.1 |
| Toughness[MJm$^{-3}$] | 61.1 ± 10.7 | 71.4 ± 33.1 | 62.5 ± 31.2 |

TABLE 2

Physical properties of the film produced by doping the silkworm fibroin protein (*Bombyx mori*) with 1 wt % or 2.5 wt % of telechelic-type polyalanine (T-polyAla) when the films are not stretched

| Sample | A: Control group(undoped) | B: T-PolyA 1% | C: T-polyA 2.5% |
|---|---|---|---|
| Tensile strength [MPa] | 65.6 ± 4.5 | 66.5 ± 10.2 | 69.0 ± 11.2 |
| Strain[%] | 102.5 ± 17.6 | 107.4 ± 17.7 | 78.7 ± 14.3 |
| Toughness[MJm$^{-3}$] | 61.1 ± 10.7 | 63.4 ± 17.7 | 44.1 ± 6.3 |

(2) Comparison of Physical Properties of the Composite Films of the Naturally Derived Silkworm (*Bombyx mori*) Fibroin Protein and that of the Modified Spider Thread Fibroin Protein Tensile deformation test was conducted on a composite film (see Tables 3 and 5) of silkworm (*Bombyx mori* fibroin) fibroin doped with 5 wt % of L-polyAla or 1 wt % of T-polyAla and on a composite film (see Tables 4 and 6) of modified spider thread fibroin protein doped with 10 wt % of L-polyAla or 1 wt % of T-polyAla to make a comparison of the physical properties.

The composite film of silkworm fibroin doped with 5 wt % of L-polyAla showed 11.1% increase in strain and 16.9% increase in toughness. Further, the composite film of modified spider thread fibroin protein (ADF Kai-noNR) doped with 1 wt % of T-polyAla showed 66.8% increase in strain and 133% increase in toughness, exhibiting a remarkable improvement in the physical properties.

TABLE 3

Strain [%]: Silkworm silk fibroin (*Bombyx. mori* fibroin)

| Additive | Composite film | Control group (undoped) |
|---|---|---|
| L-polyA 5 wt % | 113.9 ± 37.5 (Increment: 11.1%) | 102.5 ± 17.6 |
| T-polyA 1 wt % | 107.4 ± 17.7 (Increment: 4.8%) | |

TABLE 4

Strain [%]: Modified spider silk fibroin (ADF3 Kai-noNR)

| Additive | Composite film | Control group (undoped) |
|---|---|---|
| L-polyA 10 wt % | 16.1 ± 3.3 (Increment: −6.4%) | 17.2 ± 2.9 |
| T-polyA 1 wt % | 28.7 ± 7.1 (Increment: 66.8%) | |

TABLE 5

Toughness [MJm$^{-3}$]: Silkworm silk fibroin (*Bombyx. mori* fibroin)

| Additive | Composite film | Control group (undoped) |
|---|---|---|
| L-polyA 5 wt % | 71.4 ± 33.1 (Increment: 16.9%) | 61.1 ± 10.7 |
| T-polyA 1 wt % | 63.4 ± 17.7 (Increment: 3.8%) | |

TABLE 6

Toughness [MJm$^{-3}$]: Modified spider silk fibroin (ADF3 Kai-noNR)

| Additive | Composite film | Control group (undoped) |
|---|---|---|
| L-polyA 10 wt % | 6.70 ± 1.33 (Increment: 45.9%) | 4.59 ± 0.34 |
| T-polyA 1 wt % | 10.71 ± 2.38 (Increment: 133%) | |

(3) Results of Tensile Deformation Tests for Pre-Drawn Composite Films

Figure 6:
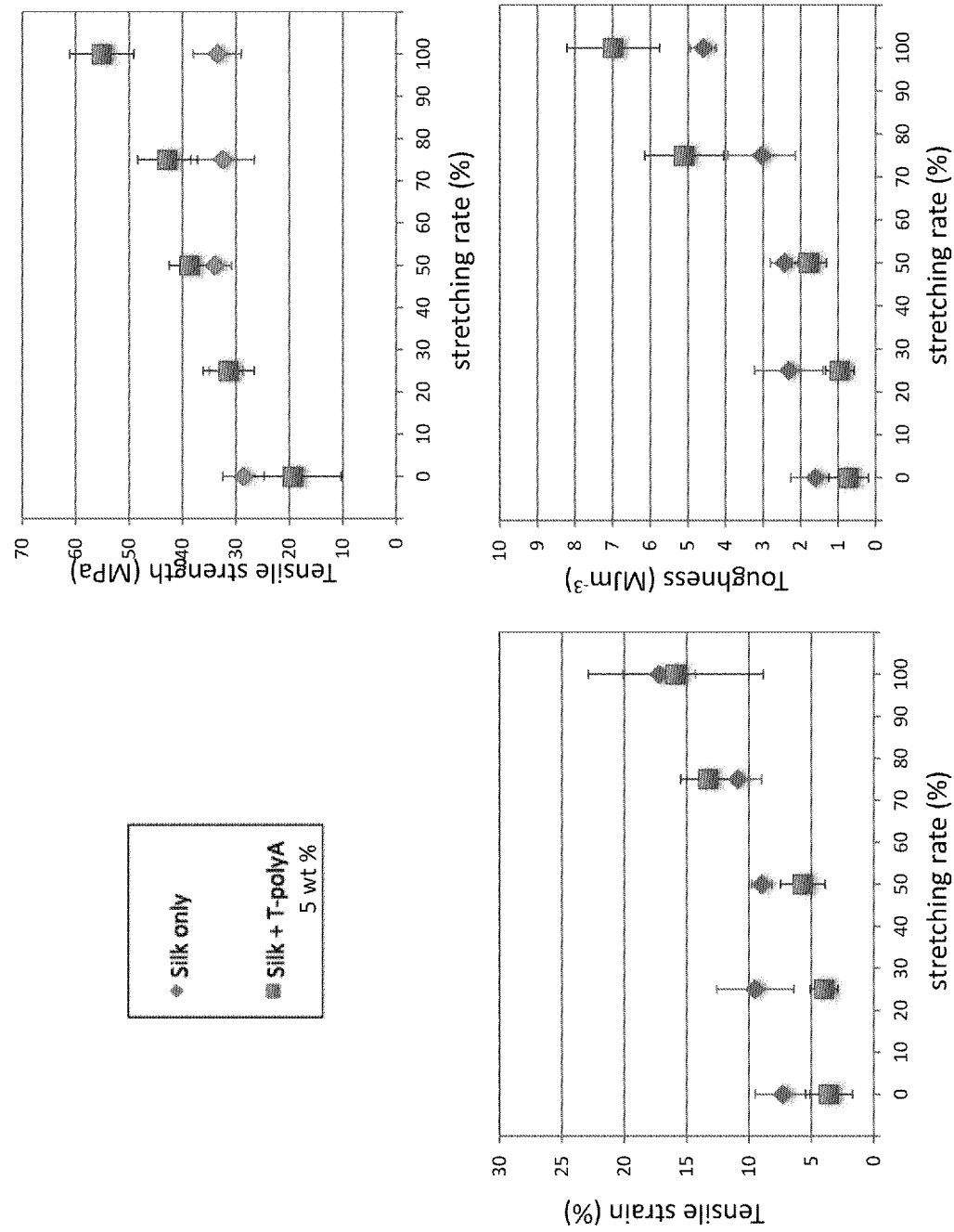
FIG. 6 represents graphs showing the results of measurement of changes of tensile strength, tensile strain, and toughness of a pre-drawn composite film produced by preliminarily stretching or drawing a composite film in a methanol at varying drawing ratios, the composite film being prepared by blending a modified spider silk fibroin protein ADF 3 Kai-noNR with T-polyAla at a ratio of 5 wt %.

FIG. 6 shows results of tensile deformation tests conducted for composite films made by doping 5% of telechelic-type polyalanine (T-polyAla) and then being loaded with a pre-drawing having 0, 25, 50, 75 or 100% of the drawing ratio in the process of making the composite films. The pre-drawing process for composite films doped with telechelic-type polyalanine exhibited a more clear increase in tensile strength, strain, and toughness as compared to those not doped with telechelic-type polyalanine (see FIG. 6).

(4) Result of Wide Angle X-ray Diffraction (WAXD) Measurements

Figure 7:
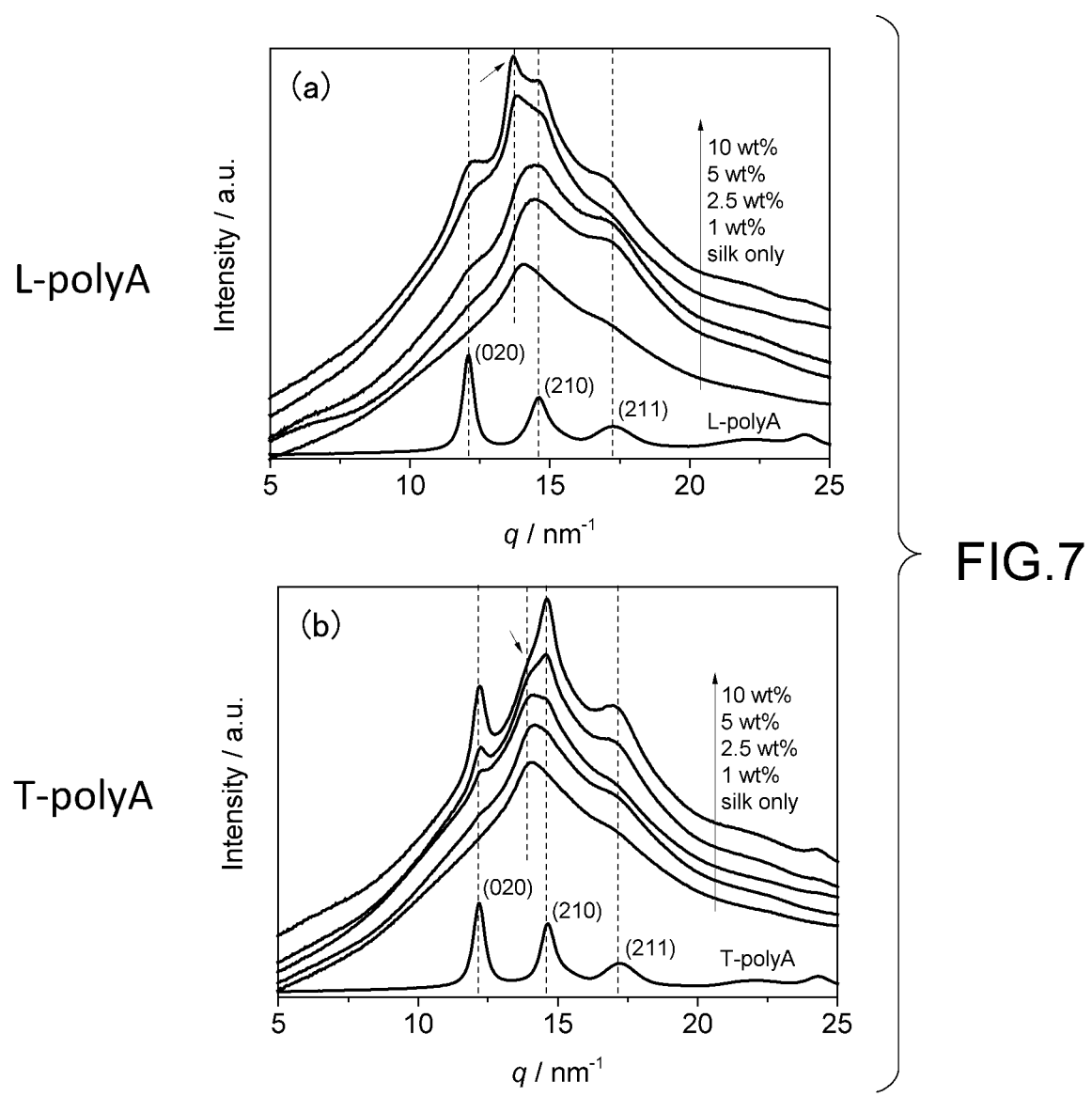
FIG. 7 represents graphs showing the results of measurement of a wide-angle X ray scattering (WAXS) of a composite film produced by preliminarily stretching or drawing a composite film at a 100% drawing ratio, the composite film being prepared by blending a modified spider silk fibroin protein ADF 3 Kai-noNR with T-polyAla or T-polyAla at varying ratios.

FIGS. 7A and 7B show results on WAXD for pre-drawn composite films doped with 0, 1, 2.5, 5 or 10 wt % of L-polyAla or T-polyAla which are pre-drawn to 100% pre-drawing ratio. FIG. 7A shows a variation therein when doped with L-poyAla while FIG. 7B shows a variation when doped with T-polyAla.

The only-silk film exhibits peaks originated from the (020), (210) and (211) planes of crystal lattice based on the antiparallel β-sheet in ADF3. The respective d-spacing were 0.51, 0.45, and 0.37 nm. T-poly A and L-polyA films also exhibit peaks originating from the β-sheet crystal but the inter-planar distance for (210) is 0.43 nm which is different from that of silk-only film.

FIG. 7A shows WAXD 1D profiles of the 100% pre-drawn composite films with various L-polyAla additive amount. All of the peaks associated with polyA's β-sheet became more intense with the increment of additive content. However, the peak intensity of (210) plane was further enhanced not for the polyalanine but for the spider silk's as the L-polyA content exceeded greater than 5 wt %. This result indicates that L-polyA influences the crystal structure of silk owing to the structural similarity between their sequences of L-polyA and silk. It should be considered that the formation of silk's crystals induced by L-polyA leads to the enhancement in the rigidity of the films.

As shown in FIG. 7B illustrating the variation therein for WAXD when T-polyAla was added therein, the intensity of all of the peaks associated with polyalanine was increased in response to the increment of the additive amount. However, the peak intensity of the silk's (210) plane showed no significant change. These results indicate that T-polyA has little effect on the silk's β-sheet owing to the telechelic structure thereof. It should be indicated that the polyalanine independently forms crystals in a dispersed manner to thereby bring an enhancement thereto in the toughness of films with a small additive amount.

As shown above, WAXD on the composite film of the modified spider thread protein doped with 5 wt % of T-polyAla indicated an increase in peak intensities (see FIGS. 7A and 7B) indicating the crystal I response to the increment of doping content of T-polyAla or L-polyAla. It should be considered that T-polyAla or L-polyAla induces an increment of the β-sheet crystal in the silk, which influences the physical properties thereof.

Example 2

Production of composite fiber composition and physical property evaluation thereof 1. Experimental Materials and Methods Unless otherwise noted, all solvents and reagents to be used were obtained from WAKO pure Chemical Corporation in Osaka. The protein powder (SEQ ID NO: 17) was obtained by the following method. The protein power was dried under vacuum at 100° C. for 2 hours before preparing the dope solution. Formic acid was used as the solvent of the dope solution. The spinning was carried out by a desk-top spinning machine No. 1 following the standard procedure of Spiber's desk-top machine manual. The properties of fibers were measured in diameter, tensile stress, tensile strain, and toughness. The diameter was measured using a device of Nikon, ECLIPSE, LV100ND (Tokyo), and then evaluated. The stress and strain were evaluated by a device of INSTRON (Tokyo). The toughness was calculated using a Bluehill's software (INSTRON, Tokyo)

2. Production of Spider Thread Protein (PRT799)

(Synthesis of Gene Encoding Spider Thread Protein, and Construction of Expression Vector)

Based on the base sequence and amino acid sequence of a fibroin derived from *Nephila clavipes* (GenBank Accession Number: P46804.1, GI:1174415), a spider thread protein (herein also referred to as "PRT 799") having an amino acid sequence set forth in SEQ ID NO. 17 was designed.

The amino acid sequence set forth in SEQ ID NO: 17 is an amino acid sequence prepared by adding the amino acid sequence set forth in SEQ ID NO: 21 (containing His tag) to the N-terminal of an amino acid sequence prepared by adding His tag to the C-terminal of a sequence established by repeating 4 times a region of 20 domain sequences in the amino acid sequence set forth in SEQ ID NO.15 (Note that several amino acid residues at the C-terminal side of the region are substituted).

A nucleic acid encoding the designed PRT 799 was synthesized. In the nucleic acid, an NdeI site was added to the 5' end, and an EcoRI site was added downstream of the stop codon. The nucleic acid was cloned into a cloning vector (pUC118). The same nucleic acid was then cleaved by restriction enzyme treatment using NdeI and EcoRI, and then recombined into a protein expression vector pET-22b (+) to obtain an expression vector.

*Escherichia coli* BLR(DE3) was transformed with a pET22b(+) expression vector. The transformed *Escherichia coli* was cultured in 2 mL of an LB medium containing ampicillin for 15 hours. The culture solution was added to 100 ml of a seed culture medium (Table 7) containing ampicillin so that OD600 was 0.005. The temperature of the culture solution was maintained at 30° C. and the flask culture was carried out for about 15 hours until OD600 reached 5 to obtain a seed culture solution.

TABLE 7

| Reagent | Concentration(g/L) |
| --- | --- |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which 500 ml of a production medium (Table 8) had been added so that the OD600 was 0.05. The culture was carried out while maintaining the culture solution temperature at 37° C. and keeping the pH constant at 6.9. Further, the dissolved oxygen concentration in the culture solution was maintained at 20% of the dissolved oxygen saturation concentration.

TABLE 8

| Reagent | Concentration(g/L) |
| --- | --- |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| ADEKA NOL (ADEKA Corporation, LG-295S) | 0.1(mL/L) |

Immediately after completely consuming the glucose in the production medium, a feed solution (455 g/1 L of glucose and 120 g/1 L of Yeast Extract) was added at a rate of 1 ml/min. The culture was carried out while maintaining the culture solution temperature at 37° C. and keeping the pH constant at 6.9. Further, the dissolved oxygen concentration in the culture solution was maintained at 20% of the dissolved oxygen saturation concentration while carrying out the culture for 20 hours. Then, 1 M of isopropyl-β-thiogalactopyranoside (IPTG) was added to the culture solution to a final concentration of 1 mM to induce the expression of the target protein. Twenty hours after addition of IPTG, the culture solution was centrifuged to recover the bacterial cells. SDS-PAGE was carried out using the bacterial cells prepared from the culture solution before the addition of IPTG and after the addition of IPTG, and the expression of PRT799 was identified by the appearance of a band of a target protein size corresponding to PRT799 depending on the addition of IPTG.

[Purification of Spider Thread Protein]

The bacterial cells, recovered 2 hours after the addition of IPTG, were washed with 20 mM Tris-HCl buffer solution (pH 7.4). The bacterial cells after washing were suspended in 20 mM Tris-HCl buffer solution (pH 7.4) containing about 1 mM PMSF, and the cells were disrupted with a high-pressure homogenizer (available from GEA Niro Soavi SpA). The disrupted cells were centrifuged to obtain a precipitate. The obtained precipitate was washed with 20 mM Tris-HCl buffer solution (pH 7.4) to high purity. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so as to have a concentration of 100 mg/mL, and dissolved by stirring with a stirrer at 60° C. for 30 minutes. After the dissolution, dialysis was carried out with water using a dialysis tube (cellulose tube 36/32 manufactured by Sanko Junyaku Co., Ltd.). A white aggregated protein (PRT 799) obtained after dialysis was recovered by centrifugation. The water content was removed from the aggregated protein (PRT 799) with a freeze dryer to obtain a freeze-dried powder.

The degree of purification of the resultant PRT799 in freeze-dried powder form was confirmed by image analysis of polyacrylamide gel electrophoresis results of the powder using TotalLab (Nonlinear Dynamics Ltd.). The purity of PRT799 was about 85%.

The modified spider thread protein thus produced (PRT799, SEQ ID NO: 17) by the above method was used in the experiment as shown below.

3. Experimental Method (1) Preparation of Dope Solution (No L-polyAla and T-polyAla Contained)

The above-described protein powder was used. 3.6 g of the dry powder was precisely weighed and taken into a translucent vial. To this vial was added 11.1 g of formic acid which was stirred overnight at 40° C. to obtain a translucent deep yellow liquid. The protein concentration in this dope solution was 24 wt %.

(2) Preparation of L-polyAla or T-polyAla Contained Dope Solution

The above-described protein powder was used. 0.036 g (1 wt % for the above-mentioned protein powder) of polyAla (L-polyAla or T-polyAla) was taken into a vial to which 11.364 g of formic acid was added and stirred for 1 to 2 hours at 40° C. to be dissolved. After obtaining transparent liquid, the protein powder (3.6 g) was added. The solution was vigorously stirred at 40° C. (normally for 8 to 12 hours) until the protein was completely dissolved therein. This dope solution had a protein concentration of 24 wt %.

(3) Spinning Method

Figure 4:
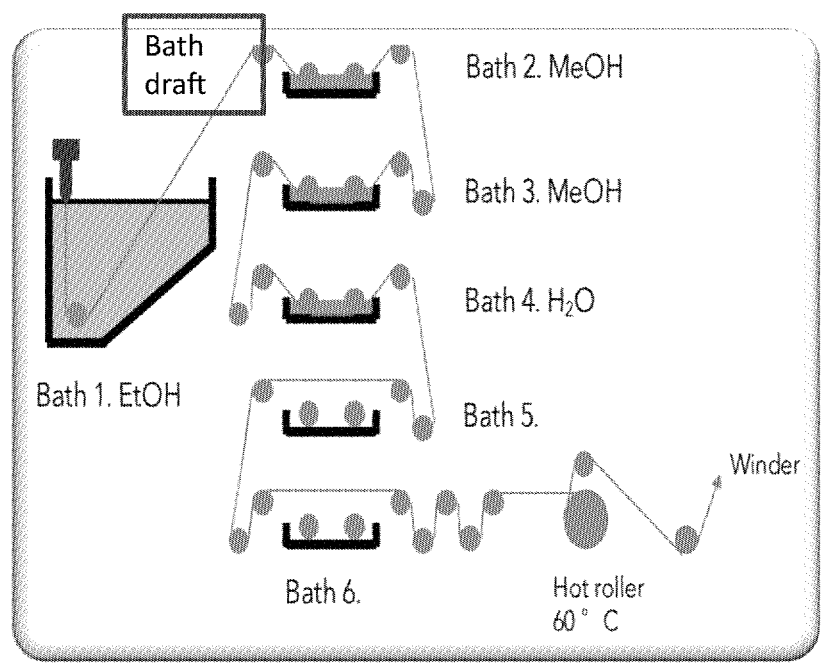
FIG. 4 is a schematic diagram showing an outline of a spinning method from a dope for spinning a composite fiber according to a composite molding composition of the present invention.

The above-described desk-top spinning machine was used for the spinning (see FIG. 4). Tables 9 and 10 summarize the conditions thereof. Bath 1 contained 100% ethanol while Baths 2 and 3 contained 100% methanol. Bath 4 contained water (tap water). No liquid was contained in Baths 5 and 6. The spun fibers were drawn only in Bath 4.

TABLE 9

Discharging condition of polyAla-containing dope solution

| Dope solution: 24 wt % of formic acid | Dope solution content (mL) | Defoaming method | Dope solution discharging nozzle diameter (mm) | Temperature (° C.) | Discharging rate (g/min) | Lineal speed (m/min) |
|---|---|---|---|---|---|---|
| L-polyAla 1 wt % | 15 | Allowed to stand for 1 hr. | 0.2 | 35 | 0.0184 | 0.49 |
| T-polyAla 1 wt % | 15 | Allowed to stand for 1 hr. | 0.2 | 35 | 0.0184 | 0.49 |
| Control | 15 | Allowed to stand for 1 hr. | 0.2 | 35 | 0.0184 | 0.49 |

TABLE 10

Spinning condition of polyAla-containing dope solution

| Coagulation bath | | Bathes 2 and 3 | | Bath 4 | | Bathes 5 and 6 | | Heating roller (60° C.) Rate of pulling speed | Drying |
|---|---|---|---|---|---|---|---|---|---|
| Solvent | Rate of pulling speed | Solvent | Rate of pulling speed | Solvent | Rate of pulling speed | Solvent | Rate of pulling speed | | |
| EtOH | 0.5 or 0.6 | MeOH | 1.0 | water | 7.0-8.0 | none | 1 | 1 | 12 hours in Vacuum |

(4) Evaluation of Physical Properties of Composite Fiber Composition

Tables. 11 and 12 show diameters, tensile strength, strain, toughness, standard deviation of the tensile stress and standard deviation of the strain in fibers which were spun in the draft bath at the rate of pulling speed of 0.6 or 0.5 to the discharging speed where the draw ratio in washing water bath were of 7.0 or 7.8 fold draw ratio.

TABLE 11

| Draw ratio in washing solution | Type of polyAla additive | Fiber diameter (μm) | Tensile strength (MPa) | Strain (%) | Toughness (MJ/m$^3$) | Standard deviation of tensile stress | Standard deviation of tensile strain |
|---|---|---|---|---|---|---|---|
| 7.0 | L-polyAla 1 wt % | 45 | 274 | 14.2 | 24.2 | 12.9 | 1.1 |
| | T-polyAla 1 wt % | 37 | 264 | 7.9 | 13.9 | 12.1 | 0.4 |
| | Control (undoped) | 37 | 229 | 7.1 | 11.0 | 16.8 | 1.2 |
| 7.8 | L-polyAla 1 wt % | 41 | 306 | 11.1 | 20.1 | 31.5 | 1.0 |
| | T-polyAla 1 wt % | 37 | 300 | 6.8 | 12.4 | 10.0 | 0.4 |
| | Control (undoped) | Measurement failed for breakage thereof in spinning process | | | | | |

Linear speed: 0.49 m/min
Rate of pulling speed thereto in draft bath (MeOH): 0.6; Residence time in Bathes 2 and 3: 2 minutes 20 second.

TABLE 12

| Draw ratio in washing solution | Type of polyAla additive | Fiber diameter (μm) | Tensile strength (MPa) | Strain (%) | Toughness (MJ/m$^3$) | Standard deviation of tensile stress | Standard deviation of tensile strain |
|---|---|---|---|---|---|---|---|
| 7.0 | L-polyAla 1 wt % | 46 | 269 | 16.5 | 26.5 | 19.8 | 4.1 |
| | T-polyAla 1 wt % | 43 | 267 | 8.0 | 14.4 | 19.5 | 1.0 |
| | Control (undoped) | 38 | 232 | 6.9 | 10.8 | 19.5 | 1.1 |
| 7.8 | L-polyAla 1 wt % | 46 | 323 | 13.6 | 20.1 | 54.3 | 4.9 |
| | T-polyAla 1 wt % | 42 | 294 | 294 | 12.3 | 31.4 | 0.4 |
| | Control (undoped) | Measurement failed for breakage thereof in spinning process | | | | | |

Linear speed: 0.49 m/min
Rate of pulling speed thereto in draft bath (MeOH): 0.5; Residence time in Bathes 2 and 3: 2 minutes 55 second.

As the rate of pulling speed thereto (pulling speed of fiber/discharging speed of the doping liquid) in the draft bath become smaller, the film tends to have long aggregation time to thereby have stronger aggregation. The above results show improvements in tensile strength, strain and toughness of the composite fibers doped with 1% of L-polyAla or T-polyAla at the rate of pulling speed thereto of both 0.6 and 0.5. The results also show fiber breakage in the process of spinning in control groups as shown in Tables 11 and 12 where no polyAla were added if the draw ratio in washing water was of 7.8 fold. These results show improvement in physical properties of the composite film by doping a fibroin-derived protein with L-polyAla or T-polyAla.

[General Overview]

The above-described results show improvements in physical properties, such as tensile strain, maximum tensile limit, and toughness of the composite film, by doping a natural fibroin protein or an artificially modified and produced fibroin-derived protein with polypeptide or polyamino acid such as L-polyAla or T-polyAla having β-sheet structure. Further, the improvements in physical properties of the composite molding composition have indicated different types of polypeptide or polyamino acid having β-sheet structure for bringing about the optimal properties depending on the type of fibroins to be used. The results also indicate that doping amounts are varied in accordance with optimal physical properties to be brought about such as tensile strain, maximum tensile limit, and toughness.

The results indicate a possibility of obtaining a composite molding composition of improved physical properties by changing the material to be utilized or an additive amount thereof in accordance with desired properties of the composite molding composition.

Furthermore, the fibroin-derived protein may be doped with not only polypeptide or polyamino of natural amino acid but also any polymer having β-sheet structure not originated from the natural amino acid for the production of composite molding composition of the present invention.

The invention claimed is:

1. A composition comprising:
   a fibroin-derived protein; and
   a polyamino acid having a β-sheet structure, wherein
   the polyamino acid consists of a homopolyamino acid or a copolymer of 2 to 5 kinds of amino acids.

2. The composition according to claim 1,
   wherein the composition is a composite molding composition which is obtained by molding the fibroin-derived protein blended with the polyamino acid having the β-sheet structure.

3. The composition according to claim 2,
   wherein the composite molding composition retains the β-sheet structure derived from the polyamino acid.

4. The composition according to claim 2,
   wherein said composite molding composition is selected from a composite fiber, a composite film, a composite gel or a composite molded body.

5. A composite molding composition formed of a fibroin-derived protein blended with a polyamino acid having a β-sheet structure,
   wherein the polyamino acid consists of a homopolyamino acid or a copolymer of 2 to 5 kinds of amino acids,
   wherein the composite molding composition is selected from a composite fiber, a composite film and a composite gel, and is produced by a method comprising:
   (i) preparing a dope solution in which the fibroin-derived protein and the polyamino acid having the β-sheet structure are dissolved; and
   (ii) molding the composite molding composition from the dope solution.

6. A pre-drawn composite molding composition, being selected from a composite fiber or a composite film, and produced by a method comprising the processes (i) and (ii) according to claim 5 and
   (iii) drawing the composite molding composition obtained in the process (ii) in a solvent and then drying the composite molding composition.

7. The composition according to claim 2,
   wherein the fibroin-derived protein is selected from:
   (i) a natural fibroin-derived protein; and/or
   (ii) a modified fibroin-derived protein.

8. The composition according to claim 7,
   wherein the natural fibroin-derived protein is at least one selected from the group consisting of a silk fibroin-derived silk protein (silk fibroin protein), a spider thread fibroin-derived spider thread protein (spider thread fibroin protein) and a hornet silk fibroin-derived hornet silk protein.

9. The composition according to claim 7,
   wherein the modified fibroin-derived protein is a modified fibroin-derived protein having a domain sequence represented by the following formula (I):

$$[(A)_n \text{ motif-REP}]_m \quad \text{(I)},$$

wherein as compared to a naturally derived fibroin, at least one or a plurality of the glycine residues in REP are substituted with a different amino acid residue(s), and the domain sequence has an amino acid sequence with a reduced content of glycine residues,
   in the
   in the $(A)_n$ motif, (A) represents an amino acid residue, n represents an integer of 8 to 20, and the number of alanine residues relative to a total number of the amino acid residues in the $(A)_n$ motif is 40% or more; and wherein the ratio of the number of alanine residues/the total number of the amino acid residues in the $(A)_n$ motif becomes maximum in the calculation;
   REP represents an amino acid sequence consisting of 2 to 200 amino acid residues;
   m represents an integer of 2 to 300;
   the plurality of $(A)_n$ motifs may be the same amino acid sequences or different amino acid sequences; and
   the plurality of REPs may be the same amino acid sequences or different amino acid sequences.

10. The composition according to claim 9,
    wherein in the modified fibroin-derived protein, the domain sequence, as compared to a naturally derived fibroin, has an amino acid sequence equivalent to an amino acid sequence in which, in at least one motif sequence selected from GGX and GPGXX, wherein X represents an amino acid residue other than glycine, in REP, one glycine residue in said at least one motif sequence or a plurality of the motif sequences is substituted with a different amino acid residue(s); and a ratio of the motif sequences in which the glycine residue is substituted with a different amino acid residue(s) is 10% or more with respect to all the motif sequences.

11. The composition according to claim 9,
wherein in the modified fibroin-derived protein, a maximum value of x/y (%) is 20% or more,
in which x represents a sum total of the numbers of amino acid residues in two adjacent [$(A)_n$ motif-REP] units, provided that, with the number of amino acid residues in REPs of two adjacent [$(A)_n$ motif-REP] units being sequentially compared from the N-terminal side to the C-terminal side, when the number of amino acid residues in an REP having a smaller number of amino acid residues is defined as 1, a ratio of the number of amino acid residues in the other REP thereto becomes 2 to 3.5; and
y represents a total number of amino acid residues in the domain sequence.

12. The composition according to claim 9,
wherein the modified fibroin-derived protein represented by the formula (I) is a modified fibroin-derived protein having the amino acid sequence set forth in any one of SEQ ID NOs:4 to 19; or a sequence having a homology of 90% or more with respect to the amino acid sequence of any one of SEQ ID NOs:4 to 19.

13. The composition according to claim 12,
wherein the modified fibroin-derived protein has the sequence of any one of SEQ ID NOs:4 to 19.

14. The composition according to claim 2,
wherein the polyamino acid having the β-sheet structure is a polyalanine.

15. The composition according to claim 14,
wherein the polyalanine is selected from a linear polyalanine or a telechelic polyalanine.

16. The composition according to claim 1,
wherein the polyamino acid having the β-sheet structure has a polymerization degree of 5 to 50.

17. The composition according to claim 16,
wherein the compounding ratio of the polyamino acid having the β-sheet structure is in a range of 0.5 to 30.0%.

18. The composition according to claim 16,
wherein the compounding ratio of the polyamino acid having the β-sheet structure is in a range of 1 to 10.0%.

19. A composite molded body comprising the composition of claim 1, said composite molded body being produced by a method comprising:
(i) preparing the composition by mixing the fibroin-derived protein and the polyamino acid having a β-sheet structure; and
(ii) heating the composition while applying a pressure thereto.

20. A method for producing a composite molding comprising the composition of claim 1 that is formed of the fibroin-derived protein blended with the polyamino acid having a β-sheet structure, and is selected from a composite fiber, a composite film and a composite gel, comprising:
(i) preparing a dope solution in which the fibroin-derived protein and the polyamino acid having the β-sheet structure are dissolved; and
(ii) producing the composition by performing spinning from the dope solution or further performing drawing.

21. A method for producing a pre-drawn composite molding composition, comprising:
(i) drawing, in a solvent, the composition produced by the method according to claim 20; and
(ii) drying the drawn composition.

22. The method according to claim 20,
wherein the fibroin-derived protein is selected from:
(i) a natural fibroin-derived protein; and/or
(ii) a modified fibroin-derived protein.

23. The method according to claim 22,
wherein the natural fibroin-derived protein is at least one selected from the group consisting of a silk fibroin-derived silk protein (silk fibroin protein), a spider thread fibroin-derived spider thread protein (spider thread fibroin protein) and a hornet silk fibroin-derived hornet silk protein.

24. The method according to claim 20,
wherein the polyamino acid having the β-sheet structure is a polyalanine.

25. The method according to claim 24, wherein the polyalanine is selected from a linear polyalanine or a telechelic polyalanine.

* * * * *

SEQUENCE LISTING

```
<160> NUMBER OF SEQ ID NOS: 21

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1154
```

```
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4
```

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
            165                 170                 175

Pro Gly Gly Gln Gly Pro Tyr Gly Pro Gly Ala Ser Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
            245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
            275                 280                 285

Tyr Gly Pro Gly Ala Ser Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gly Pro Tyr Gly
            355                 360                 365

Pro Gly Ala Ser Ala Ala Ala Ala Ala Ala Gly Gly Tyr Gly Pro Gly
            370                 375                 380

-continued

```
Ser Gly Gln Gln Gly Pro Gln Gln Gly Pro Gln Gln Gly Pro
385                 390                 395                 400

Gly Gln Gln Gly Pro Gln Gln Gly Pro Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
                500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Gly Gly Tyr Gly Pro Gly Ser Gly
                580                 585                 590

Gln Gln Gly Pro Ser Gln Gln Gly Pro Gly Gln Gln Gly Pro Gly Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gly Gln Gly Pro
625                 630                 635                 640

Tyr Gly Pro Gly Ser Ser Ala Ala Ala Ala Ala Gly Gly Asn Gly
                645                 650                 655

Pro Gly Ser Gly Gln Gln Gly Ala Gly Gln Gln Gly Pro Gly Gln Gln
                660                 665                 670

Gly Pro Gly Ala Ser Ala Ala Ala Ala Ala Gly Gly Tyr Gly Pro
            675                 680                 685

Gly Ser Gly Gln Gln Gly Pro Gly Gln Gln Gly Pro Gly Gly Gln Gly
            690                 695                 700

Pro Tyr Gly Pro Gly Ala Ser Ala Ala Ala Ala Ala Gly Gly Tyr
705                 710                 715                 720

Gly Pro Gly Ser Gly Gln Gly Pro Gly Gln Gln Gly Pro Gly Gly Gln
                725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
755                 760                 765

Gln Gln Gly Pro Gly Gly Gln Gly Pro Tyr Gly Pro Gly Ala Ser Ala
            770                 775                 780

Ala Ala Ala Ala Gly Gly Tyr Gly Pro Gly Tyr Gly Gln Gln Gly
785                 790                 795                 800
```

```
Pro Gly Gln Gln Gly Pro Gly Gly Gln Gly Pro Tyr Gly Pro Gly Ala
            805                 810                 815

Ser Ala Ala Ser Ala Ala Ser Gly Gly Tyr Gly Pro Ser Gly Gln
        820                 825                 830

Gln Gly Pro Gly Gln Gln Gly Pro Gly Gln Gln Gly Pro Tyr Gly Pro
        835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
        900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
        930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
        980                 985                 990

Gly Gln Gln Gly Pro Gly Gln Gln Gly Pro Gly Gln Gln Gly Pro Gly
        995                1000                1005

Gln Gln Gly Pro Gly Gln Gln Gly Pro Tyr Gly Pro Gly Ala Ser
       1010                1015                1020

Ala Ala Ala Ala Ala Gly Gly Tyr Gly Pro Gly Ser Gly Gln
       1025                1030                1035

Gln Gly Pro Gly Gln Gln Gly Pro Gly Gln Gln Gly Pro Gly Gly
       1040                1045                1050

Gln Gly Pro Tyr Gly Pro Gly Ala Ala Ser Ala Ala Val Ser Val
       1055                1060                1065

Gly Gly Tyr Gly Pro Gln Ser Ser Ser Val Pro Val Ala Ser Ala
       1070                1075                1080

Val Ala Ser Arg Leu Ser Ser Pro Ala Ala Ser Ser Arg Val Ser
       1085                1090                1095

Ser Ala Val Ser Ser Leu Val Ser Ser Gly Pro Thr Lys His Ala
       1100                1105                1110

Ala Leu Ser Asn Thr Ile Ser Ser Val Val Ser Gln Val Ser Ala
       1115                1120                1125

Ser Asn Pro Gly Leu Ser Gly Cys Asp Val Leu Val Gln Ala Leu
       1130                1135                1140

Leu Glu Val Val Ser Ala Leu Val Ser Ile Leu
       1145                1150

<210> SEQ ID NO 5
<211> LENGTH: 1131
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 5
```

```
Met Ala Arg Ala Gly Ser Gln Gln Gly Pro Gly Gln Gly Pro
1               5                   10                  15

Gly Gln Gln Gly Pro Gly Gln Gln Gly Pro Tyr Gly Pro Gly Ala Ser
            20                  25                  30

Ala Ala Ala Ala Ala Ala Gly Gly Tyr Gly Pro Gly Ser Gly Gln Gln
            35                  40                  45

Gly Pro Ser Gln Gln Gly Pro Gly Gln Gln Gly Pro Gly Gln Gly
        50                  55                  60

Pro Tyr Gly Pro Gly Ala Ser Ala Ala Ala Ala Ala Gly Gly Tyr
65              70                  75                  80

Gly Pro Gly Ser Gly Gln Gln Gly Pro Gly Gln Gln Gly Pro Tyr Gly
            85                  90                  95

Pro Gly Ser Ser Ala Ala Ala Ala Ala Ala Gly Gly Asn Gly Pro Gly
            100                 105                 110

Ser Gly Gln Gln Gly Ala Gly Gln Gln Gly Pro Gly Gln Gln Gly Pro
            115                 120                 125

Gly Ala Ser Ala Ala Ala Ala Ala Gly Gly Tyr Gly Pro Gly Ser
        130                 135                 140

Gly Gln Gln Gly Pro Gly Gln Gln Gly Pro Gly Gln Gly Pro Tyr
145                 150                 155                 160

Gly Pro Gly Ala Ser Ala Ala Ala Ala Ala Gly Gly Tyr Gly Pro
                165                 170                 175

Gly Ser Gly Gln Gly Pro Gly Gln Gln Gly Pro Gly Gln Gly Pro
            180                 185                 190

Tyr Gly Pro Gly Ala Ser Ala Ala Ala Ala Ala Gly Gly Tyr Gly
        195                 200                 205

Pro Gly Ser Gly Gln Gln Gly Pro Gly Gln Gln Gly Pro Gly Gln Gln
210                 215                 220

Gly Pro Gly Gly Gln Gly Pro Tyr Gly Pro Gly Ala Ser Ala Ala Ala
225                 230                 235                 240

Ala Ala Ala Gly Gly Tyr Gly Pro Gly Tyr Gly Gln Gln Gly Pro Gly
                245                 250                 255

Gln Gln Gly Pro Gly Gln Gly Pro Tyr Gly Pro Gly Ala Ser Ala
            260                 265                 270

Ala Ser Ala Ala Ser Gly Gly Tyr Gly Pro Gly Ser Gly Gln Gln Gly
        275                 280                 285

Pro Gly Gln Gln Gly Pro Gly Gly Gln Gly Pro Tyr Gly Pro Gly Ala
        290                 295                 300

Ser Ala Ala Ala Ala Ala Gly Gly Tyr Gly Pro Gly Ser Gly Gln
305                 310                 315                 320

Gln Gly Pro Gly Gln Gln Gly Pro Gly Gln Gln Gly Pro Gly Gln Gln
            325                 330                 335

Gly Pro Gly Gly Gln Gly Pro Tyr Gly Pro Gly Ala Ser Ala Ala Ala
            340                 345                 350

Ala Ala Ala Gly Gly Tyr Gly Pro Gly Ser Gly Gln Gln Gly Pro Gly
            355                 360                 365

Gln Gln Gly Pro Gly Gln Gln Gly Pro Gly Gln Gln Gly Pro Gly Gln
            370                 375                 380

Gln Gly Pro Gly Gln Gln Gly Pro Gly Gln Gln Gly Pro Gly Gln Gln
385                 390                 395                 400

Gly Pro Gly Gln Gln Gly Pro Gly Gly Gln Gly Ala Tyr Gly Pro Gly
            405                 410                 415
```

```
Ala Ser Ala Ala Ala Gly Ala Ala Gly Tyr Gly Pro Gly Ser Gly
            420                 425                 430
Gln Gln Gly Pro Gly Gln Gln Gly Pro Gly Gln Gln Gly Pro Gly Gln
        435                 440                 445
Gln Gly Pro Gly Gln Gln Gly Pro Gly Gln Gln Gly Pro Gly Gln Gln
    450                 455                 460
Gly Pro Gly Gln Gln Gly Pro Tyr Gly Pro Gly Ala Ser Ala Ala Ala
465                 470                 475                 480
Ala Ala Ala Gly Gly Tyr Gly Pro Gly Ser Gly Gln Gln Gly Pro Gly
            485                 490                 495
Gln Gln Gly Pro Gly Gln Gln Gly Pro Gly Gln Gln Gly Pro Tyr Gly
        500                 505                 510
Pro Gly Ala Ala Ser Ala Ala Val Ser Val Ser Arg Ala Arg Ala Gly
    515                 520                 525
Ser Gly Gln Gln Gly Pro Gly Gln Gln Gly Pro Gly Gln Gln Gly Pro
530                 535                 540
Gly Gln Gln Gly Pro Tyr Gly Pro Gly Ala Ser Ala Ala Ala Ala Ala
545                 550                 555                 560
Ala Gly Gly Tyr Gly Pro Gly Ser Gly Gln Gln Gly Pro Ser Gln Gln
            565                 570                 575
Gly Pro Gly Gln Gln Gly Pro Gly Gln Gly Pro Tyr Gly Pro Gly
        580                 585                 590
Ala Ser Ala Ala Ala Ala Ala Gly Gly Tyr Gly Pro Gly Ser Gly
            595                 600                 605
Gln Gln Gly Pro Gly Gly Gln Gly Pro Tyr Gly Pro Gly Ser Ser Ala
        610                 615                 620
Ala Ala Ala Ala Ala Gly Gly Asn Gly Pro Gly Ser Gly Gln Gln Gly
625                 630                 635                 640
Ala Gly Gln Gln Gly Pro Gly Gln Gln Gly Pro Gly Ala Ser Ala Ala
            645                 650                 655
Ala Ala Ala Ala Gly Gly Tyr Gly Pro Gly Ser Gly Gln Gln Gly Pro
        660                 665                 670
Gly Gln Gln Gly Pro Gly Gly Gln Gly Pro Tyr Gly Pro Gly Ala Ser
    675                 680                 685
Ala Ala Ala Ala Ala Ala Gly Gly Tyr Gly Pro Gly Ser Gly Gln Gly
        690                 695                 700
Pro Gly Gln Gln Gly Pro Gly Gly Gln Gly Pro Tyr Gly Pro Gly Ala
705                 710                 715                 720
Ser Ala Ala Ala Ala Ala Ala Gly Gly Tyr Gly Pro Gly Ser Gly Gln
            725                 730                 735
Gln Gly Pro Gly Gln Gln Gly Pro Gly Gln Gln Gly Pro Gly Gly Gln
        740                 745                 750
Gly Pro Tyr Gly Pro Gly Ala Ser Ala Ala Ala Ala Ala Ala Gly Gly
    755                 760                 765
Tyr Gly Pro Gly Tyr Gly Gln Gln Gly Pro Gly Gln Gln Gly Pro Gly
        770                 775                 780
Gly Gln Gly Pro Tyr Gly Pro Gly Ala Ser Ala Ala Ser Ala Ala Ser
785                 790                 795                 800
Gly Gly Tyr Gly Pro Gly Ser Gly Gln Gln Gly Pro Gly Gln Gln Gly
            805                 810                 815
Pro Gly Gly Gln Gly Pro Tyr Gly Pro Gly Ala Ser Ala Ala Ala Ala
        820                 825                 830
Ala Ala Gly Gly Tyr Gly Pro Gly Ser Gly Gln Gln Gly Pro Gly Gln
```

-continued

```
                835                 840                 845
Gln Gly Pro Gly Gln Gln Gly Pro Gly Gln Gln Gly Pro Gly Gly Gln
            850                 855                 860

Gly Pro Tyr Gly Pro Gly Ala Ser Ala Ala Ala Ala Ala Ala Gly Gly
865                 870                 875                 880

Tyr Gly Pro Gly Ser Gly Gln Gln Gly Pro Gly Gln Gln Gly Pro Gly
                885                 890                 895

Gln Gln Gly Pro Gly Gln Gln Gly Pro Gly Gln Gln Gly Pro Gly Gln
            900                 905                 910

Gln Gly Pro Gly Gln Gln Gly Pro Gly Gln Gln Gly Pro Gly Gln Gln
        915                 920                 925

Gly Pro Gly Gly Gln Gly Ala Tyr Gly Pro Gly Ala Ser Ala Ala Ala
        930                 935                 940

Gly Ala Ala Gly Gly Tyr Gly Pro Gly Ser Gly Gln Gln Gly Pro Gly
945                 950                 955                 960

Gln Gln Gly Pro Gly Gln Gln Gly Pro Gly Gln Gln Gly Pro Gly Gln
                965                 970                 975

Gln Gly Pro Gly Gln Gln Gly Pro Gly Gln Gln Gly Pro Gly Gln Gln
            980                 985                 990

Gly Pro Tyr Gly Pro Gly Ala Ser  Ala Ala Ala Ala  Ala Gly Gly
        995                 1000                1005

Tyr Gly  Pro Gly Ser Gly Gln  Gln Gly Pro Gly Gln  Gln Gly Pro
    1010                1015                1020

Gly Gln  Gln Gly Pro Gly Gly  Gln Gly Pro Tyr Gly  Pro Gly Ala
    1025                1030                1035

Ala Ser  Ala Ala Val Ser Val  Gly Gly Tyr Gly Pro  Gln Ser Ser
    1040                1045                1050

Ser Val  Pro Val Ala Ser Ala  Val Ala Ser Arg Leu  Ser Ser Pro
    1055                1060                1065

Ala Ala  Ser Ser Arg Val Ser  Ser Ala Val Ser Ser  Leu Val Ser
    1070                1075                1080

Ser Gly  Pro Thr Lys His Ala  Ala Leu Ser Asn Thr  Ile Ser Ser
    1085                1090                1095

Val Val  Ser Gln Val Ser Ala  Ser Asn Pro Gly Leu  Ser Gly Cys
    1100                1105                1110

Asp Val  Leu Val Gln Ala Leu  Leu Glu Val Val Ser  Ala Leu Val
    1115                1120                1125

Ser Ile  Leu
    1130

<210> SEQ ID NO 6
<211> LENGTH: 597
<212> TYPE: PRT
<213> ORGANISM: Artificial Sequence
<220> FEATURE:
<223> OTHER INFORMATION: Met-PRT313: Met-CRY1_L_A5

<400> SEQUENCE: 6

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Ala Gly Gly Tyr Gly Pro Gly Gly Gln Gly
        35                  40                  45

Pro Gly Gln Gln Gly Pro Gly Ser Ser Ala Ala Ala Ala Ala Gly Pro
```

-continued

```
            50                  55                  60
Gly Gly Tyr Gly Pro Gly Gln Gly Pro Ser Ala Ser Ala Ala Ala
 65                  70                  75                  80

Ala Ala Gly Pro Gly Ser Gly Gln Gln Gly Pro Gly Ala Ser Ala Ala
                 85                  90                  95

Ala Ala Ala Gly Gly Tyr Gly Pro Gly Gln Gly Pro Gly Gln Gln
                100                 105                 110

Gly Pro Gly Ser Ser Ala Ala Ala Ala Gly Gly Tyr Gly Ser Gly
            115                 120                 125

Pro Gly Gln Gln Gly Pro Tyr Gly Ser Ala Ala Ala Ala Gly Pro
            130                 135                 140

Gly Ser Gly Gly Tyr Gly Gln Gly Pro Tyr Gly Pro Gly Ala Ser Ala
145                 150                 155                 160

Ala Ala Ala Ala Gly Pro Gly Gly Tyr Gly Pro Gly Gln Gly Pro
                165                 170                 175

Ser Ala Ser Ala Ala Ala Ala Gly Ser Gly Gln Gln Gly Pro Gly
            180                 185                 190

Gly Tyr Gly Pro Tyr Ala Ser Ala Ala Ala Ala Gly Gly Tyr Gly
            195                 200                 205

Ser Gly Pro Gly Gln Gln Gly Pro Tyr Gly Pro Gly Gly Ser Ala Ala
210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
            245                 250                 255

Pro Gly Ser Ser Ala Ala Ala Ala Gly Gly Tyr Gly Tyr Gly Pro
            260                 265                 270

Gly Gly Gln Gly Pro Tyr Gly Pro Gly Ala Ser Ala Ala Ala Ala
            275                 280                 285

Gly Gly Asn Gly Pro Gly Ser Gly Gly Tyr Gly Pro Gly Gln Gln Gly
            290                 295                 300

Pro Gly Gly Ser Ala Ala Ala Ala Gly Pro Gly Gly Gln Gly Pro
305                 310                 315                 320

Tyr Gly Pro Gly Ala Ser Ala Ala Ala Ala Gly Gly Tyr Gly Pro
            325                 330                 335

Gly Gly Gln Gly Pro Gly Gly Tyr Gly Pro Gly Ser Ser Ala Ala Ala
            340                 345                 350

Ala Ala Gly Pro Gly Gly Gln Gly Pro Tyr Gly Pro Gly Ser Ser Ala
            355                 360                 365

Ala Ala Ala Gly Gly Tyr Gly Pro Gly Gln Gln Gly Pro Tyr Gly
            370                 375                 380

Pro Gly Gly Ser Ala Ala Ala Ala Gly Tyr Gln Gln Gly Pro
385                 390                 395                 400

Gly Gly Gln Gly Pro Tyr Gly Pro Gly Ala Ser Ala Ala Ala Ala
            405                 410                 415

Gly Pro Gly Gly Gln Gly Pro Tyr Gly Pro Gly Ala Ser Ala Ala Ala
            420                 425                 430

Ala Ala Gly Pro Gly Gly Tyr Gly Pro Gly Gly Gln Gly Pro Ser Ala
            435                 440                 445

Ser Ala Ala Ala Ala Gly Gly Tyr Gly Ser Gly Pro Gly Gly Tyr
450                 455                 460

Gly Pro Tyr Gly Pro Gly Gly Ser Ala Ala Ala Ala Ala Gly Pro Gly
465                 470                 475                 480
```

Ser Gly Gln Gln Gly Gln Pro Tyr Gly Pro Gly Ala Ser Ala Ala
            485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Gly Pro Ser Gly Gly Tyr Gly
            515                 520                 525

Pro Gly Ala Ser Ala Ala Ala Ala Gly Gly Asn Gly Pro Gly Ser
            530                 535                 540

Gly Gly Tyr Gly Pro Gly Gln Gln Pro Gly Gly Ser Ala Ala Ala
545                 550                 555                 560

Ala Ala Gly Gly Tyr Gln Gln Gly Pro Gly Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
            595

<210> SEQ ID NO 7
<211> LENGTH: 590
<212> TYPE: PRT
<213> ORGANISM: Artificial Sequence
<220> FEATURE:
<223> OTHER INFORMATION: Met-PRT399: Met-CRY1_L_A5_giza

<400> SEQUENCE: 7

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
                20                  25                  30

Gly Ser Gly Gly Tyr Gly Pro Gly Gln Gly Pro Gln Gln Gly
            35                  40                  45

Pro Gly Ser Ser Ala Ala Ala Ala Gly Pro Gly Gly Tyr Gly Pro
        50                  55                  60

Gly Gly Gln Pro Ser Ala Ser Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala Ala
            100                 105                 110

Gly Gly Tyr Gly Ser Gly Pro Gly Gln Gln Pro Tyr Gly Ser Ala
            115                 120                 125

Ala Ala Ala Ala Gly Pro Gly Ser Gly Gly Tyr Gly Gln Pro Tyr
        130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Gly Ser Gly Gln Gln Gly Pro
            165                 170                 175

Gly Gly Tyr Gly Pro Tyr Ala Ser Ala Ala Ala Ala Gly Gly Tyr
            180                 185                 190

Gly Ser Gly Pro Gly Gln Gln Gly Pro Tyr Gly Pro Gly Gly Ser Gly
            195                 200                 205

Ser Gly Gln Gln Gly Pro Gly Gln Gln Gly Pro Tyr Ala Ser Ala Ala
        210                 215                 220

Ala Ala Ala Gly Pro Gly Gly Gln Gly Pro Tyr Gly Pro Gly Ser Ser
225                 230                 235                 240

Ala Ala Ala Ala Ala Gly Gly Tyr Gly Tyr Gly Pro Gly Gly Gln Gly
            245                 250                 255

Pro Tyr Gly Pro Gly Ala Ser Gly Gly Asn Gly Pro Gly Ser Gly Gly
        260                 265                 270

Tyr Gly Pro Gly Gln Gln Gly Pro Gly Gly Ser Ala Ala Ala Ala Ala
        275                 280                 285

Gly Pro Gly Gly Gln Gly Pro Tyr Gly Pro Gly Ala Ser Ala Ala Ala
        290                 295                 300

Ala Ala Gly Gly Tyr Gly Pro Gly Gly Gln Gly Pro Gly Gly Tyr Gly
305                 310                 315                 320

Pro Gly Ser Ser Gly Pro Gly Gly Gln Gly Pro Tyr Gly Pro Gly Ser
            325                 330                 335

Ser Ala Ala Ala Ala Ala Gly Gly Tyr Gly Pro Gly Gln Gln Gly Pro
            340                 345                 350

Tyr Gly Pro Gly Gly Ser Ala Ala Ala Ala Gly Gly Tyr Gln Gln
            355                 360                 365

Gly Pro Gly Gly Gln Gly Pro Tyr Gly Pro Gly Ala Ser Gly Pro Gly
        370                 375                 380

Gly Gln Gly Pro Tyr Gly Pro Gly Ala Ser Ala Ala Ala Ala Gly
385                 390                 395                 400

Pro Gly Gly Tyr Gly Pro Gly Gly Gln Gly Pro Ser Ala Ser Ala Ala
            405                 410                 415

Ala Ala Ala Gly Gly Tyr Gly Ser Pro Gly Gly Tyr Gly Pro Tyr
            420                 425                 430

Gly Pro Gly Gly Ser Gly Pro Gly Ser Gly Gln Gln Gly Gln Gly Pro
            435                 440                 445

Tyr Gly Pro Gly Ala Ser Ala Ala Ala Ala Gly Gly Tyr Gly Pro
            450                 455                 460

Gly Gln Gln Gly Pro Tyr Gly Pro Gly Ser Ala Ala Ala Ala
465                 470                 475                 480

Gly Pro Gly Ser Gly Gly Tyr Gly Pro Gly Ala Ser Gly Gly Asn Gly
            485                 490                 495

Pro Gly Ser Gly Gly Tyr Gly Pro Gly Gln Gln Gly Pro Gly Gly Ser
            500                 505                 510

Ala Ala Ala Ala Ala Gly Gly Tyr Gln Gln Gly Pro Gly Gly Gln Gly
            515                 520                 525

Pro Tyr Gly Pro Gly Ala Ser Ala Ala Ala Ala Gly Gly Tyr Gly
        530                 535                 540

Ser Gly Pro Gly Gln Gln Gly Pro Tyr Gly Pro Gly Ser Gly Ser
545                 550                 555                 560

Gly Gln Gln Gly Pro Gly Gln Gln Gly Pro Tyr Ala Ser Ala Ala Ala
            565                 570                 575

Ala Ala Gly Pro Gly Ser Gly Gln Gln Gly Pro Gly Ala Ser
            580                 585                 590

<210> SEQ ID NO 8
<211> LENGTH: 597
<212> TYPE: PRT
<213> ORGANISM: Artificial Sequence
<220> FEATURE:
<223> OTHER INFORMATION: Met-PRT380: Met-CRY1_L_A5_QQQ

<400> SEQUENCE: 8

Met Gly Pro Gly Gln Gln Gly Pro Tyr Gly Pro Gly Ala Ser Ala Ala
1               5                   10                  15

```
Ala Ala Ala Gly Gln Asn Gly Pro Gly Ser Gly Gln Gln Gly Pro Gly
            20                  25                  30
Gln Ser Ala Ala Ala Ala Gly Gln Tyr Gly Pro Gly Gln Gln Gly
        35                  40                  45
Pro Gly Gln Gln Gly Pro Gly Ser Ser Ala Ala Ala Ala Gly Pro
    50                  55                  60
Gly Gln Tyr Gly Pro Gly Gln Gly Pro Ser Ala Ser Ala Ala Ala
65                  70                  75                  80
Ala Ala Gly Pro Gly Ser Gln Gln Gly Pro Gly Ala Ser Ala Ala
            85                  90                  95
Ala Ala Ala Gly Gln Tyr Gly Pro Gly Gln Gly Pro Gly Gln Gln
            100                 105                 110
Gly Pro Gly Ser Ser Ala Ala Ala Ala Gly Gln Tyr Gly Ser Gly
            115                 120                 125
Pro Gly Gln Gln Gly Pro Tyr Gly Ser Ala Ala Ala Ala Gly Pro
    130                 135                 140
Gly Ser Gly Gln Tyr Gly Gln Gly Pro Tyr Gly Pro Gly Ala Ser Ala
145                 150                 155                 160
Ala Ala Ala Ala Gly Pro Gly Gln Tyr Gly Pro Gly Gln Gln Gly Pro
            165                 170                 175
Ser Ala Ser Ala Ala Ala Ala Gly Ser Gly Gln Gln Gly Pro Gly
            180                 185                 190
Gln Tyr Gly Pro Tyr Ala Ser Ala Ala Ala Ala Gly Gln Tyr Gly
        195                 200                 205
Ser Gly Pro Gly Gln Gln Gly Pro Tyr Gly Pro Gly Gln Ser Ala Ala
    210                 215                 220
Ala Ala Ala Gly Ser Gly Gln Gln Gly Pro Gly Gln Gln Gly Pro Tyr
225                 230                 235                 240
Ala Ser Ala Ala Ala Ala Gly Pro Gly Gln Gln Gly Pro Tyr Gly
        245                 250                 255
Pro Gly Ser Ser Ala Ala Ala Ala Gly Gln Tyr Gly Tyr Gly Pro
    260                 265                 270
Gly Gln Gln Gly Pro Tyr Gly Pro Gly Ala Ser Ala Ala Ala Ala
    275                 280                 285
Gly Gln Asn Gly Pro Gly Ser Gly Gln Tyr Gly Pro Gly Gln Gln Gly
        290                 295                 300
Pro Gly Gln Ser Ala Ala Ala Ala Gly Pro Gly Gln Gln Gly Pro
305                 310                 315                 320
Tyr Gly Pro Gly Ala Ser Ala Ala Ala Gly Gln Tyr Gly Pro
            325                 330                 335
Gly Gln Gln Gly Pro Gly Gln Tyr Gly Pro Gly Ser Ser Ala Ala Ala
            340                 345                 350
Ala Ala Gly Pro Gly Gln Gln Gly Pro Tyr Gly Pro Gly Ser Ser Ala
        355                 360                 365
Ala Ala Ala Gly Gln Tyr Gly Pro Gly Gln Gln Gly Pro Tyr Gly
    370                 375                 380
Pro Gly Gln Ser Ala Ala Ala Ala Gly Gln Tyr Gln Gln Gly Pro
385                 390                 395                 400
Gly Gln Gln Gly Pro Tyr Gly Pro Gly Ala Ser Ala Ala Ala Ala
            405                 410                 415
Gly Pro Gly Gln Gln Gly Pro Tyr Gly Pro Gly Ala Ser Ala Ala Ala
            420                 425                 430
```

Ala Ala Gly Pro Gly Gln Tyr Gly Pro Gly Gln Gly Pro Ser Ala
            435                 440                 445

Ser Ala Ala Ala Ala Gly Gln Tyr Gly Ser Gly Pro Gly Gln Tyr
        450                 455                 460

Gly Pro Tyr Gly Pro Gly Gln Ser Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gln Tyr Gly Pro Gln Gln Gly Pro Tyr Gly Pro
            500                 505                 510

Gly Gln Ser Ala Ala Ala Ala Gly Pro Gly Ser Gly Gln Tyr Gly
        515                 520                 525

Pro Gly Ala Ser Ala Ala Ala Ala Gly Gln Asn Gly Pro Gly Ser
        530                 535                 540

Gly Gln Tyr Gly Pro Gly Gln Gly Pro Gly Gln Ser Ala Ala Ala
545                 550                 555                 560

Ala Ala Gly Gln Tyr Gln Gln Gly Pro Gly Gln Gly Pro Tyr Gly
            565                 570                 575

Pro Gly Ala Ser Ala Ala Ala Ala Gly Pro Gly Ser Gly Gln Gln
        580                 585                 590

Gly Pro Gly Ala Ser
        595

<210> SEQ ID NO 9
<211> LENGTH: 590
<212> TYPE: PRT
<213> ORGANISM: Artificial Sequence
<220> FEATURE:
<223> OTHER INFORMATION: Met-PRT410: Met-CRY1_L_A5_giza_QQQ

<400> SEQUENCE: 9

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Gly Pro
50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gln Gly Pro Tyr Gly Ser Ala
        115                 120                 125

Ala Ala Ala Ala Gly Pro Gly Ser Gly Gln Tyr Gln Gln Gly Pro Tyr
            130                 135                 140

Gly Pro Gly Ala Ser Gly Pro Gly Gln Tyr Gly Pro Gly Gln Gln
145                 150                 155                 160

Pro Ser Ala Ser Ala Ala Ala Ala Gly Ser Gly Gln Gln Gly Pro
        165                 170                 175

Gly Gln Tyr Gly Pro Tyr Ala Ser Ala Ala Ala Ala Gly Gln Tyr
        180                 185                 190

```
Gly Ser Gly Pro Gln Gln Gly Pro Tyr Pro Gly Gln Ser Gly
        195                 200                 205
Ser Gly Gln Gln Gly Pro Gly Gln Gln Gly Pro Tyr Ala Ser Ala Ala
210                 215                 220
Ala Ala Ala Gly Pro Gly Gln Gln Gly Pro Tyr Gly Pro Gly Ser Ser
225                 230                 235                 240
Ala Ala Ala Ala Ala Gly Gln Tyr Gly Tyr Gly Pro Gly Gln Gly
            245                 250                 255
Pro Tyr Gly Pro Gly Ala Ser Gly Gln Asn Gly Pro Gly Ser Gly Gln
        260                 265                 270
Tyr Gly Pro Gly Gln Gln Gly Pro Gly Gln Ser Ala Ala Ala Ala Ala
    275                 280                 285
Gly Pro Gly Gln Gln Gly Pro Tyr Gly Pro Gly Ala Ser Ala Ala Ala
290                 295                 300
Ala Ala Gly Gln Tyr Gly Pro Gly Gln Gln Gly Pro Gly Gln Tyr Gly
305                 310                 315                 320
Pro Gly Ser Ser Gly Pro Gly Gln Gln Gly Pro Tyr Gly Pro Gly Ser
            325                 330                 335
Ser Ala Ala Ala Ala Gly Gln Tyr Gly Pro Gly Gln Gln Gly Pro
        340                 345                 350
Tyr Gly Pro Gly Gln Ser Ala Ala Ala Ala Gly Gln Tyr Gln Gln
    355                 360                 365
Gly Pro Gly Gln Gln Gly Pro Tyr Gly Pro Gly Ala Ser Gly Pro Gly
370                 375                 380
Gln Gln Gly Pro Tyr Gly Pro Gly Ala Ser Ala Ala Ala Ala Gly
385                 390                 395                 400
Pro Gly Gln Tyr Gly Pro Gly Gln Gln Gly Pro Ser Ala Ser Ala Ala
            405                 410                 415
Ala Ala Ala Gly Gln Tyr Gly Ser Gly Pro Gly Gln Tyr Gly Pro Tyr
        420                 425                 430
Gly Pro Gly Gln Ser Gly Pro Gly Ser Gly Gln Gln Gly Gln Gly Pro
    435                 440                 445
Tyr Gly Pro Gly Ala Ser Ala Ala Ala Ala Gly Gln Tyr Gly Pro
450                 455                 460
Gly Gln Gln Gly Pro Tyr Gly Pro Gly Gln Ser Ala Ala Ala Ala
465                 470                 475                 480
Gly Pro Gly Ser Gly Gln Tyr Gly Pro Gly Ala Ser Gly Gln Asn Gly
            485                 490                 495
Pro Gly Ser Gly Gln Tyr Gly Pro Gly Gln Gly Pro Gly Gln Ser
        500                 505                 510
Ala Ala Ala Ala Gly Gln Tyr Gln Gln Gly Pro Gly Gln Gln Gly
    515                 520                 525
Pro Tyr Gly Pro Gly Ala Ser Ala Ala Ala Ala Gly Gln Tyr Gly
530                 535                 540
Ser Gly Pro Gly Gln Gln Gly Pro Tyr Gly Pro Gly Gln Ser Gly Ser
545                 550                 555                 560
Gly Gln Gln Gly Pro Gly Gln Gln Gly Pro Tyr Ala Ser Ala Ala Ala
            565                 570                 575
Ala Ala Gly Pro Gly Ser Gly Gln Gln Gly Pro Gly Ala Ser
        580                 585                 590

<210> SEQ ID NO 10
<211> LENGTH: 565
<212> TYPE: PRT
```

<213> ORGANISM: Artificial Sequence
<220> FEATURE:
<223> OTHER INFORMATION: Met-PRT468: Met-CRY1_L_A7_giza_QQQ

<400> SEQUENCE: 10

```
Met Gly Pro Gly Gln Gln Gly Pro Tyr Gly Pro Gly Ala Ser Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gly Pro Gly Gln
            35                  40                  45

Gln Gly Pro Gly Ser Ser Ala Ala Ala Ala Ala Ala Gly Pro Gly
50                  55                  60

Gln Tyr Gly Pro Gly Gln Gln Gly Pro Ser Ala Ser Ala Ala Ala
65                  70                  75                  80

Ala Ala Ala Gly Pro Gly Ser Gly Gln Gln Gly Pro Gly Ala Ser Gly
            85                  90                  95

Gln Tyr Gly Pro Gly Gln Gln Gly Pro Gly Gln Gln Gly Pro Gly Ser
                100                 105                 110

Ser Ala Ala Ala Ala Ala Ala Gly Ser Tyr Gly Ser Gly Pro Gly
    115                 120                 125

Gln Gln Gly Pro Tyr Gly Ser Ala Ala Ala Ala Ala Ala Gly Pro
130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Gly Ser Tyr Gly Ser
            195                 200                 205

Gly Pro Gly Gln Gln Gly Pro Tyr Gly Pro Gly Gln Ser Gly Ser Gly
210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
            245                 250                 255

Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
            275                 280                 285

Gly Gln Tyr Gly Pro Gly Gln Gln Gly Pro Gly Ser Ala Ala Ala
    290                 295                 300

Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
            325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Ala Gly Ser
            355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
```

```
385                 390                 395                 400
Pro Tyr Gly Pro Gly Ala Ser Gly Pro Gly Gln Gln Gly Pro Tyr Gly
                405                 410                 415
Pro Gly Ala Ser Ala Ala Ala Ala Ala Ala Gly Pro Gly Gln Gln Tyr
            420                 425                 430
Gly Pro Gly Gln Gln Gly Pro Ser Ala Ser Ala Ala Ala Ala Ala Ala
        435                 440                 445
Ala Gly Ser Tyr Gly Ser Gly Pro Gly Gln Tyr Gly Pro Tyr Gly Pro
    450                 455                 460
Gly Gln Ser Gly Pro Gly Ser Gly Gln Gln Gly Gln Gly Pro Tyr Gly
465                 470                 475                 480
Pro Gly Ala Ser Ala Ala Ala Ala Ala Ala Gly Ser Tyr Gly Pro
                485                 490                 495
Gly Gln Gln Gly Pro Tyr Gly Pro Gly Pro Ser Ala Ala Ala Ala Ala
                500                 505                 510
Ala Ala Gly Pro Gly Ser Gly Gln Tyr Gly Pro Gly Ala Ser Gly Gln
            515                 520                 525
Asn Gly Pro Gly Ser Gly Gln Tyr Gly Pro Gly Gln Gln Gly Pro Gly
        530                 535                 540
Pro Ser Ala Ala Ala Ala Ala Ala Gly Pro Gly Ser Gly Gln Gln
545                 550                 555                 560
Gly Pro Gly Ala Ser
            565

<210> SEQ ID NO 11
<211> LENGTH: 2364
<212> TYPE: PRT
<213> ORGANISM: Artificial Sequence
<220> FEATURE:
<223> OTHER INFORMATION: Met-PRT799: Met-CRY1_200_A5_giza_QQQ_WHis6

<400> SEQUENCE: 11

Met Gly Pro Gly Gln Gln Gly Pro Tyr Gly Pro Gly Ala Ser Ala Ala
1               5                   10                  15
Ala Ala Ala Gly Gln Asn Gly Pro Gly Ser Gly Gln Gln Gly Pro Gly
            20                  25                  30
Gln Ser Gly Gln Tyr Gly Pro Gly Gln Gly Pro Gly Gln Gln Gly
        35                  40                  45
Pro Gly Ser Ser Ala Ala Ala Ala Gly Pro Gly Gln Tyr Gly Pro
    50                  55                  60
Gly Gln Gln Gly Pro Ser Ala Ser Ala Ala Ala Ala Gly Pro Gly
65                  70                  75                  80
Ser Gly Gln Gln Gly Pro Gly Ala Ser Gly Gln Tyr Gly Pro Gly Gln
                85                  90                  95
Gln Gly Pro Gly Gln Gln Gly Pro Gly Ser Ser Ala Ala Ala Ala Ala
            100                 105                 110
Gly Gln Tyr Gly Ser Gly Pro Gly Gln Gly Pro Tyr Gly Ser Ala
        115                 120                 125
Ala Ala Ala Ala Gly Pro Gly Ser Gly Gln Tyr Gly Gln Gly Pro Tyr
    130                 135                 140
Gly Pro Gly Ala Ser Gly Pro Gly Gln Tyr Gly Pro Gly Gln Gln Gly
145                 150                 155                 160
Pro Ser Ala Ser Ala Ala Ala Ala Gly Ser Gly Gln Gln Gly Pro
            165                 170                 175
Gly Gln Tyr Gly Pro Tyr Ala Ser Ala Ala Ala Ala Ala Gly Gln Tyr
```

```
                180               185                 190
Gly Ser Gly Pro Gly Gln Gln Gly Pro Tyr Gly Pro Gly Gln Ser Gly
            195                 200                 205
Ser Gly Gln Gln Gly Pro Gly Gln Gln Gly Pro Tyr Ala Ser Ala Ala
            210                 215                 220
Ala Ala Ala Gly Pro Gly Gln Gln Gly Pro Tyr Gly Pro Gly Ser Ser
225                 230                 235                 240
Ala Ala Ala Ala Ala Gly Gln Tyr Gly Tyr Gly Pro Gly Gln Gln Gly
                245                 250                 255
Pro Tyr Gly Pro Gly Ala Ser Gly Gln Asn Gly Pro Gly Ser Gly Gln
            260                 265                 270
Tyr Gly Pro Gly Gln Gln Gly Pro Gly Gln Ser Ala Ala Ala Ala Ala
            275                 280                 285
Gly Pro Gly Gln Gln Gly Pro Tyr Gly Pro Gly Ala Ser Ala Ala Ala
            290                 295                 300
Ala Ala Gly Gln Tyr Gly Pro Gly Gln Gln Gly Pro Gly Gln Tyr Gly
305                 310                 315                 320
Pro Gly Ser Ser Gly Pro Gly Gln Gln Gly Pro Tyr Gly Pro Gly Ser
                325                 330                 335
Ser Ala Ala Ala Ala Gly Gln Tyr Gly Pro Gly Gln Gln Gly Pro
            340                 345                 350
Tyr Gly Pro Gly Gln Ser Ala Ala Ala Ala Gly Gln Tyr Gln Gln
            355                 360                 365
Gly Pro Gly Gln Gln Gly Pro Tyr Gly Pro Gly Ala Ser Gly Pro Gly
            370                 375                 380
Gln Gln Gly Pro Tyr Gly Pro Gly Ala Ser Ala Ala Ala Ala Gly
385                 390                 395                 400
Pro Gly Gln Tyr Gly Pro Gly Gln Gln Gly Pro Ser Ala Ser Ala Ala
                405                 410                 415
Ala Ala Ala Gly Gln Tyr Gly Ser Gly Pro Gly Gln Tyr Gly Pro Tyr
                420                 425                 430
Gly Pro Gly Gln Ser Gly Pro Gly Ser Gly Gln Gln Gly Gln Gly Pro
            435                 440                 445
Tyr Gly Pro Gly Ala Ser Ala Ala Ala Ala Gly Gln Tyr Gly Pro
            450                 455                 460
Gly Gln Gln Gly Pro Tyr Gly Pro Gly Gln Ser Ala Ala Ala Ala
465                 470                 475                 480
Gly Pro Gly Ser Gly Gln Tyr Gly Pro Gly Ala Ser Gly Gln Asn Gly
                485                 490                 495
Pro Gly Ser Gly Gln Tyr Gly Pro Gly Gln Gly Pro Gly Gln Ser
            500                 505                 510
Ala Ala Ala Ala Gly Gln Tyr Gln Gln Gly Pro Gly Gln Gln Gly
            515                 520                 525
Pro Tyr Gly Pro Gly Ala Ser Ala Ala Ala Ala Gly Gln Tyr Gly
            530                 535                 540
Ser Gly Pro Gly Gln Gln Gly Pro Tyr Gly Pro Gly Gln Ser Gly Ser
545                 550                 555                 560
Gly Gln Gln Gly Pro Gly Gln Gln Gly Pro Tyr Ala Ser Ala Ala Ala
                565                 570                 575
Ala Ala Gly Pro Gly Ser Gly Gln Gln Gly Pro Gly Ala Ser Gly Gln
            580                 585                 590
Gln Gly Pro Tyr Gly Pro Gly Ala Ser Ala Ala Ala Ala Gly Gln
            595                 600                 605
```

```
Asn Gly Pro Gly Ser Gly Gln Gln Gly Pro Gly Gln Ser Gly Gln Tyr
    610                 615                 620
Gly Pro Gly Gln Gln Gly Pro Gly Gln Gln Gly Pro Gly Ser Ser Ala
625                 630                 635                 640
Ala Ala Ala Ala Gly Pro Gly Gln Tyr Gly Pro Gly Gln Gln Gly Pro
                645                 650                 655
Ser Ala Ser Ala Ala Ala Ala Gly Pro Gly Ser Gly Gln Gln Gly
            660                 665                 670
Pro Gly Ala Ser Gly Gln Tyr Gly Pro Gly Gln Gln Gly Pro Gly Gln
        675                 680                 685
Gln Gly Pro Gly Ser Ser Ala Ala Ala Ala Gly Gln Tyr Gly Ser
690                 695                 700
Gly Pro Gly Gln Gln Gly Pro Tyr Gly Ser Ala Ala Ala Ala Gly
705                 710                 715                 720
Pro Gly Ser Gly Gln Tyr Gly Gln Gly Pro Tyr Gly Pro Gly Ala Ser
                725                 730                 735
Gly Pro Gly Gln Tyr Gly Pro Gly Gln Gln Gly Pro Ser Ala Ser Ala
            740                 745                 750
Ala Ala Ala Ala Gly Ser Gly Gln Gln Gly Pro Gly Gln Tyr Gly Pro
        755                 760                 765
Tyr Ala Ser Ala Ala Ala Ala Gly Gln Tyr Gly Ser Gly Pro Gly
770                 775                 780
Gln Gln Gly Pro Tyr Gly Pro Gly Gln Ser Gly Ser Gly Gln Gln Gly
785                 790                 795                 800
Pro Gly Gln Gln Gly Pro Tyr Ala Ser Ala Ala Ala Ala Gly Pro
                805                 810                 815
Gly Gln Gln Gly Pro Tyr Gly Pro Gly Ser Ser Ala Ala Ala Ala
            820                 825                 830
Gly Gln Tyr Gly Tyr Gly Pro Gly Gln Gln Gly Pro Tyr Gly Pro Gly
        835                 840                 845
Ala Ser Gly Gln Asn Gly Pro Gly Ser Gly Gln Tyr Gly Pro Gly Gln
        850                 855                 860
Gln Gly Pro Gly Gln Ser Ala Ala Ala Ala Gly Pro Gly Gln Gln
865                 870                 875                 880
Gly Pro Tyr Gly Pro Gly Ala Ser Ala Ala Ala Ala Gly Gln Tyr
                885                 890                 895
Gly Pro Gly Gln Gln Gly Pro Gly Gln Tyr Gly Pro Gly Ser Ser Gly
            900                 905                 910
Pro Gly Gln Gln Gly Pro Tyr Gly Pro Gly Ser Ser Ala Ala Ala
        915                 920                 925
Ala Gly Gln Tyr Gly Pro Gly Gln Gln Gly Pro Tyr Gly Pro Gly Gln
        930                 935                 940
Ser Ala Ala Ala Ala Gly Gln Tyr Gln Gly Pro Gly Gln Gln
945                 950                 955                 960
Gly Pro Tyr Gly Pro Gly Ala Ser Gly Pro Gly Gln Gln Gly Pro Tyr
                965                 970                 975
Gly Pro Gly Ala Ser Ala Ala Ala Ala Gly Pro Gly Gln Tyr Gly
            980                 985                 990
Pro Gly Gln Gln Gly Pro Ser Ala  Ser Ala Ala Ala Ala  Ala Gly Gln
        995                 1000                1005
Tyr Gly  Ser Gly Pro Gly Gln  Tyr Gly Pro Tyr Gly  Pro Gly Gln
    1010                1015                1020
```

```
Ser Gly  Pro Gly Ser Gly Gln  Gln Gly Gln Gly Pro  Tyr Gly Pro
    1025             1030                 1035

Gly Ala  Ser Ala Ala Ala Ala  Ala Gly Gln Tyr Gly  Pro Gly Gln
    1040             1045                 1050

Gln Gly  Pro Tyr Gly Pro Gly  Gln Ser Ala Ala Ala  Ala Ala Gly
    1055             1060                 1065

Pro Gly  Ser Gly Gln Tyr Gly  Pro Gly Ala Ser Gly  Gln Asn Gly
    1070             1075                 1080

Pro Gly  Ser Gly Gln Tyr Gly  Pro Gly Gln Gly Gly  Pro Gly Gln
    1085             1090                 1095

Ser Ala  Ala Ala Ala Ala Gly  Gln Tyr Gln Gln Gly  Pro Gly Gln
    1100             1105                 1110

Gln Gly  Pro Tyr Gly Pro Gly  Ala Ser Ala Ala Ala  Ala Ala Gly
    1115             1120                 1125

Gln Tyr  Gly Ser Gly Pro Gly  Gln Gln Gly Pro Tyr  Gly Pro Gly
    1130             1135                 1140

Gln Ser  Gly Ser Gly Gln Gln  Gly Pro Gly Gln Gln  Gly Pro Tyr
    1145             1150                 1155

Ala Ser  Ala Ala Ala Ala Ala  Gly Pro Gly Ser Gly  Gln Gln Gly
    1160             1165                 1170

Pro Gly  Ala Ser Gly Gln Gln  Gly Pro Tyr Gly Pro  Gly Ala Ser
    1175             1180                 1185

Ala Ala  Ala Ala Ala Gly Gln  Asn Gly Pro Gly Ser  Gly Gln Gln
    1190             1195                 1200

Gly Pro  Gly Gln Ser Gly Gln  Tyr Gly Pro Gly Gln  Gln Gly Pro
    1205             1210                 1215

Gly Gln  Gln Gly Pro Gly Ser  Ser Ala Ala Ala Ala  Ala Gly Pro
    1220             1225                 1230

Gly Gln  Tyr Gly Pro Gly Gln  Gln Gly Pro Ser Ala  Ser Ala Ala
    1235             1240                 1245

Ala Ala  Ala Gly Pro Gly Ser  Gly Gln Gln Gly Pro  Gly Ala Ser
    1250             1255                 1260

Gly Gln  Tyr Gly Pro Gly Gln  Gln Gly Pro Gly Gln  Gln Gly Pro
    1265             1270                 1275

Gly Ser  Ser Ala Ala Ala Ala  Ala Gly Gln Tyr Gly  Ser Gly Pro
    1280             1285                 1290

Gly Gln  Gln Gly Pro Tyr Gly  Ser Ala Ala Ala Ala  Ala Gly Pro
    1295             1300                 1305

Gly Ser  Gly Gln Tyr Gly Gln  Gly Pro Tyr Gly Pro  Gly Ala Ser
    1310             1315                 1320

Gly Pro  Gly Gln Tyr Gly Pro  Gly Gln Gln Gly Pro  Ser Ala Ser
    1325             1330                 1335

Ala Ala  Ala Ala Ala Gly Ser  Gly Gln Gln Gly Pro  Gly Gln Tyr
    1340             1345                 1350

Gly Pro  Tyr Ala Ser Ala Ala  Ala Ala Ala Gly Gln  Tyr Gly Ser
    1355             1360                 1365

Gly Pro  Gly Gln Gln Gly Pro  Tyr Gly Pro Gly Gln  Ser Gly Ser
    1370             1375                 1380

Gly Gln  Gln Gly Pro Gly Gln  Gln Gly Pro Tyr Ala  Ser Ala Ala
    1385             1390                 1395

Ala Ala  Ala Gly Pro Gly Gln  Gln Gly Pro Tyr Gly  Pro Gly Ser
    1400             1405                 1410

Ser Ala  Ala Ala Ala Ala Gly  Gln Tyr Gly Tyr Gly  Pro Gly Gln
```

```
                1415                1420                1425

Gln Gly Pro Tyr Gly Pro Gly Ala Ser Gly Gln Asn Gly Pro Gly
        1430                1435                1440

Ser Gly Gln Tyr Gly Pro Gly Gln Gly Pro Gly Gln Ser Ala
        1445                1450                1455

Ala Ala Ala Ala Gly Pro Gly Gln Gly Pro Tyr Gly Pro Gly
        1460                1465                1470

Ala Ser Ala Ala Ala Ala Gly Gln Tyr Gly Pro Gly Gln Gln
        1475                1480                1485

Gly Pro Gly Gln Tyr Gly Pro Gly Ser Ser Gly Pro Gly Gln Gln
        1490                1495                1500

Gly Pro Tyr Gly Pro Gly Ser Ser Ala Ala Ala Ala Gly Gln
        1505                1510                1515

Tyr Gly Pro Gly Gln Gln Gly Pro Tyr Gly Pro Gly Gln Ser Ala
        1520                1525                1530

Ala Ala Ala Gly Gln Tyr Gln Gln Gly Pro Gly Gln Gln Gly
        1535                1540                1545

Pro Tyr Gly Pro Gly Ala Ser Gly Pro Gly Gln Gln Gly Pro Tyr
        1550                1555                1560

Gly Pro Gly Ala Ser Ala Ala Ala Ala Gly Pro Gly Gln Tyr
        1565                1570                1575

Gly Pro Gly Gln Gln Gly Pro Ser Ala Ser Ala Ala Ala Ala Ala
        1580                1585                1590

Gly Gln Tyr Gly Ser Gly Pro Gly Gln Tyr Gly Pro Tyr Gly Pro
        1595                1600                1605

Gly Gln Ser Gly Pro Gly Ser Gly Gln Gln Gly Gln Gly Pro Tyr
        1610                1615                1620

Gly Pro Gly Ala Ser Ala Ala Ala Ala Gly Gln Tyr Gly Pro
        1625                1630                1635

Gly Gln Gln Gly Pro Tyr Gly Pro Gly Gln Ser Ala Ala Ala Ala
        1640                1645                1650

Ala Gly Pro Gly Ser Gly Gln Tyr Gly Pro Gly Ala Ser Gly Gln
        1655                1660                1665

Asn Gly Pro Gly Ser Gly Gln Tyr Gly Pro Gly Gln Gln Gly Pro
        1670                1675                1680

Gly Gln Ser Ala Ala Ala Ala Gly Gln Tyr Gln Gln Gly Pro
        1685                1690                1695

Gly Gln Gln Gly Pro Tyr Gly Pro Gly Ala Ser Ala Ala Ala Ala
        1700                1705                1710

Ala Gly Gln Tyr Gly Ser Gly Pro Gly Gln Gln Gly Pro Tyr Gly
        1715                1720                1725

Pro Gly Gln Ser Gly Ser Gly Gln Gln Gly Pro Gly Gln Gln Gly
        1730                1735                1740

Pro Tyr Ala Ser Ala Ala Ala Ala Gly Pro Gly Ser Gly Gln
        1745                1750                1755

Gln Gly Pro Gly Ala Ser Gly Gln Gln Gly Pro Tyr Gly Pro Gly
        1760                1765                1770

Ala Ser Ala Ala Ala Ala Ala Gly Gln Asn Gly Pro Gly Ser Gly
        1775                1780                1785

Gln Gln Gly Pro Gly Gln Ser Gly Gln Tyr Gly Pro Gly Gln Gln
        1790                1795                1800

Gly Pro Gly Gln Gln Gly Pro Gly Ser Ser Ala Ala Ala Ala Ala
        1805                1810                1815
```

```
Gly Pro Gly Gln Tyr Gly Pro Gly Gln Gln Gly Pro  Ser Ala Ser
        1820                1825                1830

Ala Ala  Ala Ala Ala Gly Pro  Gly Ser Gly Gln Gln  Gly Pro Gly
        1835                1840                1845

Ala Ser  Gly Gln Tyr Gly Pro  Gly Gln Gln Gly Pro  Gly Gln Gln
        1850                1855                1860

Gly Pro  Gly Ser Ser Ala Ala  Ala Ala Gly Gln Tyr  Gly Ser
        1865                1870                1875

Gly Pro  Gly Gln Gln Gly Pro  Tyr Gly Ser Ala Ala  Ala Ala Ala
        1880                1885                1890

Gly Pro  Gly Ser Gly Gln Tyr  Gly Gln Gly Pro Tyr  Gly Pro Gly
        1895                1900                1905

Ala Ser  Gly Pro Gly Gln Tyr  Gly Pro Gly Gln Gln  Gly Pro Ser
        1910                1915                1920

Ala Ser  Ala Ala Ala Ala Ala  Gly Ser Gly Gln Gln  Gly Pro Gly
        1925                1930                1935

Gln Tyr  Gly Pro Tyr Ala Ser  Ala Ala Ala Ala Ala  Gly Gln Tyr
        1940                1945                1950

Gly Ser  Gly Pro Gly Gln Gln  Gly Pro Tyr Gly Pro  Gly Gln Ser
        1955                1960                1965

Gly Ser  Gly Gln Gln Gly Pro  Gly Gln Gln Gly Pro  Tyr Ala Ser
        1970                1975                1980

Ala Ala  Ala Ala Ala Gly Pro  Gly Gln Gln Gly Pro  Tyr Gly Pro
        1985                1990                1995

Gly Ser  Ser Ala Ala Ala Ala  Ala Gly Gln Tyr Gly  Tyr Gly Pro
        2000                2005                2010

Gly Gln  Gln Gly Pro Tyr Gly  Pro Gly Ala Ser Gly  Gln Asn Gly
        2015                2020                2025

Pro Gly  Ser Gly Gln Tyr Gly  Pro Gly Gln Gln Gly  Pro Gly Gln
        2030                2035                2040

Ser Ala  Ala Ala Ala Ala Gly  Pro Gly Gln Gln Gly  Pro Tyr Gly
        2045                2050                2055

Pro Gly  Ala Ser Ala Ala Ala  Ala Ala Gly Gln Tyr  Gly Pro Gly
        2060                2065                2070

Gln Gln  Gly Pro Gly Gln Tyr  Gly Pro Gly Ser Ser  Gly Pro Gly
        2075                2080                2085

Gln Gln  Gly Pro Tyr Gly Pro  Gly Ser Ser Ala Ala  Ala Ala Ala
        2090                2095                2100

Gly Gln  Tyr Gly Pro Gly Gln  Gln Gly Pro Tyr Gly  Pro Gly Gln
        2105                2110                2115

Ser Ala  Ala Ala Ala Ala Gly  Gln Tyr Gln Gln Gly  Pro Gly Gln
        2120                2125                2130

Gln Gly  Pro Tyr Gly Pro Gly  Ala Ser Gly Pro Gly  Gln Gln Gly
        2135                2140                2145

Pro Tyr  Gly Pro Gly Ala Ser  Ala Ala Ala Ala Ala  Gly Pro Gly
        2150                2155                2160

Gln Tyr  Gly Pro Gly Gln Gln  Gly Pro Ser Ala Ser  Ala Ala Ala
        2165                2170                2175

Ala Ala  Gly Gln Tyr Gly Ser  Gly Pro Gly Gln Tyr  Gly Pro Tyr
        2180                2185                2190

Gly Pro  Gly Gln Ser Gly Pro  Gly Ser Gly Gln Gln  Gly Gln Gly
        2195                2200                2205
```

```
Pro Tyr Gly Pro Gly Ala Ser Ala Ala Ala Ala Gly Gln Tyr
    2210            2215                2220

Gly Pro Gly Gln Gln Gly Pro Tyr Gly Pro Gly Gln Ser Ala Ala
    2225            2230                2235

Ala Ala Ala Gly Pro Gly Ser Gly Gln Tyr Gly Pro Gly Ala Ser
    2240            2245                2250

Gly Gln Asn Gly Pro Gly Ser Gly Gln Tyr Gly Pro Gly Gln Gln
    2255            2260                2265

Gly Pro Gly Gln Ser Ala Ala Ala Ala Gly Gln Tyr Gln Gln
    2270            2275                2280

Gly Pro Gly Gln Gln Gly Pro Tyr Gly Pro Gly Ala Ser Ala Ala
    2285            2290                2295

Ala Ala Ala Gly Gln Tyr Gly Ser Gly Pro Gly Gln Gln Gly Pro
    2300            2305                2310

Tyr Gly Pro Gly Gln Ser Gly Ser Gly Gln Gln Gly Pro Gly Gln
    2315            2320                2325

Gln Gly Pro Tyr Ala Ser Ala Ala Ala Ala Gly Pro Gly Ser
    2330            2335                2340

Gly Gln Gln Gly Ser Ser Val Asp Lys Leu Ala Ala Ala Leu Glu
    2345            2350                2355

His His His His His His
    2360

<210> SEQ ID NO 12
<211> LENGTH: 608
<212> TYPE: PRT
<213> ORGANISM: Artificial Sequence
<220> FEATURE:
<223> OTHER INFORMATION: PRT313

<400> SEQUENCE: 12

Met His His His His His Ser Ser Gly Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Ser Ala Ala Ala
            35                  40                  45

Ala Ala Gly Gly Tyr Gly Pro Gly Gln Pro Gly Gln Gln Gly
        50                  55                  60

Pro Gly Ser Ser Ala Ala Ala Ala Gly Pro Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
            100                 105                 110

Tyr Gly Pro Gly Gly Gln Gly Pro Gln Gln Gly Pro Gly Ser Ser
        115                 120                 125

Ala Ala Ala Ala Ala Gly Gly Tyr Gly Ser Gly Pro Gly Gln Gly
    130                 135                 140

Pro Tyr Gly Ser Ala Ala Ala Ala Gly Pro Gly Ser Gly Gly Tyr
145                 150                 155                 160

Gly Gln Gly Pro Tyr Gly Pro Gly Ala Ser Ala Ala Ala Ala Gly
                165                 170                 175

Pro Gly Gly Tyr Gly Pro Gly Gln Gly Pro Ser Ala Ser Ala Ala
            180                 185                 190
```

Ala Ala Ala Gly Ser Gly Gln Gln Gly Pro Gly Tyr Gly Pro Tyr
            195                 200                 205

Ala Ser Ala Ala Ala Ala Gly Gly Tyr Gly Ser Gly Pro Gly Gln
210                 215                 220

Gln Gly Pro Tyr Gly Pro Gly Gly Ser Ala Ala Ala Ala Gly Ser
225                 230                 235                 240

Gly Gln Gln Gly Pro Gly Gln Gly Pro Tyr Ala Ser Ala Ala Ala
                245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
            275                 280                 285

Tyr Gly Pro Gly Ala Ser Ala Ala Ala Ala Gly Gly Asn Gly Pro
290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
                325                 330                 335

Ser Ala Ala Ala Ala Gly Gly Tyr Gly Pro Gly Gly Gln Gly Pro
            340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Gly
            370                 375                 380

Gly Tyr Gly Pro Gly Gln Gln Gly Pro Tyr Gly Pro Gly Gly Ser Ala
385                 390                 395                 400

Ala Ala Ala Gly Gly Tyr Gln Gln Gly Pro Gly Gly Gln Gly Pro
                405                 410                 415

Tyr Gly Pro Gly Ala Ser Ala Ala Ala Ala Gly Pro Gly Gly Gln
            420                 425                 430

Gly Pro Tyr Gly Pro Gly Ala Ser Ala Ala Ala Ala Gly Pro Gly
            435                 440                 445

Gly Tyr Gly Pro Gly Gly Gln Gly Pro Ser Ala Ser Ala Ala Ala
            450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Gly Pro Gly Ser Gly Gln Gln Gly
                485                 490                 495

Gln Gly Pro Tyr Gly Pro Gly Ala Ser Ala Ala Ala Ala Gly Gly
            500                 505                 510

Tyr Gly Pro Gly Gln Gln Gly Pro Tyr Gly Pro Gly Gly Ser Ala Ala
            515                 520                 525

Ala Ala Ala Gly Pro Gly Ser Gly Tyr Gly Pro Gly Ala Ser Ala
530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Gly Gly Tyr
                565                 570                 575

Gln Gln Gly Pro Gly Gly Gln Gly Pro Tyr Gly Pro Gly Ala Ser Ala
            580                 585                 590

Ala Ala Ala Gly Pro Gly Ser Gly Gln Gln Gly Pro Gly Ala Ser
                595                 600                 605

```
<210> SEQ ID NO 13
<211> LENGTH: 601
<212> TYPE: PRT
<213> ORGANISM: Artificial Sequence
<220> FEATURE:
<223> OTHER INFORMATION: PRT399

<400> SEQUENCE: 13

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Gly Tyr
        35                  40                  45

Gly Pro Gly Gly Gln Gly Pro Gly Gln Gln Gly Pro Gly Ser Ser Ala
    50                  55                  60

Ala Ala Ala Ala Gly Pro Gly Tyr Gly Pro Gly Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gly Tyr Gly Pro Gly Gln Gly Pro Gly Gln
            100                 105                 110

Gln Gly Pro Gly Ser Ser Ala Ala Ala Ala Gly Gly Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gln Gly Pro Ser Ala Ser Ala
            165                 170                 175

Ala Ala Ala Gly Ser Gly Gln Gln Gly Pro Gly Gly Tyr Gly Pro
            180                 185                 190

Tyr Ala Ser Ala Ala Ala Ala Gly Gly Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala
            245                 250                 255

Gly Gly Tyr Gly Tyr Gly Pro Gly Gly Gln Gly Pro Tyr Gly Pro Gly
            260                 265                 270

Ala Ser Gly Gly Asn Gly Pro Gly Ser Gly Tyr Gly Pro Gly Gln
            275                 280                 285

Gln Gly Pro Gly Gly Ser Ala Ala Ala Ala Gly Pro Gly Gly Gln
            290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
            325                 330                 335

Pro Gly Gly Gln Gly Pro Tyr Gly Pro Gly Ser Ser Ala Ala Ala
            340                 345                 350

Ala Gly Gly Tyr Gly Pro Gly Gln Gln Gly Pro Tyr Gly Pro Gly Gly
            355                 360                 365

Ser Ala Ala Ala Ala Ala Gly Gly Tyr Gln Gln Gly Pro Gly Gly Gln
```

```
                    370                 375                 380
Gly Pro Tyr Gly Pro Gly Ala Ser Gly Pro Gly Gln Gly Pro Tyr
385                 390                 395                 400

Gly Pro Gly Ala Ser Ala Ala Ala Ala Gly Pro Gly Gly Tyr Gly
                405                 410                 415

Pro Gly Gly Gln Gly Pro Ser Ala Ser Ala Ala Ala Ala Gly Gly
                420                 425                 430

Tyr Gly Ser Gly Pro Gly Tyr Gly Pro Tyr Gly Pro Gly Gly Ser
                435                 440                 445

Gly Pro Gly Ser Gly Gln Gln Gly Gln Gly Pro Tyr Gly Pro Ala
                450                 455                 460

Ser Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
                485                 490                 495

Gly Tyr Gly Pro Gly Ala Ser Gly Gly Asn Gly Pro Gly Ser Gly
                500                 505                 510

Tyr Gly Pro Gly Gln Gln Gly Pro Gly Gly Ser Ala Ala Ala Ala
                515                 520                 525

Gly Gly Tyr Gln Gln Gly Pro Gly Gly Gln Gly Pro Tyr Gly Pro Gly
                530                 535                 540

Ala Ser Ala Ala Ala Ala Gly Gly Tyr Gly Ser Gly Pro Gly Gln
545                 550                 555                 560

Gln Gly Pro Tyr Gly Pro Gly Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser
                595                 600

<210> SEQ ID NO 14
<211> LENGTH: 608
<212> TYPE: PRT
<213> ORGANISM: Artificial Sequence
<220> FEATURE:
<223> OTHER INFORMATION: PRT380

<400> SEQUENCE: 14

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Ala Ala
                35                  40                  45

Ala Ala Gly Gln Tyr Gly Pro Gly Gln Gln Gly Pro Gly Gln Gln Gly
    50                  55                  60

Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gln
                100                 105                 110

Tyr Gly Pro Gly Gln Gln Gly Pro Gly Gln Gln Gly Pro Gly Ser Ser
                115                 120                 125

Ala Ala Ala Ala Ala Gly Gln Tyr Gly Ser Gly Pro Gly Gln Gln Gly
```

-continued

```
            130                 135                 140
Pro Tyr Gly Ser Ala Ala Ala Gly Pro Gly Ser Gln Tyr
145                 150                 155                 160
Gly Gln Gly Pro Tyr Gly Pro Gly Ala Ser Ala Ala Ala Gly
                165                 170                 175
Pro Gly Gln Tyr Gly Pro Gly Gln Gln Gly Pro Ser Ala Ser Ala Ala
                180                 185                 190
Ala Ala Ala Gly Ser Gln Gln Gly Pro Gly Gln Tyr Gly Pro Tyr
                195                 200                 205
Ala Ser Ala Ala Ala Ala Gly Gln Tyr Gly Ser Gly Pro Gly Gln
            210                 215                 220
Gln Gly Pro Tyr Gly Pro Gln Ser Ala Ala Ala Ala Gly Ser
225                 230                 235                 240
Gly Gln Gln Gly Pro Gln Gln Gly Pro Tyr Ala Ser Ala Ala Ala
                245                 250                 255
Ala Ala Gly Pro Gly Gln Gln Gly Pro Tyr Gly Pro Gly Ser Ser Ala
                260                 265                 270
Ala Ala Ala Gly Gln Tyr Gly Tyr Gly Pro Gly Gln Gln Gly Pro
                275                 280                 285
Tyr Gly Pro Gly Ala Ser Ala Ala Ala Ala Gly Gln Asn Gly Pro
            290                 295                 300
Gly Ser Gly Gln Tyr Gly Pro Gly Gln Gln Gly Pro Gln Ser Ala
305                 310                 315                 320
Ala Ala Ala Gly Pro Gly Gln Gln Gly Pro Tyr Gly Pro Gly Ala
                325                 330                 335
Ser Ala Ala Ala Ala Gly Gln Tyr Gly Pro Gly Gln Gln Gly Pro
                340                 345                 350
Gly Gln Tyr Gly Pro Gly Ser Ser Ala Ala Ala Ala Gly Pro Gly
                355                 360                 365
Gln Gln Gly Pro Tyr Gly Pro Gly Ser Ser Ala Ala Ala Ala Gly
            370                 375                 380
Gln Tyr Gly Pro Gly Gln Gln Gly Pro Tyr Gly Pro Gly Gln Ser Ala
385                 390                 395                 400
Ala Ala Ala Gly Gln Tyr Gln Gln Gly Pro Gly Gln Gln Gly Pro
                405                 410                 415
Tyr Gly Pro Gly Ala Ser Ala Ala Ala Ala Gly Pro Gly Gln Gln
                420                 425                 430
Gly Pro Tyr Gly Pro Gly Ala Ser Ala Ala Ala Ala Gly Pro Gly
                435                 440                 445
Gln Tyr Gly Pro Gly Gln Gln Gly Pro Ser Ala Ser Ala Ala Ala
            450                 455                 460
Ala Gly Gln Tyr Gly Ser Gly Pro Gly Gln Tyr Gly Pro Tyr Gly Pro
465                 470                 475                 480
Gly Gln Ser Ala Ala Ala Ala Gly Pro Gly Ser Gly Gln Gln Gly
                485                 490                 495
Gln Gly Pro Tyr Gly Pro Gly Ala Ser Ala Ala Ala Ala Gly Gln
                500                 505                 510
Tyr Gly Pro Gly Gln Gln Gly Pro Tyr Gly Pro Gly Gln Ser Ala Ala
            515                 520                 525
Ala Ala Ala Gly Pro Gly Ser Gly Gln Tyr Gly Pro Gly Ala Ser Ala
            530                 535                 540
Ala Ala Ala Gly Gln Asn Gly Pro Gly Ser Gly Gln Tyr Gly Pro
545                 550                 555                 560
```

```
Gly Gln Gln Gly Pro Gly Gln Ser Ala Ala Ala Gly Gln Tyr
                565                 570                 575

Gln Gln Gly Pro Gly Gln Gly Pro Tyr Gly Pro Gly Ala Ser Ala
            580                 585                 590

Ala Ala Ala Ala Gly Pro Gly Ser Gly Gln Gly Pro Gly Ala Ser
            595                 600             605
```

<210> SEQ ID NO 15
<211> LENGTH: 601
<212> TYPE: PRT
<213> ORGANISM: Artificial Sequence
<220> FEATURE:
<223> OTHER INFORMATION: PRT410

<400> SEQUENCE: 15

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
            290                 295                 300

Gly Pro Tyr Gly Pro Gly Ala Ser Ala Ala Ala Ala Gly Gln Tyr
305                 310                 315                 320
```

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gln Gly Pro Gly Gln Gln
        370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
            435                 440                 445

Gly Pro Gly Ser Gly Gln Gln Gly Gln Gly Pro Tyr Gly Pro Gly Ala
        450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gly Pro Gly Gln Ser Ala Ala Ala Ala
            515                 520                 525

Gly Gln Tyr Gln Gln Gly Pro Gly Gln Gln Gly Pro Tyr Gly Pro Gly
        530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600

<210> SEQ ID NO 16
<211> LENGTH: 576
<212> TYPE: PRT
<213> ORGANISM: Artificial Sequence
<220> FEATURE:
<223> OTHER INFORMATION: PRT468

<400> SEQUENCE: 16

Met His His His His His Ser Ser Gly Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
        50                  55                  60

Ser Ala Ala Ala Ala Ala Ala Ala Gly Pro Gly Gln Tyr Gly Pro Gly
65                  70                  75                  80

```
Gln Gln Gly Pro Ser Ala Ser Ala Ala Ala Ala Ala Gly Pro
                85                  90                  95
Gly Ser Gly Gln Gln Gly Pro Gly Ala Ser Gly Gln Tyr Gly Pro Gly
            100                 105                 110
Gln Gln Gly Pro Gly Gln Gln Gly Pro Gly Ser Ser Ala Ala Ala
            115                 120                 125
Ala Ala Ala Gly Ser Tyr Gly Ser Gly Pro Gly Gln Gln Gly Pro Tyr
130                 135                 140
Gly Ser Ala Ala Ala Ala Ala Ala Gly Pro Gly Ser Gly Gln Tyr
145                 150                 155                 160
Gly Gln Gly Pro Tyr Gly Pro Gly Ala Ser Gly Pro Gly Gln Tyr Gly
                165                 170                 175
Pro Gly Gln Gln Gly Pro Ser Ala Ser Ala Ala Ala Ala Ala Ala
            180                 185                 190
Gly Ser Gly Gln Gln Gly Pro Gly Gln Tyr Gly Pro Tyr Ala Ser Ala
            195                 200                 205
Ala Ala Ala Ala Ala Ala Gly Ser Tyr Gly Ser Gly Pro Gly Gln Gln
210                 215                 220
Gly Pro Tyr Gly Pro Gly Gln Ser Gly Ser Gly Gln Gln Gly Pro Gly
225                 230                 235                 240
Gln Gln Gly Pro Tyr Ala Ser Ala Ala Ala Ala Ala Ala Gly Pro
            245                 250                 255
Gly Gln Gln Gly Pro Tyr Gly Pro Gly Ser Ser Ala Ala Ala Ala Ala
            260                 265                 270
Ala Ala Gly Ser Tyr Gly Tyr Gly Pro Gly Gln Gln Gly Pro Tyr Gly
            275                 280                 285
Pro Gly Ala Ser Gly Gln Asn Gly Pro Gly Ser Gly Gln Tyr Gly Pro
290                 295                 300
Gly Gln Gln Gly Pro Gly Pro Ser Ala Ala Ala Ala Ala Ala Gly
305                 310                 315                 320
Pro Gly Gln Gln Gly Pro Tyr Gly Pro Gly Ala Ser Ala Ala Ala Ala
            325                 330                 335
Ala Ala Ala Gly Ser Tyr Gly Pro Gly Gln Gln Gly Pro Gly Gln Tyr
            340                 345                 350
Gly Pro Gly Ser Ser Gly Pro Gly Gln Gln Gly Pro Tyr Gly Pro Gly
            355                 360                 365
Ser Ser Ala Ala Ala Ala Ala Ala Gly Ser Tyr Gly Pro Gly Gln
370                 375                 380
Gln Gly Pro Tyr Gly Pro Gly Pro Ser Ala Ala Ala Ala Ala Ala Ala
385                 390                 395                 400
Gly Ser Tyr Gln Gln Gly Pro Gly Gln Gln Gly Pro Tyr Gly Pro Gly
            405                 410                 415
Ala Ser Gly Pro Gly Gln Gln Gly Pro Tyr Gly Pro Gly Ala Ser Ala
            420                 425                 430
Ala Ala Ala Ala Ala Ala Gly Pro Gly Gln Tyr Gly Pro Gly Gln Gln
            435                 440                 445
Gly Pro Ser Ala Ser Ala Ala Ala Ala Ala Ala Gly Ser Tyr Gly
450                 455                 460
Ser Gly Pro Gly Gln Tyr Gly Pro Tyr Gly Pro Gly Gln Ser Gly Pro
465                 470                 475                 480
Gly Ser Gly Gln Gln Gly Gln Gly Pro Tyr Gly Pro Gly Ala Ser Ala
            485                 490                 495
```

```
Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
            530                 535                 540

Gly Gln Tyr Gly Pro Gly Gln Gly Pro Gly Pro Ser Ala Ala Ala
545                 550                 555                 560

Ala Ala Ala Ala Gly Pro Gly Ser Gly Gln Gln Gly Pro Gly Ala Ser
            565                 570                 575

<210> SEQ ID NO 17
<211> LENGTH: 2375
<212> TYPE: PRT
<213> ORGANISM: Artificial Sequence
<220> FEATURE:
<223> OTHER INFORMATION: PRT799

<400> SEQUENCE: 17

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gly Pro Gly Ser Ser Ala
            50                  55                  60

Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gly Pro Ser Ala Ser Ala
            165                 170                 175

Ala Ala Ala Gly Ser Gly Gln Gln Gly Pro Gly Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285
```

-continued

```
Gln Gly Pro Gly Gln Ser Ala Ala Ala Ala Gly Pro Gly Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala
                340                 345                 350

Ala Gly Gln Tyr Gly Pro Gly Gln Gln Gly Pro Tyr Gly Pro Gly Gln
                355                 360                 365

Ser Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
                435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
                500                 505                 510

Tyr Gly Pro Gly Gln Gln Gly Pro Gly Gln Ser Ala Ala Ala Ala
                515                 520                 525

Gly Gln Tyr Gln Gln Gly Pro Gly Gln Gln Gly Pro Tyr Gly Pro Gly
    530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser Gly Gln Gln Gly Pro Tyr Gly
                595                 600                 605

Pro Gly Ala Ser Ala Ala Ala Ala Gly Gln Asn Gly Pro Gly Ser
                610                 615                 620

Gly Gln Gln Gly Pro Gly Ser Gly Gln Tyr Gly Pro Gly Gln Gln
625                 630                 635                 640

Gly Pro Gly Gln Gln Gly Pro Gly Ser Ser Ala Ala Ala Ala Gly
                645                 650                 655

Pro Gly Gln Tyr Gly Pro Gly Gln Gln Gly Pro Ser Ala Ser Ala Ala
                660                 665                 670

Ala Ala Ala Gly Pro Gly Ser Gly Gln Gln Gly Pro Gly Ala Ser Gly
                675                 680                 685

Gln Tyr Gly Pro Gly Gln Gln Gly Pro Gly Gln Gln Gly Pro Gly Ser
                690                 695                 700

Ser Ala Ala Ala Ala Ala Gly Gln Tyr Gly Ser Gly Pro Gly Gln Gln
```

-continued

```
            705                 710                 715                 720
Gly Pro Tyr Gly Ser Ala Ala Ala Ala Gly Pro Gly Ser Gly Gln
                    725                 730                 735
Tyr Gly Gln Gly Pro Tyr Gly Pro Gly Ala Ser Gly Pro Gly Gln Tyr
                    740                 745                 750
Gly Pro Gly Gln Gln Gly Pro Ser Ala Ser Ala Ala Ala Ala Gly
                    755                 760                 765
Ser Gly Gln Gln Gly Pro Gly Gln Tyr Gly Pro Tyr Ala Ser Ala Ala
            770                 775                 780
Ala Ala Ala Gly Gln Tyr Gly Ser Gly Pro Gly Gln Gln Gly Pro Tyr
785                 790                 795                 800
Gly Pro Gly Gln Ser Gly Ser Gly Gln Gln Gly Pro Gly Gln Gln Gly
                    805                 810                 815
Pro Tyr Ala Ser Ala Ala Ala Ala Gly Pro Gly Gln Gln Gly Pro
                    820                 825                 830
Tyr Gly Pro Gly Ser Ser Ala Ala Ala Ala Gly Gln Tyr Gly Tyr
                    835                 840                 845
Gly Pro Gly Gln Gln Gly Pro Tyr Gly Pro Gly Ala Ser Gly Gln Asn
            850                 855                 860
Gly Pro Gly Ser Gly Gln Tyr Gly Pro Gly Gln Gln Gly Pro Gly Gln
865                 870                 875                 880
Ser Ala Ala Ala Ala Gly Pro Gly Gln Gln Gly Pro Tyr Gly Pro
                    885                 890                 895
Gly Ala Ser Ala Ala Ala Ala Gly Gln Tyr Gly Pro Gly Gln Gln
                    900                 905                 910
Gly Pro Gly Gln Tyr Gly Pro Gly Ser Ser Gly Pro Gly Gln Gln Gly
                    915                 920                 925
Pro Tyr Gly Pro Gly Ser Ser Ala Ala Ala Ala Gly Gln Tyr Gly
                    930                 935                 940
Pro Gly Gln Gln Gly Pro Tyr Gly Pro Gly Gln Ser Ala Ala Ala Ala
945                 950                 955                 960
Ala Gly Gln Tyr Gln Gln Gly Pro Gly Gln Gln Gly Pro Tyr Gly Pro
                    965                 970                 975
Gly Ala Ser Gly Pro Gly Gln Gln Gly Pro Tyr Gly Pro Gly Ala Ser
                    980                 985                 990
Ala Ala Ala Ala Ala Gly Pro Gly Gln Tyr Gly Pro Gly Gln Gln Gly
                    995                 1000                1005
Pro Ser Ala Ser Ala Ala Ala Ala Gly Gln Tyr Gly Ser Gly
            1010                1015                1020
Pro Gly Gln Tyr Gly Pro Tyr Gly Pro Gly Gln Ser Gly Pro Gly
            1025                1030                1035
Ser Gly Gln Gln Gly Gln Gly Pro Tyr Gly Pro Gly Ala Ser Ala
            1040                1045                1050
Ala Ala Ala Ala Gly Gln Tyr Gly Pro Gly Gln Gln Gly Pro Tyr
            1055                1060                1065
Gly Pro Gly Gln Ser Ala Ala Ala Ala Ala Gly Pro Gly Ser Gly
            1070                1075                1080
Gln Tyr Gly Pro Gly Ala Ser Gly Gln Asn Gly Pro Gly Ser Gly
            1085                1090                1095
Gln Tyr Gly Pro Gly Gln Gln Gly Pro Gly Gln Ser Ala Ala Ala
            1100                1105                1110
Ala Ala Gly Gln Tyr Gln Gln Gly Pro Gly Gln Gln Gly Pro Tyr
            1115                1120                1125
```

-continued

```
Gly Pro Gly Ala Ser Ala Ala Ala Ala Gly Gln Tyr Gly Ser
    1130                1135                1140

Gly Pro Gly Gln Gln Gly Pro Tyr Gly Pro Gly Gln Ser Gly Ser
    1145                1150                1155

Gly Gln Gln Gly Pro Gly Gln Gly Pro Tyr Ala Ser Ala Ala
    1160                1165                1170

Ala Ala Ala Gly Pro Gly Ser Gly Gln Gln Gly Pro Gly Ala Ser
    1175                1180                1185

Gly Gln Gln Gly Pro Tyr Gly Pro Gly Ala Ser Ala Ala Ala
    1190                1195                1200

Ala Gly Gln Asn Gly Pro Gly Ser Gly Gln Gly Pro Gly Gln
    1205                1210                1215

Ser Gly Gln Tyr Gly Pro Gly Gln Gln Gly Pro Gly Gln Gln Gly
    1220                1225                1230

Pro Gly Ser Ser Ala Ala Ala Ala Gly Pro Gly Gln Tyr Gly
    1235                1240                1245

Pro Gly Gln Gln Gly Pro Ser Ala Ser Ala Ala Ala Ala Ala Gly
    1250                1255                1260

Pro Gly Ser Gly Gln Gln Gly Pro Gly Ala Ser Gly Gln Tyr Gly
    1265                1270                1275

Pro Gly Gln Gln Gly Pro Gly Gln Gln Gly Pro Gly Ser Ser Ala
    1280                1285                1290

Ala Ala Ala Ala Gly Gln Tyr Gly Ser Gly Pro Gly Gln Gln Gly
    1295                1300                1305

Pro Tyr Gly Ser Ala Ala Ala Ala Gly Pro Gly Ser Gly Gln
    1310                1315                1320

Tyr Gly Gln Gly Pro Tyr Gly Pro Gly Ala Ser Gly Pro Gly Gln
    1325                1330                1335

Tyr Gly Pro Gly Gln Gln Gly Pro Ser Ala Ser Ala Ala Ala Ala
    1340                1345                1350

Ala Gly Ser Gly Gln Gln Gly Pro Gly Gln Tyr Gly Pro Tyr Ala
    1355                1360                1365

Ser Ala Ala Ala Ala Gly Gln Tyr Gly Ser Gly Pro Gly Gln
    1370                1375                1380

Gln Gly Pro Tyr Gly Pro Gly Gln Ser Gly Ser Gly Gln Gln Gly
    1385                1390                1395

Pro Gly Gln Gln Gly Pro Tyr Ala Ser Ala Ala Ala Ala Ala Gly
    1400                1405                1410

Pro Gly Gln Gln Gly Pro Tyr Gly Pro Gly Ser Ser Ala Ala Ala
    1415                1420                1425

Ala Ala Gly Gln Tyr Gly Tyr Gly Pro Gly Gln Gln Gly Pro Tyr
    1430                1435                1440

Gly Pro Gly Ala Ser Gly Gln Asn Gly Pro Gly Ser Gly Gln Tyr
    1445                1450                1455

Gly Pro Gly Gln Gln Gly Pro Gly Gln Ser Ala Ala Ala Ala Ala
    1460                1465                1470

Gly Pro Gly Gln Gln Gly Pro Tyr Gly Pro Gly Ala Ser Ala Ala
    1475                1480                1485

Ala Ala Ala Gly Gln Tyr Gly Pro Gly Gln Gln Gly Pro Gly Gln
    1490                1495                1500

Tyr Gly Pro Gly Ser Ser Gly Pro Gly Gln Gln Gly Pro Tyr Gly
    1505                1510                1515
```

-continued

Pro Gly Ser Ser Ala Ala Ala Ala Gly Gln Tyr Gly Pro Gly
1520                1525                1530

Gln Gln Gly Pro Tyr Gly Pro Gly Gln Ser Ala Ala Ala Ala
1535                1540                1545

Gly Gln Tyr Gln Gln Gly Pro Gly Gln Gly Pro Tyr Gly Pro
1550                1555                1560

Gly Ala Ser Gly Pro Gly Gln Gln Gly Pro Tyr Gly Pro Gly Ala
1565                1570                1575

Ser Ala Ala Ala Ala Gly Pro Gly Gln Tyr Gly Pro Gly Gln
1580                1585                1590

Gln Gly Pro Ser Ala Ser Ala Ala Ala Ala Gly Gln Tyr Gly
1595                1600                1605

Ser Gly Pro Gly Gln Tyr Gly Pro Tyr Gly Pro Gly Gln Ser Gly
1610                1615                1620

Pro Gly Ser Gly Gln Gln Gly Gln Gly Pro Tyr Gly Pro Gly Ala
1625                1630                1635

Ser Ala Ala Ala Ala Gly Gln Tyr Gly Pro Gly Gln Gln Gly
1640                1645                1650

Pro Tyr Gly Pro Gly Gln Ser Ala Ala Ala Ala Gly Pro Gly
1655                1660                1665

Ser Gly Gln Tyr Gly Pro Gly Ala Ser Gly Gln Asn Gly Pro Gly
1670                1675                1680

Ser Gly Gln Tyr Gly Pro Gly Gln Gln Gly Pro Gly Gln Ser Ala
1685                1690                1695

Ala Ala Ala Gly Gln Tyr Gln Gln Gly Pro Gly Gln Gln Gly
1700                1705                1710

Pro Tyr Gly Pro Gly Ala Ser Ala Ala Ala Ala Gly Gln Tyr
1715                1720                1725

Gly Ser Gly Pro Gly Gln Gln Gly Pro Tyr Gly Pro Gly Gln Ser
1730                1735                1740

Gly Ser Gly Gln Gln Gly Pro Gly Gln Gln Gly Pro Tyr Ala Ser
1745                1750                1755

Ala Ala Ala Ala Gly Pro Gly Ser Gly Gln Gln Gly Pro Gly
1760                1765                1770

Ala Ser Gly Gln Gln Gly Pro Tyr Gly Pro Gly Ala Ser Ala Ala
1775                1780                1785

Ala Ala Ala Gly Gln Asn Gly Pro Gly Ser Gly Gln Gln Gly Pro
1790                1795                1800

Gly Gln Ser Gly Gln Tyr Gly Pro Gly Gln Gln Gly Pro Gly Gln
1805                1810                1815

Gln Gly Pro Gly Ser Ser Ala Ala Ala Ala Gly Pro Gly Gln
1820                1825                1830

Tyr Gly Pro Gly Gln Gln Gly Pro Ser Ala Ser Ala Ala Ala Ala
1835                1840                1845

Ala Gly Pro Gly Ser Gly Gln Gln Gly Pro Gly Ala Ser Gly Gln
1850                1855                1860

Tyr Gly Pro Gly Gln Gln Gly Pro Gly Gln Gln Gly Pro Gly Ser
1865                1870                1875

Ser Ala Ala Ala Ala Ala Gly Gln Tyr Gly Ser Gly Pro Gly Gln
1880                1885                1890

Gln Gly Pro Tyr Gly Ser Ala Ala Ala Ala Gly Pro Gly Ser
1895                1900                1905

Gly Gln Tyr Gly Gln Gly Pro Tyr Gly Pro Gly Ala Ser Gly Pro

-continued

```
            1910                1915                1920
Gly Gln Tyr Gly Pro Gly Gln Gln Gly Pro Ser Ala  Ser Ala Ala
            1925                1930                1935
Ala Ala Ala Gly Ser Gly Gln Gln Gly Pro Gly Gln  Tyr Gly Pro
            1940                1945                1950
Tyr Ala Ser Ala Ala Ala Ala Gly Gln Tyr Gly  Ser Gly Pro
            1955                1960                1965
Gly Gln Gln Gly Pro Tyr Gly Pro Gly Gln Ser Gly  Ser Gly Gln
            1970                1975                1980
Gln Gly Pro Gly Gln Gln Gly Pro Tyr Ala Ser Ala  Ala Ala Ala
            1985                1990                1995
Ala Gly Pro Gly Gln Gln Gly Pro Tyr Gly Pro Gly  Ser Ser Ala
            2000                2005                2010
Ala Ala Ala Ala Gly Gln Tyr Gly Tyr Gly Pro Gly  Gln Gln Gly
            2015                2020                2025
Pro Tyr Gly Pro Gly Ala Ser Gly Gln Asn Gly Pro  Gly Ser Gly
            2030                2035                2040
Gln Tyr Gly Pro Gly Gln Gln Gly Pro Gly Gln Ser  Ala Ala Ala
            2045                2050                2055
Ala Ala Gly Pro Gly Gln Gln Gly Pro Tyr Gly Pro  Gly Ala Ser
            2060                2065                2070
Ala Ala Ala Ala Ala Gly Gln Tyr Gly Pro Gly Gln  Gln Gly Pro
            2075                2080                2085
Gly Gln Tyr Gly Pro Gly Ser Ser Gly Pro Gly Gln  Gln Gly Pro
            2090                2095                2100
Tyr Gly Pro Gly Ser Ser Ala Ala Ala Ala Gly  Gln Tyr Gly
            2105                2110                2115
Pro Gly Gln Gln Gly Pro Tyr Gly Pro Gly Gln Ser  Ala Ala Ala
            2120                2125                2130
Ala Ala Gly Gln Tyr Gln Gln Gly Pro Gly Gln Gln  Gly Pro Tyr
            2135                2140                2145
Gly Pro Gly Ala Ser Gly Pro Gly Gln Gln Gly Pro  Tyr Gly Pro
            2150                2155                2160
Gly Ala Ser Ala Ala Ala Ala Gly Pro Gly Gln  Tyr Gly Pro
            2165                2170                2175
Gly Gln Gln Gly Pro Ser Ala Ser Ala Ala Ala Ala  Ala Gly Gln
            2180                2185                2190
Tyr Gly Ser Gly Pro Gly Gln Tyr Gly Pro Tyr Gly  Pro Gly Gln
            2195                2200                2205
Ser Gly Pro Gly Ser Gly Gln Gln Gly Gln Gly Pro  Tyr Gly Pro
            2210                2215                2220
Gly Ala Ser Ala Ala Ala Ala Gly Gln Tyr Gly  Pro Gly Gln
            2225                2230                2235
Gln Gly Pro Tyr Gly Pro Gly Gln Ser Ala Ala Ala  Ala Ala Gly
            2240                2245                2250
Pro Gly Ser Gly Gln Tyr Gly Pro Gly Ala Ser Gly  Gln Asn Gly
            2255                2260                2265
Pro Gly Ser Gly Gln Tyr Gly Pro Gly Gln Gln Gly  Pro Gly Gln
            2270                2275                2280
Ser Ala Ala Ala Ala Ala Gly Gln Tyr Gln Gln Gly  Pro Gly Gln
            2285                2290                2295
Gln Gly Pro Tyr Gly Pro Gly Ala Ser Ala Ala Ala  Ala Ala Gly
            2300                2305                2310
```

Gln Tyr Gly Ser Gly Pro Gly Gln Gln Gly Pro Tyr Gly Pro Gly
         2315                2320                2325

Gln Ser Gly Ser Gly Gln Gln Gly Pro Gly Gln Gln Gly Pro Tyr
    2330                2335                2340

Ala Ser Ala Ala Ala Ala Ala Gly Pro Gly Ser Gly Gln Gln Gly
    2345                2350                2355

Ser Ser Val Asp Lys Leu Ala Ala Ala Leu Glu His His His His
    2360                2365                2370

His His
    2375

<210> SEQ ID NO 18
<211> LENGTH: 542
<212> TYPE: PRT
<213> ORGANISM: Artificial Sequence
<220> FEATURE:
<223> OTHER INFORMATION: ADF3Kai_noNR with His Tag

<400> SEQUENCE: 18

Met His His His His His His His His His Ser Ser Gly Ser Ser
1               5                   10                  15

Leu Glu Val Leu Phe Gln Gly Pro Ala Arg Ala Gly Ser Gln Gln
                20                  25                  30

Gly Pro Gly Gln Gln Gly Pro Gly Gln Gln Gly Pro Gly Gln Gln
            35                  40                  45

Pro Tyr Gly Pro Gly Ala Ser Ala Ala Ala Ala Ala Gly Gly Tyr
        50                  55                  60

Gly Pro Gly Ser Gly Gln Gln Gly Pro Ser Gln Gln Gly Pro Gly
65                  70                  75                  80

Gln Gly Pro Gly Gly Gln Gly Pro Tyr Gly Pro Gly Ala Ser Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
            165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
            210                 215                 220

Ala Ala Ala Gly Gly Tyr Gly Pro Gly Ser Gly Gln Gln Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gln Gly Pro Tyr Gly
            355                 360                 365

Pro Gly Ala Ser Ala Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala
            530                 535                 540

<210> SEQ ID NO 19
<211> LENGTH: 519
<212> TYPE: PRT
<213> ORGANISM: Artificial Sequence
<220> FEATURE:
<223> OTHER INFORMATION: ADF3Kai_noNR without His Tag

<400> SEQUENCE: 19

Met Ala Arg Ala Gly Ser Gly Gln Gln Gly Pro Gly Gln Gln Gly Pro
1               5                   10                  15

Gly Gln Gln Gly Pro Gly Gln Gln Gly Pro Tyr Gly Pro Gly Ala Ser
            20                  25                  30

Ala Ala Ala Ala Ala Ala Gly Gly Tyr Gly Pro Gly Ser Gly Gln Gln
            35                  40                  45

Gly Pro Ser Gln Gln Gly Pro Gly Gln Gln Gly Pro Gly Gly Gln Gly
            50                  55                  60

Pro Tyr Gly Pro Gly Ala Ser Ala Ala Ala Ala Ala Ala Gly Gly Tyr
65                  70                  75                  80

Gly Pro Gly Ser Gly Gln Gln Gly Pro Gly Gln Gly Pro Tyr Gly
                85                  90                  95

Pro Gly Ser Ser Ala Ala Ala Ala Ala Ala Gly Gly Asn Gly Pro Gly
                100                 105                 110

```
Ser Gly Gln Gln Gly Ala Gly Gln Gln Gly Pro Gly Gln Gln Gly Pro
        115                 120                 125

Gly Ala Ser Ala Ala Ala Ala Ala Gly Gly Tyr Gly Pro Gly Ser
        130                 135                 140

Gly Gln Gln Gly Pro Gly Gln Gln Gly Pro Gly Gln Gln Gly Pro Tyr
145                 150                 155                 160

Gly Pro Gly Ala Ser Ala Ala Ala Ala Ala Gly Gly Tyr Gly Pro
                165                 170                 175

Gly Ser Gly Gln Gly Pro Gly Gln Gln Gly Pro Gly Gln Gln Gly Pro
            180                 185                 190

Tyr Gly Pro Gly Ala Ser Ala Ala Ala Ala Ala Gly Gly Tyr Gly
            195                 200                 205

Pro Gly Ser Gly Gln Gln Gly Pro Gly Gln Gln Gly Pro Gly Gln Gln
        210                 215                 220

Gly Pro Gly Gly Gln Gly Pro Tyr Gly Pro Gly Ala Ser Ala Ala Ala
225                 230                 235                 240

Ala Ala Ala Gly Gly Tyr Gly Pro Gly Tyr Gly Gln Gln Gly Pro Gly
                245                 250                 255

Gln Gln Gly Pro Gly Gly Gln Gly Pro Tyr Gly Pro Gly Ala Ser Ala
        260                 265                 270

Ala Ser Ala Ala Ser Gly Gly Tyr Gly Pro Gly Ser Gly Gln Gln Gly
        275                 280                 285

Pro Gly Gln Gln Gly Pro Gly Gly Gly Pro Tyr Gly Pro Gly Ala
        290                 295                 300

Ser Ala Ala Ala Ala Ala Gly Gly Tyr Gly Pro Gly Ser Gly Gln
305                 310                 315                 320

Gln Gly Pro Gly Gln Gln Gly Pro Gly Gln Gln Gly Pro Gly Gln Gln
        325                 330                 335

Gly Pro Gly Gly Gln Gly Pro Tyr Gly Pro Gly Ala Ser Ala Ala Ala
        340                 345                 350

Ala Ala Ala Gly Gly Tyr Gly Pro Gly Ser Gly Gln Gln Gly Pro Gly
        355                 360                 365

Gln Gln Gly Pro Gly Gln Gln Gly Pro Gly Gln Gln Gly Pro Gly Gln
        370                 375                 380

Gln Gly Pro Gly Gln Gln Gly Pro Gly Gln Gln Gly Pro Gly Gln Gln
385                 390                 395                 400

Gly Pro Gly Gln Gln Gly Pro Gly Gly Gln Gly Ala Tyr Gly Pro Gly
                405                 410                 415

Ala Ser Ala Ala Ala Gly Ala Ala Gly Gly Tyr Gly Pro Gly Ser Gly
        420                 425                 430

Gln Gln Gly Pro Gly Gln Gln Gly Pro Gly Gln Gln Gly Pro Gly Gln
        435                 440                 445

Gln Gly Pro Gly Gln Gln Gly Pro Gly Gln Gln Gly Pro Gly Gln Gln
        450                 455                 460

Gly Pro Gly Gln Gln Gly Pro Tyr Gly Pro Gly Ala Ser Ala Ala Ala
465                 470                 475                 480

Ala Ala Ala Gly Gly Tyr Gly Pro Gly Ser Gly Gln Gln Gly Pro Gly
                485                 490                 495

Gln Gln Gly Pro Gly Gln Gln Gly Pro Gly Gln Gly Pro Tyr Gly
        500                 505                 510

Pro Gly Ala Ala Ser Ala Ala
        515
```

```
<210> SEQ ID NO 20
<211> LENGTH: 24
<212> TYPE: PRT
<213> ORGANISM: Artificial Sequence
<220> FEATURE:
<223> OTHER INFORMATION: His tag and start codon

<400> SEQUENCE: 20

Met His His His His His His His His His Ser Ser Gly Ser Ser
1               5                   10                  15

Leu Glu Val Leu Phe Gln Gly Pro
            20

<210> SEQ ID NO 21
<211> LENGTH: 12
<212> TYPE: PRT
<213> ORGANISM: Artificial Sequence
<220> FEATURE:
<223> OTHER INFORMATION: HisTag

<400> SEQUENCE: 21

Met His His His His His His Ser Ser Gly Ser Ser
1               5                   10
```